US009957524B2

(12) United States Patent
Bowen et al.

(10) Patent No.: US 9,957,524 B2
(45) Date of Patent: May 1, 2018

(54) PESTICIDAL TOXIN PROTEINS ACTIVE AGAINST COLEOPTERAN INSECTS

(71) Applicant: Monsanto Technology LLC, St. Louis, MO (US)

(72) Inventors: David J. Bowen, Glencoe, MO (US); Catherine A. Chay, Ballwin, MO (US); Stanislaw Flasinski, Chesterfield, MO (US); Xiaoran Fu, Belmont, MA (US); Uma R. Kesanapalli, Chesterfield, MO (US); Jason S. Milligan, Troy, IL (US); Rachael N. Slightom, Maplewood, MO (US); Daqi Tu, Chesterfield, MO (US); Andrew M. Wollacott, Boston, MA (US); Yong Yin, Creve Coeur, MO (US)

(73) Assignee: Monsanto Technology LLC, St. Louis, MO (US)

( * ) Notice: Subject to any disclaimer, the term of this patent is extended or adjusted under 35 U.S.C. 154(b) by 166 days.

(21) Appl. No.: 14/671,542

(22) Filed: Mar. 27, 2015

(65) Prior Publication Data

US 2015/0274786 A1 Oct. 1, 2015

Related U.S. Application Data

(60) Provisional application No. 61/971,855, filed on Mar. 28, 2014.

(51) Int. Cl.
*C12N 15/82* (2006.01)
*C07K 14/325* (2006.01)
*A01N 63/02* (2006.01)

(52) U.S. Cl.
CPC ........ *C12N 15/8286* (2013.01); *C07K 14/325* (2013.01); *A01N 63/02* (2013.01)

(58) Field of Classification Search
None
See application file for complete search history.

(56) References Cited

U.S. PATENT DOCUMENTS

| | | | |
|---|---|---|---|
| 5,500,365 | A | 3/1996 | Fischhoff et al. |
| 5,880,275 | A | 3/1999 | Fischhoff et al. |
| 6,033,874 | A | 3/2000 | Baum et al. |
| 6,344,553 | B1 | 2/2002 | Bradfisch et al. |
| 6,501,009 | B1 | 12/2002 | Romano |
| 6,551,962 | B1 | 4/2003 | Pershing et al. |
| 6,713,063 | B1 | 3/2004 | Malvar et al. |
| 6,962,705 | B2 | 11/2005 | Malvar et al. |
| 7,064,249 | B2 | 6/2006 | Corbin et al. |
| 7,070,982 | B2 | 7/2006 | Malvar et al. |
| 7,510,878 | B2 | 3/2009 | Abad et al. |
| 7,772,465 | B2 | 8/2010 | Abad et al. |
| 7,812,129 | B1 | 10/2010 | Abad et al. |
| 8,188,036 | B2 | 5/2012 | Abad et al. |
| 8,609,936 | B2 | 12/2013 | Baum et al. |
| 2006/0021087 | A1 | 1/2006 | Baum et al. |
| 2006/0112447 | A1 | 5/2006 | Bogdanova et al. |
| 2008/0172762 | A1 | 7/2008 | Cerf et al. |
| 2009/0313721 | A1 | 12/2009 | Abad et al. |
| 2010/0017914 | A1 | 1/2010 | Hart et al. |
| 2010/0077507 | A1 | 3/2010 | Abad et al. |
| 2010/0077508 | A1 | 3/2010 | Abad et al. |
| 2010/0192256 | A1 | 7/2010 | Abad et al. |
| 2010/0269221 | A1 | 10/2010 | Abad et al. |
| 2011/0055968 | A1 | 3/2011 | Cerf et al. |
| 2011/0112013 | A1 | 5/2011 | Abad et al. |
| 2011/0154536 | A1 | 6/2011 | Abad et al. |
| 2012/0047606 | A1 | 2/2012 | Abad et al. |
| 2012/0117690 | A1 | 5/2012 | Cerf et al. |
| 2012/0167259 | A1 | 6/2012 | Liu et al. |
| 2012/0192310 | A1 | 7/2012 | Abad et al. |
| 2012/0233726 | A1 | 9/2012 | Abad et al. |
| 2013/0097735 | A1 | 4/2013 | Bowen et al. |
| 2013/0227743 | A1 * | 8/2013 | Grandlic ................ C12Q 1/689 800/279 |
| 2013/0269060 | A1 | 10/2013 | Baum et al. |

(Continued)

FOREIGN PATENT DOCUMENTS

| | | | |
|---|---|---|---|
| WO | WO 2005/019412 A2 | | 3/2005 |
| WO | WO 2005/019414 | * | 3/2005 |
| WO | WO 2013/028563 A2 | | 2/2013 |
| WO | WO 2014/008054 A2 | | 1/2014 |

OTHER PUBLICATIONS

Genbank EEM92866 (2009).*
Genbank ACNK01000120 (2009).*
Argolo-Filho et al, 2014, Insects 5:62-91.*
GenBank KIP23433.1 (2015).*
Guo et al, 2004, Proc. Natl. Acad. Sci. USA 101: 9205-9210.*
Zwick et al (2012, Genome Res. 22:1512-1524).*
International Search Report and Written Opinion dated Jul. 16, 2015, as received in International Application No. PCT/US2015/023091.

(Continued)

*Primary Examiner* — Anne Kubelik
(74) *Attorney, Agent, or Firm* — Timothy K. Ball; Carine M. Doyle; Arnold & Porter Kaye Scholer LLP

(57) ABSTRACT

The invention generally relates to the field of insect inhibitory toxin proteins. A novel class of proteins exhibiting insect inhibitory activity against agriculturally relevant pests of crop plants and seeds are disclosed. Insecticidal activity is particularly effective against the Coleopteran order of insect pests. Plants, plant parts, and seed are provided containing a polynucleotide construct encoding one or more of the toxin proteins disclosed herein. The proteins are referred to herein variously as the TIC2463-related toxin protein class or family, the TIC2463-related toxin proteins, the TIC2463-related protein genus, toxin proteins related to the TIC2463 toxin protein, proteins related to TIC2463, TIC2463-related toxin polypeptides, TIC2463-related pesticidal proteins, and the like.

4 Claims, 5 Drawing Sheets

(56) References Cited

U.S. PATENT DOCUMENTS

| | | | |
|---|---|---|---|
| 2014/0007292 | A1 | 1/2014 | Cerf et al. |
| 2014/0033361 | A1 | 1/2014 | Altier et al. |
| 2014/0366227 | A1 | 12/2014 | Gatehouse et al. |

OTHER PUBLICATIONS

Liu et al., "Construction of a *Bacillus thuringiensis* engineered strain with high toxicity and broad pesticidal spectrum against coleopteran insects," *Applied Microbiology Biotechnology*, 87(1):243-249 (2010).

Oleson et al., "Node-Injury Scale to Evaluate Root Injury by Corn Rootworms (Coleoptera: Chrysomelidae)," *Journal of Economic Entomology*, 98(1):1-8 (2005).

Thompson et al., "CLUSTAL W: improving the sensitivity of progressive multiple sequence alignment through sequence weighting, position-specific gap penalties weight matrix choice," *Nucleic Acids Research*, 22(22):4673-4680 (1994).

Yu et al., "Co-expression and Synergism Analysis of Vip3Aa29 and Cyt2Aa3 Insecticial Proteins from *Bacillus thuringiensis,*" *Current Microbiology*, 64(4):326-331 (2012).

Zwick et al., "Genomic characterization of the *Bacillus cereus sensu lato* species: backdrop to the evolution of Bacillus anthracis," *Genome Res*., 22(8):1512-1524 (2012).

Partial Supplementary International Search Report dated Oct. 11, 2017, as received in International Application No. PCT/US2015/023091.

* cited by examiner

```
40 TIC1373          --------------------------------------------------------------------------MADQTAN---------  7
42 WP_000699779     MKILWKPQKTFISNLGIVLG-ISS-------TLFFGSN-----------------------------------VMADQTAN--------- 38
 4 TIC2463          MKILWKPQKTFISNLAIVLG-ISS-------TLFFGSN-----------------------------------VMADQTAN--------- 38
14 TIC2593          MKILWKPQKTFISNLAIVLG-ISS-------TLFFGSN-----------------------------------VMADQTAN--------- 38
16 TIC2598          MKILWKPQKAFISNLAIVLG-ISS-------TLFFGSN-----------------------------------VMADQTAN--------- 38
 2 TIC1825          MTNLFKSQKTFIAKLGIVLG-ISS-------TLFFGSN-----------------------------------VMAAQTTN--------- 38
12 TIC3005          MKTLFKIKKTFITKLGIILG-ISS-------TMFFGNN-----------------------------------VMAAQAAN--------- 38
20 TIC3090          MK-LKSIFKCVT--ITAVLSQIAVYPVTSYAVSNIEQNSDNKKITEEKSDML------------------GNSLLLNVHESSVKAAYSSN 69
18 TIC3891          MK-LKSIFKCVT--ITAVLSQIAVYPVTSYAVSNIEQNSDNKKITEEKSDML------------------GNGSLLNVHESSVKAAYSSN 69
 6 TIC2461          ME-LKRIWKCLT--ISAVLSQIAVYPVTSYAVSNTEQNTDNMKITEEKSNMI------------------RNGLLGNVHKSSVKSAYSSN 69
 8 TIC3037          MKNKKNIFKMCS--ATLALS-LG-------VTVFVPTAS--------YAAIT------------------NDKFLSPVTST------DSN 48
22 TIC3626          MR-KKLIVTTAS--LSLALTSFGS------ITSLAESNNQQNKMIEINGNTS------------------DSSILSPITS--------NI 55
24 TIC2081          MR-KKLIVTTAS--LSLALTSFGS------ITSLAESNNQQNKMVEVNGTTS------------------NSFILSPITS--------NI 55
10 TIC2228          MR-KKLIVTTAS--LSLALTSFGS------ITSLAESNNQQNKRIEVNGTTS------------------NSSILSPITS--------NI 55
55 TIC2461_5        ------------------------------MVSNTEQNTDNMKITEEKSNMI------------------RNGLLGNVHKSSVKSAYSSN 42
26 TIC1825_V1       MTNLFKSQKTFIAKLGIVLG-ISS-------TLFFGSN-----------------------------------VMAAQTTN--------- 38
28 TIC1825_V2       MTNLFKSQKTFIAKLGIVLG-ISS-------TLFFGSN-----------------------------------VMAAQTTN--------- 38
30 TIC1825_V3       MTNLFKSQKTFIAKLGIVLG-ISS-------TLFFGSN-----------------------------------VMAAQTTN--------- 38
49 TIC1825_12       ---------------------------------------------------------------------------MAQTTN---------  6
51 TIC1825_13       ---------------------------------------------------------------------------MAQTTN---------  6
53 TIC1825_15       ---------------------------------------------------------------------------MAQTTN---------  6
32 TIC2463_3        --------------------------------------------------------------------------MADQTAN---------  7
34 TIC2463_4        ---------------------------------------------------------------------------MDQTAN---------  6
57 TIC2463_8        MKILWKPQKTFISNLAIVLG-AAP-------FLFFGSN-----------------------------------VMADQTAN--------- 38
59 TIC2463_9        MKILWKPQKTFISNLAIVLG-ISS-------TLFFGSN-----------------------------------VMRDQTAN--------- 38
61 TIC2463_10       MKILWKPQKTFISNLAIVLG-ISS-------TLFFGSN-----------------------------------VMADQTAN--------- 38
36 TIC2463_Ts-Wx    MA-ALATSQLATTRAGFGLGDASSSMFRPGVQGLRGSRASSPAATLSVRTSARAAPRQQHRRAQRGARFPSLVVCADQTAN--------- 80
38 TIC2463_Ts-CR88  MAPALSRSLYTSPLTSVPITPVSS---R--LSHLRSSFLPHGGA---LRTGV-SCSWNLEKRCNR------FAVKCDQTAN--------- 66
```

*FIG. 1A*

```
40 TIC1373          ITDVDAQMDKISDFYFKNELEWKDLPEYPGAYHYIRLDSKKTNMDLDLKANNIKNLTYSDLNPEYVGENEFDNTNSNIDQTFTTAAYSHQ  97
42 WP_000699779     ITDVDVQMDKISDFYFKNELQWKDLPEYPGAYHYIRLDSKKTNMDLDLKANNIKNLTYSDLNPEYVGENEFDNTNSNIDQTFTTAAYSHQ 128
 4 TIC2463          ITDVDAQMDKISDFYFKNELEWKDLPEYPGAYHYIRLDSKKTNMDLDLKANNIKNLTYSDLNPEYVGENEFDNTNSNIDQTFTTAAYSHQ 128
14 TIC2593          ITDVDAQMDKISDFYFKNELEWKDLPEYPGAYHYIRLDSKKTNMDLDLKANNIKNLTYSELNPEYVGENEFDNTNSNIDQTFTTAAYSHQ 128
16 TIC2598          ITDVDAQMDKISDFYFKNELEWKYLPEYPGAYHYIRLDSKKTNMDLDLKANNIKNLIYSDLNPEYVGENEFDNTHSNIDQTFTTAAYSHQ 128
 2 TIC1825          ITDVDAQMDKISDFYFKNELEWKDLPEYPGAYHYIRLDSKKTNMDLDLKASNLKNLTYSDLHPEYIGENEFDNTNGSIDQTFTTASYSHQ 128
12 TIC3005          IIDVDAQMDKISDFYFKSELKWKDVADFPGAYHYIRLDSKKTNMDLDLKTSNLKNLTYSDLNPEYIGENEFDNTNGVTEQTFTTAWYSHQ 128
20 TIC3090          ITNVDEQMNKISDFYYQNNLAWKEISTN---FLVDRLKEKKTTMSLDLNASDINNLTYNDLQPEYIGENEFENTTD-QEQTFTTASYSHT 155
18 TIC3891          VTNVDEQMNKISDFYYQNNLAWKEISTY---YLVDQLKEKKTTMSLDLNASDINNLTYNDLQPEYIGENEFENKTD-QEQTFTTAPYSHT 155
 6 TIC2461          VTNVDEQMNKISDFYYQNNLRGKEISTY---YYVNQLKEKKTTMSLDLNASDINNVTYNDLQPEYIGENEFQNTTD-QDQTFTTAAYSHA 155
 8 TIC3037          ITNVDDSMNKTSDFYYKNKLDNKELGSY---WRINSLQSKKTTMDLEINSSDIQNLKYSDSQPEYIGENEFKNDTN-EEQIMTTATYSHE 134
22 TIC3626          ITDVDQQMNKISDYYYNNNLKLKDIGDY---YHIIRLENKNTTMSFDLNADHIKNLHYNDLQPQYIGENEFKNTTD-QEQTFTTASYSQA 141
24 TIC2081          ITDVDQQMNKISDYYYNNNLKLKDIGDY---YHIIRLENKNTTMSFDLNADDIKNLHYNDLQPQYIGENEFKNTTD-QEQTFTTASYSQA 141
10 TIC2228          ITDVDQQMNKISDYYYNNNLKLKDIGDY---YHIIRLENKNTTMSFSLNADDIKNLQYNDLQPQYIGENEFKNTTD-QEQTFTTASYSQA 141
55 TIC2461_5        VTNVDEQMNKISDFYYQNNLRGKEISTY---YYVNQLKEKKTTMSLDLNASDINNVTYNDLQPEYIGENEFQNTTD-QDQTFTTAAYSHA 128
26 TIC1825_V1       ITDVDAQMDKISDFYFKNELEWKDLPEYPGAYHYIRLDSKKTNMDLDLKASNLKNLTYSDLHPEYIGENEFDNTNGSIDQTFTTASYSHQ 128
28 TIC1825_V2       ITDVDAQMDKISDFYFKNELEWKDLPEYPGAYHYIRLDSKKTNMDLDLKASNLKNLTYSDLHPEYIGENEFDNTNGSIDQTFTTASYSHQ 128
30 TIC1825_V3       ITDVDAQMDKISDFYFKNELEWKDLPEYPGAYHYIRLDSKKTNMDLDLKASNLKNLTYSDLHPEYIGENEFDNTNGSIDQTFTTASYSHQ 128
49 TIC1825_12       ITDVDAQMDKISDFYFKNELEWKDLPEYPGAYHYIRLDSKKTNMDLDLKASNLKNLTYSDLHPEYIGENEFDNTNGSIDQTFTTASYSHQ  96
51 TIC1825_13       ITDVDAQMDKISDFYFKNELEWKDLPEYPGAYHYIRLDSKKTNMDLDLKASNLKNLTYSDLHPEYIGENEFDNTNGSIDQTFTTASYSHQ  96
53 TIC1825_15       ITDVDAQMDKISDFYFKNELEWKDLPEYPGAYHYIRLDSKKTNMDLDLKASNLKNLTYSDLHPEYIGENEFDNTNGSIDQTFTTASYSHQ  96
32 TIC2463_3        ITDVDAQMDKISDFYFKNELEWKDLPEYPGAYHYIRLDSKKTNMDLDLKANNIKNLTYSDLNPEYVGENEFDNTNSNIDQTFTTAAYSHQ  97
34 TIC2463_4        ITDVDAQMDKISDFYFKNELEWKDLPEYPGAYHYIRLDSKKTNMDLDLKANNIKNLTYSDLNPEYVGENEFDNTNSNIDQTFTTAAYSHQ  96
57 TIC2463_8        ITDVDAQMDKISDFYFKNELEWKDLPEYPGAYHYIRLDSKKTNMDLDLKANNIKNLTYSDLNPEYVGENEFDNTNSNIDQTFTTAAYSHQ 128
59 TIC2463_9        ITDVDAQMDKISDFYFKNELEWKDLPEYPGAYHYIRLDSKKTNMDLDLKANNIKNLTYSDLNPEYVGENEFDNTNSNIDQTFTTAAYSHQ 128
61 TIC2463_10       ITDVRAQMDKISDFYFKNELEWKDLPEYPGAYHYIRLDSKKTNMDLDLKANNIKNLTYSDLNPEYVGENEFDNTNSNIDQTFTTAAYSHQ 128
36 TIC2463_Ts-Wx    ITDVDAQMDKISDFYFKNELEWKDLPEYPGAYHYIRLDSKKTNMDLDLKANNIKNLTYSDLNPEYVGENEFDNTNSNIDQTFTTAAYSHQ 170
38 TIC2463_Ts-CR88ITDVDAQMDKISDFYFKNELEWKDLPEYPGAYHYIRLDSKKTNMDLDLKANNIKNLTYSDLNPEYVGENEFDNTNSNIDQTFTTAAYSHQ 156
```

*FIG. 1B*

```
40 TIC1373          VTNSASTNVTKGFKVGGKT-TLLKLPILLTSGVEINAEFNSATSTTNTVTDTKTLTASPQNIKVPAGRKFLVKVDMAKKTFNGEVDFSAT 186
42 WP_000699779     VTNSASTNVTKGFKVGGKT-TLLKLPILLTSGVEINAEFNSATSTTNTVTDTKTLTASPQNIKVPAGRKFLVKVDMAKKTFNGEVDFSAT 217
 4 TIC2463          VTNSASTNVTKGFKVGGKT-TLLKLPILLTSGVEINAEFNSATSTTNTVTDTKTLTASPQNIKVPAGRKFLVKVDMAKKTFNGEVDFSAT 217
14 TIC2593          VTNSASTNVTKGFKVGGKT-TLLKLPILLTSGVEINAEFNSATSTTNTVTDTKTLTASPQNIKVPAGRKFLVKVDMAKKTFNGEVDFSAT 217
16 TIC2598          VTNSASTNVTKGFKVGGKT-TLLKLPILLTSGVEINAEFNSATSTTNTVTDTKTLTASPQNIKVPAGRKFLVKVDMAKKTFNGEVDFSAT 217
 2 TIC1825          VTNSASTSVTEGFKVGGKT-TLFKLPILLTDGVDITAEFNSATSTTNTVTDTKTLTASPQNIKVPAGKKYLVKVDMAKKTFNGDIEFSAN 217
12 TIC3005          VTNSASTSVTEGFKIGGKT-TLFKLPILLTGGIDITAEFNSATSKTNTVTDTKTLTASPQNIKVPAGKKYLVKVNMAKKTFNGDIDFRAN 217
20 TIC3090          VTDTVSSTVTNGFKIGGSGDTIFKIPILLKDGIKLSAEFNSATSTTNTTTDTKTLTASPQSIKVPAGKTYKVVVNLQKKNFTGDIDFTGK 245
18 TIC3891          VTDTVSSTVTNGFKIGGSGDTIFKIPILLKDGIKLSAEFNSATSTTNTTTDTKTLTAPSQNIKVPAGKTYKVEVNLQKKNFAGDIDFTGK 245
 6 TIC2461          VTDTVSSTVTNGFKIGGSGDTIFKIPILLKDGIKLSAEFNSATSTTNTTTDTKTLTASPQNIKVPAGKTYKVVVNLYKKSFEGDIDFTGK 245
 8 TIC3037          VRNFVDSTVTKGFQAKGEG-AFFKIPILLPDGIQLNAEFNSNDTEKKTTDDIKTLTASPQNIKVPAGKTYKVEVTLHKKNFVGDIDFQGK 223
22 TIC3626          VTNSVSSTVIQGFKATSTT-SLLKIPILLPGGINLNAEFNSASNTTTTNTTTETLTAPPQNIKVPAGRTYKVEVNLLKKKFTGDIDFHGK 230
24 TIC2081          VTNSVSSTVIQGFKATSTT-SLLKIPILLPGGINLNAEFNSASNTTTTNTTTETLTAPPQNIKVPAGRTYKVEVNLLKKKFTGDIDFHGK 230
10 TIC2228          VTNSVSSTVIQGFKATSTT-SLLKIPILLPEGINLNAEFNSASNTTTTNTTTETLTAPPQNIKVPSGRTYKVEVNLLKKKFTGDIDFHGK 230
55 TIC2461_5        VTDTVSSTVTNGFKIGGSGDTIFKIPILLKDGIKLSAEFNSATSTTNTTTDTKTLTASPQNIKVPAGKTYKVVVNLYKKSFEGDIDFTGK 218
26 TIC1825_V1       VTNSASTSVTEGFKVGGKT-TLFKLPILLTDGVDITAEFNSATSTTNTVTDTKTLTASPQNIKVPAGKKYLVKVDMAKKTFNGDIEFSAN 217
28 TIC1825_V2       VTNSASTSVTEGFKVGGKT-TLFKLPILLTDGVDITAEFNSATSTTNTVTDTKTLTASPQNIKVPAGKKYLVKVDMAKKTFNGDIEFSAN 217
30 TIC1825_V3       VTNSASTSVTEGFKVGGKT-TLFKLPILLTDGVDITAEFNSATSTTNTVTDTKTLTASPQNIKVPAGKKYLVKVDMAKKTFNGDIEFSAN 217
49 TIC1825_12       VTNSASTSVTEGFKVGGKT-TLFKLPILLTDGVDITAEFNSATSTTNTVTDTKTLTASPQNIKVPAGKKYLVKVDMAKKTFNGDIEFSAN 185
51 TIC1825_13       VTNSASTSVTEGFKVGGKT-TLFKLPILLTDGVDITAEFNSATSTTNTVTDTKTLTASPQNIKVPAGKKYLVKVDMAKKTFNGDIEFSAN 185
53 TIC1825_15       VTNSASTSVTEGFKVGGKT-TLFKLPILLTDGVDITAEFNSATSTTNTVTDTKTLTASPQNIKVPAGKKYLVKVDMAKKTFNGDIEFSAN 185
32 TIC2463_3        VTNSASTNVTKGFKVGGKT-TLLKLPILLTSGVEINAEFNSATSTTNTVTDTKTLTASPQNIKVPAGRKFLVKVDMAKKTFNGEVDFSAT 186
34 TIC2463_4        VTNSASTNVTKGFKVGGKT-TLLKLPILLTSGVEINAEFNSATSTTNTVTDTKTLTASPQNIKVPAGRKFLVKVDMAKKTFNGEVDFSAT 185
57 TIC2463_8        VTNSASTNVTKGFKVGGKT-TLLKLPILLTSGVEINAEFNSATSTTNTVTDTKTLTASPQNIKVPAGRKFLVKVDMAKKTFNGEVDFSAT 217
59 TIC2463_9        VTNSASTNVTKGFKVGGKT-TLLKLPILLTSGVEINAEFNSATSTTNTVTDTKTLTASPQNIKVPAGRKFLVKVDMAKKTFNGEVDFSAT 217
61 TIC2463_10       VTNSASTNVTKGFKVGGKT-TLLKLPILLTSGVEINAEFNSATSTTNTVTDTKTLTASPQNIKVPAGRKFLVKVDMAKKTFNGEVDFSAT 217
36 TIC2463_Ts-Wx    VTNSASTNVTKGFKVGGKT-TLLKLPILLTSGVEINAEFNSATSTTNTVTDTKTLTASPQNIKVPAGRKFLVKVDMAKKTFNGEVDFSAT 259
38 TIC2463_Ts-CR88VTNSASTNVTKGFKVGGKT-TLLKLPILLTSGVEINAEFNSATSTTNTVTDTKTLTASPQNIKVPAGRKFLVKVDMAKKTFNGEVDFSAT 245
```

*FIG. 1C*

```
                                        233
                                         x
40 TIC1373           GYNVKSTLNTLATYYAAGFPRPNKYPSLTFVTADMWKKLSTSQQNQINGVNFDSSKDLVLNGKANVHGIFGSTLRVSVYDITDSKLSPKL 276
42 WP_000699779      GYNVQSTLNTLATYYAAGFPRPNKYPSLTFVTADMWKKLSTSQ---------------------------------------------- 260
 4 TIC2463           GYNVKSTLNTLATYYAAGFPRPNKYPSLTFVTADMWKKLSTSQQNQINGVNFDSSKDLVLNGKANVHGIFGSTLRVSVYDITDSKLSPKL 307
14 TIC2593           GYNVKSTLNTLATYYAAGFPRPNKYPSLTFVTADMWKKLSTSQQNQINGVNFDSSKDLVLNGKANVHGIFGSTLRVSVYDITDSKLSPKL 307
16 TIC2598           GYNVKSTLNTLATYYAAGFPRPNKYPSLTFVTADMWKKLSTSQQNQINGVNFDSSKDLVLNGKANVHGIFGSTLRVSVYDITDPKLSPKL 307
 2 TIC1825           GKNVKSKLDTLATYYGPGFPRPNKYPSLLFTTADMWKKLSTSQQNQIKGVTFDSSKNLIILNGKAHVNGIFGSKLRVSVYDITDSKLSPKL 307
12 TIC3005           GQNVKSTLNTLATYYGPGFPRPDKCSSLTFTTADIWEKLSANSQNQIKGVNFDSNKNLIILNGKAHINGIFGSTLSVSIYDITASKKSPKL 307
20 TIC3090           ATNVNSTLTVNVAYVGPGFPRPDKEQSFTYATADMWKDLTNDQRNQITGISFDNNKNLTLNGKAKIEGIYGSKLRVSVYDITNN--AHRL 333
18 TIC3891           ATNVNSKLTVNAAYVGPGFPRLDKEQSFTYATADMWKDLTNDQRNQITGISFDNNKNLTLNGKAKIEGIYGSKLQVSVYDITNN--AHRL 333
 6 TIC2461           ATNVNSKLTVNATYVGHGFPRRDKEQSYTYATADMLKDLTNDQRNQITGISFDNNKNLTLNGKAKIEGIYGSKLQVSVYDITNN--AHRL 333
 8 TIC3037           ATNVKSDLNVREMYLGPGFPRPDRYPTYTYDTADMWKDLTNDQKNQITGIKFDDNKNLIILNGTAKLKGIYGSKLQVNIFDITNKS-TPKL 312
22 TIC3626           GTDVKSNLKVRATYYGPGFPRPTKYPTYTYSTADMWRGLTTEQKKQITGVNFNNNKDLTIDGTTKVEGIYGSDLQVVVYDITYKN-TPKI 319
24 TIC2081           GTNVKSNLKVRATYYGPGFPRPTKYPTYTYSTADMWRGLTTEQKKQITGVNFNNNKDLTIDGTTKVEGIYGSNLEVVVYDITNKN-TPKI 319
10 TIC2228           GTDVKSNLKVRATYYGPGFPRPTKYPSYTYSTADMWRGLTTEQKKQITGVNFNNNKDLTIDGTTKVEGIYGSNLEVVVYDITNKN-IPKM 319
55 TIC2461_5         ATNVNSKLTVNATYVGHGFPRRDKEQSYTYATADMLKDLTNDQRNQITGISFDNNKNLTLNGKAKIEGIYGSKLQVSVYDITNN--AHRL 306
26 TIC1825_V1        GKNVKSKLDTLATYYAPGFPRPNKYPSLLFTTADMWKKLSTSQQNQIKGVTFDSSKNLIILNGKAHVNGIFGSKLRVSVYDITDSKLSPKL 307
28 TIC1825_V2        GKNVKSKLDTLATYYGAGFPRPNKYPSLLFTTADMWKKLSTSQQNQIKGVTFDSSKNLIILNGKAHVNGIFGSKLRVSVYDITDSKLSPKL 307
30 TIC1825_V3        GKNVKSTLNTLATYYAAGFPRPNKYPSLTFVTADMWKKLSTSQQNQIKGVTFDSSKNLIILNGKAHVNGIFGSKLRVSVYDITDSKLSPKL 307
49 TIC1825_12        GKNVKSTLNTLATYYAAGFPRPNKYPSLTFVTADMWKKLSTSQQNQIKGVTFDSSKNLIILNGKAHVNGIFGSKLRVSVYDITDSKLSPKL 275
51 TIC1825_13        GYNVKSTLNTLATYYAAGFPRPNKYPSLTFVTADMWKKLSTSQQNQIKGVTFDSSKDLIILNGKAHVNGIFGSKLRVSVYDITDSKLSPKL 275
53 TIC1825_15        GKNVKSTLNTLATYYAAGFPRPNKYPSLTFVTADMWKKLSTSQQNQINGVTFDSSKNLIILNGKAHVNGIFGSKLRVSVYDITDSKLSPKL 275
32 TIC2463_3         GYNVKSTLNTLATYYAAGFPRPNKYPSLTFVTADMWKKLSTSQQNQINGVNFDSSKDLVLNGKANVHGIFGSTLRVSVYDITDSKLSPKL 276
34 TIC2463_4         GYNVKSTLNTLATYYAAGFPRPNKYPSLTFVTADMWKKLSTSQQNQINGVNFDSSKDLVLNGKANVHGIFGSTLRVSVYDITDSKLSPKL 275
57 TIC2463_8         GYNVKSTLNTLATYYAAGFPRPNKYPSLTFVTADMWKKLSTSQQNQINGVNFDSSKDLVLNGKANVHGIFGSTLRVSVYDITDSKLSPKL 307
59 TIC2463_9         GYNVKSTLNTLATYYAAGFPRPNKYPSLTFVTADMWKKLSTSQQNQINGVNFDSSKDLVLNGKANVHGIFGSTLRVSVYDITDSKLSPKL 307
61 TIC2463_10        GYNVKSTLNTLATYYAAGFPRPNKYPSLTFVTADMWKKLSTSQQNQINGVNFDSSKDLVLNGKANVHGIFGSTLRVSVYDITDSKLSPKL 307
36 TIC2463_Ts-Wx     GYNVKSTLNTLATYYAAGFPRPNKYPSLTFVTADMWKKLSTSQQNQINGVNFDSSKDLVLNGKANVHGIFGSTLRVSVYDITDSKLSPKL 349
38 TIC2463_Ts-CR88GYNVKSTLNTLATYYAAGFPRPNKYPSLTFVTADMWKKLSTSQQNQINGVNFDSSKDLVLNGKANVHGIFGSTLRVSVYDITDSKLSPKL 335
```

*FIG. 1D*

```
40 TIC1373          VQHKNI-- 282
42 WP_000699779     -------- 260
 4 TIC2463          VQHKNI-- 313
14 TIC2593          VQHKNI-- 313
16 TIC2598          VQQKNI-- 313
 2 TIC1825          IQQKFMEQ 315
12 TIC3005          IQQKNMG- 314
20 TIC3090          VQVF---- 337
18 TIC3891          VQVF---- 337
 6 TIC2461          VQVF---- 337
 8 TIC3037          VQVF---- 316
22 TIC3626          VETRTFK- 326
24 TIC2081          VETRTFK- 326
10 TIC2228          VETRTFK- 326
55 TIC2461_5        VQVF---- 310
26 TIC1825_V1       IQQKFMEQ 315
28 TIC1825_V2       IQQKFMEQ 315
30 TIC1825_V3       IQQKFMEQ 315
49 TIC1825_12       IQQKFMEQ 283
51 TIC1825_13       IQQKFMEQ 283
53 TIC1825_15       IQQKFMEQ 283
32 TIC2463_3        VQHKNI-- 282
34 TIC2463_4        VQHKNI-- 281
57 TIC2463_8        VQHKNI-- 313
59 TIC2463_9        VQHKNI-- 313
61 TIC2463_10       VQHKNI-- 313
36 TIC2463_Ts-Wx    VQHKNI-- 355
38 TIC2463_Ts-CR88  VQHKNI-- 341
```

*FIG. 1E*

PESTICIDAL TOXIN PROTEINS ACTIVE AGAINST COLEOPTERAN INSECTS

CROSS REFERENCE TO RELATED APPLICATION

This application claims priority to U.S. Provisional Application Ser. No. 61/971,855 filed Mar. 28, 2014, which is incorporated into this application by reference in its entirety.

INCORPORATION OF SEQUENCE LISTING

The file named "38_21_59428_ST25.txt" containing a computer readable form of the Sequence Listing was created on Mar. 25, 2015. This file is 135,562 bytes (as measured in the MS-Windows® operating system), is contemporaneously filed by electronic submission (using the United States Patent Office EFS-Web filing system), and is incorporated into this application by reference in its entirety.

FIELD OF THE INVENTION

The invention generally relates to the field of insect inhibitory toxin proteins. A novel class of proteins exhibiting insect inhibitory activity against agriculturally-relevant pests of crop plants and seeds are disclosed. In particular, the disclosed class of proteins is insecticidally active against agriculturally-relevant pests of crop plants and seeds, particularly the Coleopteran order of insect pests. Plants, plant parts, and seed containing a polynucleotide construct encoding one or more of the toxin proteins are provided.

BACKGROUND OF THE INVENTION

*Bacillus thuringiensis* ("Bt") strains are rich sources of insect inhibitory toxin proteins. These proteins can be used to control agriculturally-relevant pests of crop plants by spraying formulations containing these proteins onto plants or by expressing these proteins in plants and seeds. Notably, only a few toxic proteins are currently used commercially for controlling insects of the order Coleoptera, such as corn rootworms. Such currently deployed toxic proteins include Cry3Bb1, a modified Cry3A, eCry3.1Ab, and a binary toxin Cry34Ab1/Cry35Ab1 (requiring two different proteins for toxic activity). These proteins are effective for controlling *Diabrotica* species that infest corn roots, whether deployed singly, or in various combinations to decrease the likelihood of the development of resistance. Even though these proteins have been successfully deployed as insect control agents in transgenic crop plants, resistance to their effects can develop.

Resistance to a deployed toxin, whether chemistry or protein, is more likely to develop in a number of situations which enhance resistance development. Generally, the development of resistance is directly dependent on the length of time that a toxin is deployed into the environment. Resistance development is also more likely to increase in situations in which the dose of the toxin is insufficient to ensure mortality to the pest consuming a single bite of tissue containing the toxin. Accordingly, it is crucial to deliver a lethal dose of toxin with each bite, otherwise development of resistance to a particular toxin is more likely to occur. Repetitive use of the same toxin within a common geographic region on or in multiple species of plants which are susceptible to the same or similar pests within a common geographic region is more likely to cause rapid development of resistance to the toxin, particularly in climates in which there are multiple generations of a particular target pest within a single growing season. Geographic regions that are nearer to the equator tend to have longer and more consistent photoperiods and climates conducive for plant growth and cultivation, and the pests in these regions tend to have multiple generations in shorter periods of time than in other locations which are exposed to more dramatic climate changes that reduce the number of reproductive cycles that are encountered in similar periods of time. For all the forgoing reasons, dependence on a limited number of toxic proteins or toxic chemistries can result in the development of resistance to these pest control agents.

Other proteins disclosed in the art that are asserted to exhibit toxic effects to corn rootworms include patatin, TIC100/101 binary toxin, ET33/34 binary toxin, TIC863, ET80/76 binary toxin, ET70, Cry3Bb (U.S. Pat. No. 6,501,009), Cry1C variants, Cry3A variants, Cry3, Cry3B, Cry34/35, 5307, Axmi184, Axmi205, AxmiR1, TIC901, TIC1201, TIC407, TIC417, TIC431, TIC807, TIC853, TIC3131, DIG-10, eHIPs (U.S. Patent Application Publication No. 2010/0017914), and ω-Hexatoxin-Hv1a (U.S. Patent Application Publication US2014-0366227 A1). These proteins may be provided alone or in combinations with other toxic agents in subsequent commercial embodiments to insure durability of the rootworm resistant product and to decrease the likelihood of resistance development. However, none of these additional proteins have been observed to provide the low dose toxic effect against corn rootworms that the currently deployed commercial toxin proteins exhibit, and so have not been recognized to be commercially useful.

Accordingly, there is a need in the art for the discovery, development, and commercial deployment of new toxic agents, particularly environmentally friendly, highly selective and specific toxin proteins or chemistries that are active when used either alone or in various combinations with one or more supplementary toxic agents against a broad spectrum of insect pest species, particularly those pest species—such as Coleopteran species—that have been observed to develop resistance to currently deployed toxins.

SUMMARY OF THE INVENTION

Insect inhibitory toxin proteins (i.e., TIC2463 related toxin proteins) are provided herein that are derived from various *Bacillus* species including from *Bacillus thuringiensis* ("Bt") which exhibit surprising low dose efficacy against one or more Coleopteran plant pests, including but not limited to Colorado potato beetle and corn rootworm larvae. The toxin proteins of the present invention each exhibit substantial amino acid sequence percent identity to each other and can each be used alone or in combinations with the other proteins of the named genus of protein toxins in various formulations to be applied to the surfaces of plants and seeds or by expressing these proteins in plants and seeds to control target Coleopteran pests.

TIC2463-related toxin proteins can be expressed in planta from recombinant DNA constructs designed for expression in plants to achieve the production of transgenic plants that are embodied with the ability to resist Coleopteran insect pest infestation as a result of the expression of pesticidally effective amounts of the toxin proteins disclosed herein within relevant cells and tissues of the transgenic plant. These proteins can be used alone or in combinations with each other and with other toxic proteins and toxic agents in formulations and in planta, thus providing alternatives to known Coleopteran toxic proteins and insecticide chemistries currently in use in agricultural systems.

Recombinant nucleic acid molecules are provided for expression of the TIC2463-related toxin proteins disclosed herein. In one embodiment a recombinant nucleic acid molecule is provided that comprises (i.e., contains at least) a heterologous promoter operably linked to a polynucleotide segment having a nucleotide sequence that encodes at least one TIC2463-related protein toxic portion. Nucleotide sequences encoding TIC2463-related protein toxic portions disclosed herein include those set forth in each of the following SEQ ID numbers: SEQ ID NO:1 from position 100-945, SEQ ID NO:3 from position 100-939, SEQ ID NO:5 from position 85-1011, SEQ ID NO:7 from position 94-948, SEQ ID NO:9 from position 79-978, SEQ ID NO:11 from position 100-942, SEQ ID NO:13 from position 100-939, SEQ ID NO:15 from position 100-939, SEQ ID NO:17 from position 85-1011, SEQ ID NO:19 from position 85-1011, SEQ ID NO:21 from position 79-978, SEQ ID NO:23 from position 79-978, SEQ ID NO:25 from position 100-963, SEQ ID NO:27 from position 100-963, SEQ ID NO:29 from position 100-963, SEQ ID NO:31 from position 1-846, SEQ ID NO:33 from position 1-843, SEQ ID NO:35 from position 226-1065, SEQ ID NO:37 from position 187-1023, SEQ ID NO:39 from position 1-846, SEQ ID NO:41 from position 100-939 and having any codon other than TAA, TAG, or TGA occupying position 781-783, SEQ ID NO:43 from position 100-945, SEQ ID NO:44 from position 100-939, SEQ ID NO:45 from position 85-1011, SEQ ID NO:46 from position 94-948, SEQ ID NO:47 from position 79-978, SEQ ID NO: 48 from position 1-852, SEQ ID NO: 50 from position 1-852, SEQ ID NO: 52 from position 1-852, SEQ ID NO: 54 from position 1-933, SEQ ID NO: 56 from position 100-939, SEQ ID NO: 58 from position 100-939 and SEQ ID NO: 60 from position 100-939.

Constructs for expressing each such TIC2463-related toxin protein will typically include at least a heterologous promoter operably linked to a polynucleotide segment encoding the pesticidal polypeptide. In certain constructs, the pesticidal polypeptide will have an amino terminal segment of amino acids corresponding to an applicable signal peptide for secretion of the toxin portion of the TIC2463-related protein into a subcellular compartment (for example, import into a plant organelle such as a chloroplast, plastid, mitochondria, or amyloplast) or alternatively a signal peptide useful in bacterial systems for secretion out of the bacterial cytoplasm and into the periplasm (in the case of gram negative bacteria) or into the extracellular space. The pesticidal polypeptide expressed from the nucleotide sequences described herein will contain at least the mature amino acid sequence set forth in one of each of the following: the amino acid sequence as set forth in SEQ ID NO:2 from amino acid position 34-315, SEQ ID NO:4 from amino acid position 34-313, SEQ ID NO:6 from amino acid position 29-337, SEQ ID NO:8 from amino acid position 34-316, SEQ ID NO:10 from amino acid position 27-326, SEQ ID NO:12 from amino acid position 34-314, SEQ ID NO:14 from amino acid position 34-313, SEQ ID NO:16 from amino acid position 34-313, SEQ ID NO:18 from amino acid position 29-337, SEQ ID NO:20 from amino acid position 29-337, SEQ ID NO:22 from amino acid position 27-326, SEQ ID NO:24 from amino acid position 27-326, SEQ ID NO:26 from amino acid position 34-321, SEQ ID NO:28 from amino acid position 34-321, SEQ ID NO:30 from amino acid position 34-321; SEQ ID NO:32 from amino acid position 1-282; SEQ ID NO:34 from amino acid position 1-281; SEQ ID NO:36 from amino acid position 76-355; SEQ ID NO:38 from amino acid position 62-341; SEQ ID NO:49 from amino acid position 1-283; SEQ ID NO:51 from amino acid position 1-283; SEQ ID NO:53 from amino acid position 1-283; SEQ ID NO:55 from amino acid position 1-310; SEQ ID NO:57 from amino acid position 34-313; SEQ ID NO:59 from amino acid position 34-313 and SEQ ID NO:61 from amino acid position 34-313. Reference to mature amino acid sequences is intended to mean that the protein is expressed from a nucleotide sequence that encodes a precursor protein, i.e., a protein that contains the mature segment as well as an operably linked N-terminal amino acid segment exhibiting from about 25 to about 35 amino acids in length (in the case of a bacterial or yeast expression system) or from about 25 to about 80 amino acids in length (in the case of a plant or yeast expression system). The N terminal segment is required for targeting the mature toxin portion of the related protein to the periplasm or extracellular space (with reference to a bacterial or yeast expression system) or to a subcellular compartment such as a mitochondria, chloroplast, plastid, vacuole, or amyloplast (in the case of a plant or yeast expression system, as applicable).

The proteins described herein will be expressed from a construct that contains at least a heterologous promoter (a promoter not naturally associated with the native toxin coding sequence) operably linked to a polynucleotide segment encoding the pesticidal polypeptide. The pesticidal polypeptide will contain an amino acid sequence having at least 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 or about 100% amino acid sequence identity to the amino acid sequence as set forth in any of SEQ ID NO:2, 4, 6, 8, 10, 12, 14, 16, 18, 20, 22, 24, 26, 28, 30, 32, 34, 36, 38, 49, 51, 53, 55, 57, 59 and 61. The heterologous promoter can be a native Bt promoter obtained from the 5' end of any of the open reading frames ("ORFs") of the present invention for expression in a *Bacillus* host cell.

Polynucleotide segments described herein encoding a TIC2463-related toxin will hybridize to any other polynucleotide segment that encodes any other TIC2463-related toxins. Hybridization methods using the polynucleotide sequences described herein are useful for detecting bacterial strains harboring TIC2463 related toxin coding sequences and for detecting cloned DNA segments that contain all or a portion of an open reading frame encoding a TIC2463-related toxin protein. Hybridization or hybridize is intended to mean the non-covalent bonding of two different polynucleotide molecules by reverse complement alignment, whether DNA to DNA, RNA to RNA, or DNA to RNA, under stringent hybridization conditions. The two polynucleotide molecules that hybridize to each other will each have a nucleotide sequence exhibiting at least about 50% identity to each other along the length of the hybridized portion. The molecules described herein corresponding to *Bacillus* sequences are particularly useful for detecting and identifying other closely or distantly related TIC2463-related toxin protein family members. Hybridization conditions that are particularly useful include hybridization for 4 to 12 hours in 50% formamide, 1 M NaCl, and 1% SDS at about 37° C., and a wash in 0.1×SSC at a temperature of from about 60° C. to about 65° C.

Recombinant nucleic acid molecules described herein may have a nucleotide sequence that optionally:

a) is a synthetic sequence that has been designed for expression in a plant;

b) is selected from the group consisting of SEQ ID NO: 1, 3, 5, 7, 9, 11, 13, 15, 17, 19, 21, 23, 25, 27, 29, 31, 33, 35, 37, 43, 44, 45, 46, 47, 48, 50, 52, 54, 56, 58 and 60;

c) is expressed in a plant cell; or d) further comprises a nucleotide sequence encoding a heterologous polypeptide.

Recombinant nucleic acid molecules described herein may be present within a host cell (a transgenic, recombinant, or transformed host cell, i.e., a cell that does not naturally contain such recombinant nucleic acid molecule). The host cell is intended to include, but not be limited to, a bacterial host cell, a fungal host cell, and a plant host cell. The plant host cell is typically present within a plant, a plant tissue such as the xylem, phloem, leaf, stem, flower or flower part (including pistil, stamen, petal, ovum or pollen or the equivalent thereof), root, or seed. The plant, plant tissue or seed is intended to include, but not be limited to, maize, sorghum, wheat, cabbage, sunflower, tomato, crucifer, pepper, potato, cotton, rice, soybean, sugarbeet, sugarcane, tobacco, barley, any fruit or vegetable, any seed or nut producing plant, and oilseed rape (canola).

A TIC2463-related polypeptide will exhibit pesticidal activity. The polypeptide will preferably exhibit the mature amino acid sequence as set forth in each of the sequences of SEQ ID NO:2, 4, 6, 8, 10, 12, 14, 16, 18, 20, 22, 24, 26, 28, 30, 32, 34, 36, 38, 49, 51, 53, 55, 57, 59 and 61 or will exhibit at least from about 44 to about 99 or even about 100% amino acid sequence identity to any of these representative amino acid sequences. The mature segment of amino acids is exemplified in the following segments: SEQ ID NO:2 from amino acid position 34-315, SEQ ID NO:4 from amino acid position 34-313, SEQ ID NO:6 from amino acid position 29-337, SEQ ID NO:8 from amino acid position 34-316, SEQ ID NO:10 from amino acid position 27-326, SEQ ID NO:12 from amino acid position 34-314, SEQ ID NO:14 from amino acid position 34-313, SEQ ID NO:16 from amino acid position 34-313, SEQ ID NO:18 from amino acid position 29-337, SEQ ID NO:20 from amino acid position 29-337, SEQ ID NO:22 from amino acid position 27-326, SEQ ID NO:24 from amino acid position 27-326, SEQ ID NO:26 from amino acid position 34-321, SEQ ID NO:28 from amino acid position 34-321, SEQ ID NO:30 from amino acid position 34-321; SEQ ID NO:32 from amino acid position 1-282; SEQ ID NO:34 from amino acid position 1-281; SEQ ID NO:36 from amino acid position 76-355; SEQ ID NO:38 from amino acid position 62-341, SEQ ID NO:49 from amino acid position 1-283, SEQ ID NO:51 from amino acid position 1-283, SEQ ID NO:53 from amino acid position 1-283, SEQ ID NO:55 from amino acid position 1-310, SEQ ID NO:57 from amino acid position 34-313, SEQ ID NO:59 from amino acid position 34-313 and SEQ ID NO:61 from amino acid position 34-313.

The recombinant TIC2463-related polypeptide may contain heterologous amino acid sequences, i.e., sequences that are not naturally present within the TIC2463-related protein. For example, a TIC2463-related toxin protein may be modified to contain amino acids that are conserved relative to amino acid positions naturally present within the protein sequence. The skilled artisan will understand the allowed substitutions and is able to test for the ability of a particular protein to withstand such substitutions without compromising the toxic properties of the TIC2463 related toxin protein. Multiple TIC2463-related toxin proteins may be accessed and aligned to construct a chimera made up of parts of two or more different TIC2463 related toxin proteins. For example, a portion of TIC2463 (SEQ ID NO:4) may be substituted with the corresponding portion of TIC1825 (SEQ ID NO:2), as determined by alignment of the two different proteins, resulting in a chimeric protein that exhibits the same or improved toxic properties relative to the original proteins from which the parts were derived.

Compositions comprising the TIC2463-related toxin proteins or variants thereof are contemplated. Such compositions may be formulated into a powder, dust, pellet, granule, spray, emulsion, colloid, or solution, each in an agriculturally acceptable formulation for topical application to a plant, plant part, soil, or for use as a seed coating or seed treatment. The composition may be prepared by desiccation, lyophilization, homogenization, extraction, filtration, centrifugation, sedimentation, or concentration of a culture of bacterial cells expressing the recombinant TIC2463 or related protein. Such bacterial cells include, but may not be limited to, root colonizing bacteria such as *Agrobacterium* or *Rhizobium* species, various *Bacillus* species including *Bacillus thuringiensis, Bacillus cereus*, and the like, *E. coli* and the like. It may also be possible to produce such compositions in yeast or insect cell culture systems such as *Pichia pastorus, Saccharomyces cerevisea* or *Spodoptera frugiperda*. Such compositions will contain from about 1% to about 99% by weight of the TIC2463 related toxin protein.

Methods for controlling Coleopteran pest populations using the TIC2463-related toxin proteins are provided. Each such method relies upon contacting the targeted Coleopteran pest with an insecticidally/pesticidally effective amount of the toxin protein. Typically the contacting step will be providing the effective amount of toxin protein in a diet provided to the pest either in the form of an artificial diet to which the toxin protein has been overlayed or into which the toxin protein has been intermixed. Alternatively, the diet can be a plant expressing a pesticidally effective amount of the toxin protein. The cells of the plant will be ingested by the target pest. Preferably a single bite of the diet will be sufficient to cause morbidity, mortality, fecundicity, or stunting of the target pest.

Methods are provided for producing TIC2463-related toxin proteins. Typically a host cell transformed to contain a construct encoding the precursor TIC2463 or related protein is obtained and cultured under conditions conducive for the expression and accumulation of sufficient quantities of the toxin protein. The toxin protein may accumulate in the host cell or may be secreted into the extracellular space surrounding the host cell. In any event, the toxin protein so produced can be captured and formulated as is or purified from the host cell or from the culture medium using methods known in the art. The purified toxin protein or precursor may then be used as a sample in various diet compositions and at various concentrations in comparison to other toxin proteins or toxic agents, for comparison to other TIC2463 related toxic proteins, and among other things, for generation of antibody or similar reagents used for specific binding (such as antibodies, antibody binding fragments (f-Ab's), lectins, lipocalins, anticalins, alphabodies, and the like).

Transgenic or recombinant plants are provided which have DNA constructs encoding one or more of the TIC2463-related toxin proteins of the present invention stably incorporated into the plant genome or into a plant chloroplast genome. Such plants exhibit the trait of Coleopteran pest resistance. Seed from such plants can be increased, so long as such seed also contain the particular DNA construct encoding the TIC2463 or related toxin protein, and such increased seed can be used in breeding programs to introgress the Coleopteran resistance trait into other varieties/ germplasm of similar plants, cross by breeding such plants and seeds with other transgenic plants of the same variety containing other recombinant traits such as additional Coleopteran resistance traits (for example, resistance to corn rootworms or Colorado potato beetles, flea beetles, weevils, wire worms, and the like), Lepidopteran resistance traits, Hemipteran and Homopteran resistance traits, nematode resistance traits, fungal resistance traits, herbicide tolerance traits such as tolerance to dicamba, glyphosate, basta, glufosinate, 2,4-D, and the like, and yield and stress, water use, nitrogen use efficiency, and other transgenic traits known in the art.

Such plants are protected from Coleopteran insect pest infestation and can be combined by breeding with different transgenic events containing other traits. Alternatively, other traits can be included as additional DNA constructs in a vector linked to the construct containing the TIC2463 related toxin protein coding segment (i.e., vector stacked or linked traits), facilitating the decreased cost and increased efficiency for breeding purposes.

Chemical agents toxic to Coleopteran species and protein toxic agents different from the TIC2463 related toxic proteins can be employed in various combinations, both in and ex planta, with the proteins described herein. A chemical agent may be selected from the group consisting of an organochloride, an organophosphate, a carbamate, a pyrethroid, a neonicotinoid, a ryanoid, and a dsRNA molecule targeting a specific gene for suppression in the plant pest targeted for control. A protein toxic agent may be selected from the group consisting of patatin, TIC100/101 binary toxin, ET33/34 binary toxin, TIC863, ET80/76 binary toxin, ET70, Cry3Bb (U.S. Pat. No. 6,501,009), Cry1C variants, Cry3A variants, Cry3, Cry3B, Cry34/35, 5307, Axmi184, Axmi205, AxmiR1, TIC901, TIC1201, TIC407, TIC417, TIC431, TIC807, TIC853, TIC3131, DIG-10, eHIPs, and ω-Hexatoxin-Hv1a toxin proteins and a Cry protein toxin used to control a Lepidopteran or Hemipteran plant pest.

A method for increasing the yield of a crop of seed, fruit, berries, nuts, vegetables, oil or lint produced from a plant is specifically contemplated herein. Any such method includes at least growing a plant in a field. Generally, the plant includes a DNA construct stably incorporated into the genome of the cells of the plant. The construct encodes a pesticidal protein that contains at least an amino acid sequence selected from the group consisting of the amino acid sequence as set forth in SEQ ID NO:2 from amino acid position 34-315, SEQ ID NO:4 from amino acid position 34-313, SEQ ID NO:6 from amino acid position 29-337, SEQ ID NO:8 from amino acid position 34-316, SEQ ID NO:10 from amino acid position 27-326, SEQ ID NO:12 from amino acid position 34-314, SEQ ID NO:14 from amino acid position 34-313, SEQ ID NO:16 from amino acid position 34-313, SEQ ID NO:18 from amino acid position 29-337, SEQ ID NO:20 from amino acid position 29-337, SEQ ID NO:22 from amino acid position 27-326, SEQ ID NO:24 from amino acid position 27-326, SEQ ID NO:26 from amino acid position 34-321, SEQ ID NO:28 from amino acid position 34-321, SEQ ID NO:30 from amino acid position 34-321, SEQ ID NO:32 from amino acid position 1-282, SEQ ID NO:34 from amino acid position 1-281, SEQ ID NO:36 from amino acid position 76-355, SEQ ID NO:38 from amino acid position 62-341, SEQ ID NO:49 from amino acid position 1-283, SEQ ID NO:51 from amino acid position 1-283, SEQ ID NO:53 from amino acid position 1-283, SEQ ID NO:55 from amino acid position 1-310, SEQ ID NO:57 from amino acid position 34-313, SEQ ID NO:59 from amino acid position 34-313 and SEQ ID NO:61 from amino acid position 34-313. The TIC2463-related toxin protein exhibits at least from about 44% to about 100% amino acid sequence identity to any of the mature toxin proteins set forth in SEQ ID NO's 2, 4, 6, 8, 10, 12, 14, 16, 18, 20, 22, 24, 26, 28, 30, 32, 34, 36, 38, 49, 51, 53, 55, 57, 59 and 61. A plant grown under such conditions is ideally exposed to a field infested with a pest against which the TIC2463-related toxin protein has pesticidal activity and such plants are protected from infestation.

Also provided herein are recombinant insecticidal polypeptides comprising at least 50%, 60%, 70%, 75%, 80%, 90%, 95%, 97%, or 99% identity to SEQ ID NO: 4 and further comprising at least about 1.5, 2, 3, 4, 5, 6, 10, 15, 25, or 50 times higher insecticidal activity in a diet bioassay compared to TIC2463, patatin, TIC100/101 binary toxin, ET33/34 binary toxin, TIC863, ET80/76 binary toxin, ET70, Cry3Bb, Cry1C variants, Cry3A variants, Cry3, Cry3B, Cry34/35, 5307, Axmi184, Axmi205, AxmiR1, TIC901, TIC1201, TIC407, TIC417, TIC431, TIC807, TIC853, TIC3131, DIG-10, eHIPs, or ω-Hexatoxin-Hv1a. In some aspects, these recombinant insecticidal polypeptides comprise insecticidal activity against a Coleopteran species. In some aspects, the insecticidal activity of these recombinant insecticidal polypeptides is measured by $LC_{50}$ referred to as the lethal concentration of an insecticidal polypeptide causing 50% mortality of a target insect in a diet bioassay. In other aspects, the insecticidal activity of these recombinant insecticidal polypeptides is measured by $MIC_{50}$ referred to as the concentration of an insecticidal polypeptide causing 50% inhibition of target insect molting in a diet bioassay.

Further provided herein are recombinant insecticidal polypeptides comprising at least 50%, 60%, 70%, 75%, 80%, 90%, 95%, 97% or 99% identity to SEQ ID NO: 4 and further comprising in-planta insecticidal activity equal to or higher than the in-planta insecticidal activity of TIC2463, patatin, TIC100/101 binary toxin, ET33/34 binary toxin, TIC863, ET80/76 binary toxin, ET70, Cry3Bb, Cry1C variants, Cry3A variants, Cry3, Cry3B, Cry34/35, 5307, Axmi184, Axmi205, AxmiR1, TIC901, TIC1201, TIC407, TIC417, TIC431, TIC807, TIC853, TIC3131, DIG-10, eHIPs, or ω-Hexatoxin-Hv1a. Also provided herein are insecticidal compositions comprising any one or more of the forgoing recombinant insecticidal polypeptides.

Also provided herein are recombinant nucleic acid molecules comprising a heterologous promoter operably linked to a polynucleotide encoding a first insecticidal polypeptide comprising at least 50%, 60%, 70%, 75%, 80%, 90%, 95%, 97%, or 99% identity to SEQ ID NO: 4 and further comprising at least about 1.5, 2, 3, 4, 5, 6, 10, 15, 25, or 50 times higher insecticidal activity in a diet bioassay compared to TIC2463, patatin, TIC100/101 binary toxin, ET33/34 binary toxin, TIC863, ET80/76 binary toxin, ET70, Cry3Bb, Cry1C variants, Cry3A variants, Cry3, Cry3B, Cry34/35, 5307, Axmi184, Axmi205, AxmiR1, TIC901, TIC1201, TIC407, TIC417, TIC431, TIC807, TIC853, TIC3131, DIG-10, eHIPs, or ω-Hexatoxin-Hv1a. In some aspects, these recombinant nucleic acid molecules are codon-optimized for in-planta expression. Further provided are plants or part thereof comprising one or more forgoing recombinant nucleic acid molecules. In some aspects, insecticidal polypeptides are targeted to chloroplasts of these plants. In other aspects, these plants or part thereof, comprise two or more insecticidal polypeptides having different modes of action or further comprise a dsRNA capable of suppressing an essential gene in a Coleopteran species. In one aspect, insecticidal polypeptides and dsRNAs comprised in plants disclosed herein are toxic to a same Coleopteran species. In another aspect, insecticidal polypeptides and dsRNAs comprised in plants disclosed herein are toxic to different Coleopteran species.

BRIEF DESCRIPTION OF THE DRAWINGS

FIG. 1 (including five panels: FIG. 1A, FIG. 1B, FIG. 1C, FIG. 1D, and FIG. 1E) illustrates an amino acid sequence alignment of the TIC2463-related proteins, correlating the SEQ ID NO and the protein name with each specific amino acid sequence, and showing in bold characters in FIG. 1D the amino acids that are referred to in Example 3.

BRIEF DESCRIPTION OF THE SEQUENCES

SEQ ID NO:1 is a recombinant polynucleotide sequence obtained from a *Bacillus thuringiensis* species encoding a TIC1825 protein from an open reading frame at nucleotide position 1-945 and a translation termination codon.

SEQ ID NO:2 is the amino acid sequence translation of the TIC1825 protein from the open reading frame as set forth in SEQ ID NO:1.

SEQ ID NO:3 is a recombinant polynucleotide sequence obtained from a *Bacillus thuringiensis* species encoding a TIC2463 protein from an open reading frame at nucleotide position 1-939 and a translation termination codon.

SEQ ID NO:4 is the amino acid sequence translation of the TIC2463 protein from the open reading frame as set forth in SEQ ID NO:3.

SEQ ID NO:5 is a recombinant polynucleotide sequence obtained from a *Bacillus thuringiensis* species encoding a TIC2461 protein from an open reading frame at nucleotide position 1-1011 and a translation termination codon.

SEQ ID NO:6 is the amino acid sequence translation of the TIC2461 protein from the open reading frame as set forth in SEQ ID NO:5.

SEQ ID NO:7 is a recombinant polynucleotide sequence obtained from a *Bacillus thuringiensis* species encoding a TIC3037 protein from an open reading frame at nucleotide position 1-948 and a translation termination codon.

SEQ ID NO:8 is the amino acid sequence translation of the TIC3037 protein from the open reading frame as set forth in SEQ ID NO:7.

SEQ ID NO:9 is a recombinant polynucleotide sequence obtained from a *Bacillus thuringiensis* species encoding a TIC2228 protein from an open reading frame at nucleotide position 1-978 and a translation termination codon.

SEQ ID NO:10 is the amino acid sequence translation of the TIC2228 protein from the open reading frame as set forth in SEQ ID NO:9.

SEQ ID NO:11 is a recombinant polynucleotide sequence obtained from a *Bacillus thuringiensis* species encoding a TIC3005 protein from an open reading frame at nucleotide position 1-942 and a translation termination codon.

SEQ ID NO:12 is the amino acid sequence translation of the TIC3005 protein from the open reading frame as set forth in SEQ ID NO: 11.

SEQ ID NO:13 is a recombinant polynucleotide sequence obtained from a *Bacillus thuringiensis* species encoding a TIC2593 protein from an open reading frame at nucleotide position 1-939 and a translation termination codon.

SEQ ID NO:14 is the amino acid sequence translation of the TIC2593 protein from the open reading frame as set forth in SEQ ID NO:13.

SEQ ID NO:15 is a recombinant polynucleotide sequence obtained from a *Bacillus thuringiensis* species encoding a TIC2598 protein from an open reading frame at nucleotide position 1-939 and a translation termination codon.

SEQ ID NO:16 is the amino acid sequence translation of the TIC2598 protein from the open reading frame as set forth in SEQ ID NO:15.

SEQ ID NO:17 is a recombinant polynucleotide sequence obtained from a *Bacillus thuringiensis* species encoding a TIC3891 protein from an open reading frame at nucleotide position 1-1011 and a translation termination codon.

SEQ ID NO:18 is the amino acid sequence translation of the TIC3891 protein from the open reading frame as set forth in SEQ ID NO:17.

SEQ ID NO:19 is a recombinant polynucleotide sequence obtained from a *Bacillus thuringiensis* species encoding a TIC3090 protein from an open reading frame at nucleotide position 1-1011 and a translation termination codon.

SEQ ID NO:20 is the amino acid sequence translation of the TIC3090 protein from the open reading frame as set forth in SEQ ID NO:19.

SEQ ID NO:21 is a recombinant polynucleotide sequence obtained from a *Bacillus thuringiensis* species encoding a TIC3626 protein from an open reading frame at nucleotide position 1-978 and a translation termination codon.

SEQ ID NO:22 is the amino acid sequence translation of the TIC3626 protein from the open reading frame as set forth in SEQ ID NO:21.

SEQ ID NO:23 is a recombinant polynucleotide sequence obtained from a *Bacillus thuringiensis* species encoding a TIC2081 protein from an open reading frame at nucleotide position 1-978 and a translation termination codon.

SEQ ID NO:24 is the amino acid sequence translation of the TIC2081 protein from the open reading frame as set forth in SEQ ID NO:23.

SEQ ID NO:25 is a polynucleotide sequence encoding an amino acid sequence variant of the TIC1825 amino acid sequence set forth in SEQ ID NO:2.

SEQ ID NO:26 is the amino acid sequence translation of the TIC1825 variant protein from the open reading frame as set forth in SEQ ID NO:25.

SEQ ID NO:27 is a polynucleotide sequence encoding an amino acid sequence variant of the TIC1825 amino acid sequence set forth in SEQ ID NO:2.

SEQ ID NO:28 is the amino acid sequence translation of the TIC1825 variant protein from the open reading frame as set forth in SEQ ID NO:27.

SEQ ID NO:29 is a polynucleotide sequence encoding an amino acid sequence variant of the TIC1825 amino acid sequence set forth in SEQ ID NO:2.

SEQ ID NO:30 is the amino acid sequence translation of the TIC1825 variant protein from the open reading frame as set forth in SEQ ID NO:29.

SEQ ID NO:31 is a polynucleotide sequence encoding an amino acid sequence variant of the TIC2463 amino acid sequence set forth in SEQ ID NO:4.

SEQ ID NO:32 is the amino acid sequence translation of the TIC2463 variant protein from the open reading frame as set forth in SEQ ID NO:31.

SEQ ID NO:33 is a polynucleotide sequence encoding an amino acid sequence variant of the TIC2463 amino acid sequence set forth in SEQ ID NO:4.

SEQ ID NO:34 is the amino acid sequence translation of the TIC2463 variant protein from the open reading frame as set forth in SEQ ID NO:33.

SEQ ID NO:35 is a polynucleotide sequence encoding an amyloplast target peptide from an open reading frame at nucleotide position 1-225, and a synthetic nucleotide sequence encoding a TIC2463 protein, from an open reading frame at nucleotide position 226-1065.

SEQ ID NO:36 is the amino acid sequence translation of the target peptide and TIC2463 protein from the open reading frame as set forth in SEQ ID NO:35.

SEQ ID NO:37 is a polynucleotide sequence encoding a chloroplast target peptide from an open reading frame at nucleotide position 1-183, and a synthetic nucleotide sequence encoding a TIC2463 protein, from an open reading frame at nucleotide position 184-1023.

SEQ ID NO:38 is the amino acid sequence translation of the target peptide and TIC2463 protein from the open reading frame as set forth in SEQ ID NO:37.

SEQ ID NO:39 is a recombinant polynucleotide sequence obtained from a *Bacillus thuringiensis* species encoding a TIC1373 protein from an open reading frame at nucleotide position 1-846 and a translation termination codon.

SEQ ID NO:40 is the amino acid sequence translation of the TIC1373 protein from the open reading frame as set forth in SEQ ID NO:39.

SEQ ID NO:41 is a recombinant polynucleotide sequence obtained from a *Bacillus cereus* species encoding a WP_000699779 protein from an open reading frame at nucleotide position 1-780 and a translation termination codon.

SEQ ID NO:42 is the amino acid sequence translation of the WP_000699779 protein from the open reading frame as set forth in SEQ ID NO:41.

SEQ ID NO:43 is a synthetic nucleotide sequence encoding a TIC1825 protein.

SEQ ID NO:44 is a synthetic nucleotide sequence encoding a TIC2463 protein.

SEQ ID NO:45 is a synthetic nucleotide sequence encoding a TIC2461 protein.

SEQ ID NO:46 is a synthetic nucleotide sequence encoding a TIC3037 protein.

SEQ ID NO:47 is a synthetic nucleotide sequence encoding a TIC2228 protein.

SEQ ID NO:48 is a synthetic polynucleotide sequence encoding an amino acid sequence variant of the TIC1825 amino acid sequence set forth in SEQ ID NO:2.

SEQ ID NO:49 is the amino acid sequence translation of the TIC1825 variant protein from the open reading frame as set forth in SEQ ID NO:48.

SEQ ID NO:50 is a synthetic polynucleotide sequence encoding an amino acid sequence variant of the TIC1825 amino acid sequence set forth in SEQ ID NO:2.

SEQ ID NO:51 is the amino acid sequence translation of the TIC1825 variant protein from the open reading frame as set forth in SEQ ID NO:50.

SEQ ID NO:52 is a synthetic polynucleotide sequence encoding an amino acid sequence variant of the TIC1825 amino acid sequence set forth in SEQ ID NO:2.

SEQ ID NO:53 is the amino acid sequence translation of the TIC1825 variant protein from the open reading frame as set forth in SEQ ID NO:52.

SEQ ID NO:54 is a synthetic polynucleotide sequence encoding an amino acid sequence variant of the TIC2461 amino acid sequence set forth in SEQ ID NO:6.

SEQ ID NO:55 is the amino acid sequence translation of the TIC2461 variant protein from the open reading frame as set forth in SEQ ID NO:54.

SEQ ID NO:56 is a synthetic polynucleotide sequence encoding an amino acid sequence variant of the TIC2463 amino acid sequence set forth in SEQ ID NO:4.

SEQ ID NO:57 is the amino acid sequence translation of the TIC2463 variant protein from the open reading frame as set forth in SEQ ID NO:56.

SEQ ID NO:58 is a synthetic polynucleotide sequence encoding an amino acid sequence variant of the TIC2463 amino acid sequence set forth in SEQ ID NO:4.

SEQ ID NO:59 is the amino acid sequence translation of the TIC2463 variant protein from the open reading frame as set forth in SEQ ID NO:58.

SEQ ID NO:60 is a synthetic polynucleotide sequence encoding an amino acid sequence variant of the TIC2463 amino acid sequence set forth in SEQ ID NO:4.

SEQ ID NO:61 is the amino acid sequence translation of the TIC2463 variant protein from the open reading frame as set forth in SEQ ID NO:60.

DETAILED DESCRIPTION OF THE INVENTION

The problem in the art of agricultural pest control can be characterized as a need for new toxin proteins that are efficacious against target pests, exhibit broad spectrum toxicity against target pest species, are capable of being expressed in plants without causing undesirable agronomic issues, and provide an alternative mode of action compared to current toxins that are used commercially in plants. Novel pesticidal proteins exemplified by TIC2463 are disclosed in this application, and address each of these needs, particularly against a broad spectrum of Coleopteran insect pests, and more particularly against corn rootworm pest species.

The family of proteins disclosed and claimed in this application were identified from bacterial strains that exhibited insecticidal activity. Genomic libraries of such bacterial strains were created in vectors from which clones were identified that recover the insecticidal activity observed in the naturally occurring bacterial strain when such clones are introduced into acrystalliferous strains of *Bacillus thuringiensis*. The DNA of such clones was sequenced and used to identify one or more open reading frames (ORFs) encoding the suspected insecticidal protein(s). The DNA sequence of such ORFs from other bacterial sources was used to probe for the presence of similar ORFs in other bacterial strains. The identification of similar ORFs led to the discovery of additional DNA sequences encoding similar proteins also exhibiting Coleopteran toxic activity.

As described further in this application, a *Bacillus thuringiensis* (Bt) strain that exhibited insecticidal activity, strain EG3957, was identified. A library constructed from the genome of this strain resulted in the identification of a clone that contained an ORF encoding a novel Bt protein, TIC1373 (SEQ ID:40). The TIC1373 amino acid sequence exhibited a distant relationship (less than 29% amino acid sequence identity) to known Bt insecticidal toxins referred to as Cry60 and Cry15Aa1, proteins which are known to exhibit only mosquitocidal activity. It was hypothesized that this distant relationship of TIC1373 (SEQ ID NO:40) to the Cry60 and Cry15 pfam was suggestive that insecticidal activity may be observed from the expression of the TIC1373 peptide from a plasmid containing a Bt sporulation promoter directing the expression of the TIC1373 open reading frame in an acrystalliferous strain of *Bacillus thuringiensis.*

The resulting recombinant strain failed to exhibit any insecticidal activity when tested in bioassay against a battery of plant pests, and a protein corresponding to the mass of the predicted TIC1373 was not detected in the culture supernatant or spore/cell pellet. The predicted amino acid sequence of TIC1373 is substantially identical to an uncharacterized protein known in the prior art as NCBI WP_003308447, first published on the NCBI website in 2009 and referenced in Zwick, et al. (*Genome Res.* 22:1512-1524 (2012)).

The distant relationship of the TIC1373 protein sequence to the ETX/MTX type toxin Cry60 suggested that the TIC1373 protein may exhibit some unusual or difficult to characterize pesticidal activity. However, as explained above, the TIC1373 peptide did not exhibit pesticidal activity against any insect tested in a battery of insect bioassays, including tests against Coleopteran, Lepidopteran and Hemipteran pest species. It was hypothesized that proteins related to the TIC1373 peptide may be present in other microbial strains and the variations present within the amino acid sequences of related proteins may result in toxin activity. Therefore, the TIC1373 protein coding sequence was used to identify other microbial strains that contained related sequences homologous to the predicted TIC1373 protein. Such homologues were cloned and sequenced and ORFs encoding proteins resembling the TIC1373 protein were identified.

One additional homologous protein that was identified is set forth in SEQ ID NO:2, designated herein as TIC1825. The sequence encoding TIC1825, as set forth in SEQ ID NO:1, was obtained from Bt strain EG5015. The predicted TIC1825 protein amino acid sequence exhibited substantial identity to TIC1373 (77% identity across the length of the TIC1373 protein). Surprisingly, TIC1825 contained an additional 31 N-terminal amino acids compared to the TIC1373 protein. Expression of the TIC1825 protein from an acrystalliferous strain of *Bacillus thuringiensis* surprisingly exhibited Coleopteran insecticidal activity in the cell pellet as well as in the culture supernatant, suggesting that the protein toxin may be secreted into the culture medium.

TIC1825 protein was collected from the culture supernatant and an N-terminal amino acid sequence analysis of the protein indicated that the TIC1825 protein predicted from the TIC1825 gene ORF was a precursor protein that contained a 33 amino acid signal peptide that was likely responsible for targeting the nascent TIC1825 protein for secretion into the culture supernatant when expressed in the acrystalliferous strain of *Bacillus thuringiensis*. It was determined that the full length TIC1825 open reading frame (SEQ ID NO:1 from nucleotide position 1-945) encoded a toxin precursor protein that is processed into a mature toxin protein encoded by nucleotides 100-945. The secreted protein amino terminal sequence information, combined with the fact that the ORF encoded an N-terminal peptide segment not present in the secreted form of the protein, suggested that the predicted amino terminal peptide segment is a thirty three (33) amino acid secretory signal peptide encoded by nucleotides 1-99 as set forth in SEQ ID NO:1.

Based on the TIC1825 data, additional sequence information was obtained from Bt strain EG3957 from which TIC1373 was identified. It was determined that additional sequence information existed upstream of the original TIC1373 clone that contained a sequence encoding an N-terminal amino acid segment similar to the N-terminal signal peptide segment encoded by the TIC1825 coding sequence. Assembly of an artificial coding sequence comprising nucleotides 1-99 of TIC1825 operably linked in frame to the TIC1373 coding sequence resulted in an ORF encoding TIC2463 (SEQ ID NO:4). Surprisingly, expression of a clone containing the ORF encoding TIC2463 (SEQ ID NO:3 from nucleotide position 1 through 939) resulted in insecticidal activity toxic to Coleopteran species, present both in the culture supernatant as well as partially retained within the cell pellet of the acrystalliferous Bt culture.

The information that a secretion signal may be required for recovering biological activity of this class of protein toxins allowed a broader search of *Bacillus* strains for the presence of additional DNA segments encoding proteins homologous to TIC1825 as well as to TIC2463. Bt strains were identified that contained such homologous sequences by probing their respective genomes with the TIC2463 and TIC1825 coding sequences, and cloned DNA segments were obtained corresponding to these homologous sequences. Each of these additional clones were sequenced to determine the presence of open reading frames, and the predicted protein translations from these open reading frames identified proteins exhibiting structural features similar to those of the TIC1825 and TIC2463 proteins. A Coleopteran toxin family of proteins was thus discovered including TIC1825 (SEQ ID NO:2), TIC2463 (SEQ ID NO:4), TIC2461 (SEQ ID NO:6), TIC3037 (SEQ ID NO:8), TIC2228 (SEQ ID NO:10), TIC3005 (SEQ ID NO:12), TIC2593 (SEQ ID NO:14), TIC2598 (SEQ ID NO:16), TIC3891 (SEQ ID NO:18), TIC3090 (SEQ ID NO:20), TIC3626 (SEQ ID NO:22), and TIC2081 (SEQ ID NO:24). Each of these proteins exhibits Coleopteran toxic activity against one or more Coleopteran pests.

Any novel pesticidal protein or insect inhibitory protein, that comprises, that consists of, that is substantially homologous to, that is similar to, or that is derived from these proteins are referred to herein collectively as TIC2463-related toxic proteins, and alternatively as the TIC2463-related protein toxin class or family, the TIC2463-related toxin proteins, the TIC2463-related protein genus, toxin proteins related to the TIC2463-toxin protein, proteins related to TIC2463, TIC2463-related toxin polypeptides, TIC2463-related pesticidal proteins, and the like; each reference having substantially the same meaning. The TIC2463-related protein toxin class includes TIC1825 (SEQ ID NO:2), TIC2463 (SEQ ID NO: 4), TIC2461 (SEQ ID NO:6), TIC3037 (SEQ ID NO:8), TIC2228 (SEQ ID NO:10), TIC3005 (SEQ ID NO:12), TIC2593 (SEQ ID NO:14), TIC2598 (SEQ ID NO:16), TIC3891 (SEQ ID NO:18), TIC3090 (SEQ ID NO:20), TIC3626 (SEQ ID NO:22), and TIC2081 (SEQ ID NO:24), pesticidal or insect inhibitory segments thereof, combinations thereof, or variants thereof (such as the variants disclosed in this application), that confer activity against Coleopteran pests, including any protein exhibiting pesticidal or insect inhibitory activity if alignment of such protein with a TIC2463-related protein results in amino acid sequence identity of any fraction percentage from about 34% to about 100% percent, when compared to any of the TIC2463-related proteins. The TIC2463-related proteins include the precursor forms as well as the mature length forms of the proteins. The novel proteins disclosed herein are summarized in Example 1 and in Table 1 (1-A and 1-B) and in Table 2.

Comparison of the amino acid sequences of these various toxin protein family members to proteins known in the art identified only two uncharacterized amino acid segments predicted from publicly disclosed nucleotide sequence information. The first segment is the uncharacterized NCBI protein referenced above, WP_003308447, which is substantially identical to TIC1373 (SEQ ID NO:40) and is encoded by the DNA segment set forth in SEQ ID NO:39. As disclosed in this application, attempts to express the amino acid segment (SEQ ID NO:40, TIC1373) encoded from position 1-846 as set forth in SEQ ID NO:39 from a construct operably linked to a heterologous promoter functional in *Bacillus* species in an acrystalliferous strain of *Bacillus thuringiensis* did not detect any protein expressed from this open reading frame, and no insecticidal activity was detected against Coleopteran species such as Colorado potato beetle or corn rootworm larvae in culture supernatants or in cell/spore pellets in in vitro bioassays. However, producing a construct linking the TIC1373 reading frame from nucleotide position 7-846 as set forth in SEQ ID NO:39 to a DNA segment encoding a signal peptide derived from any one of the TIC2463-related toxin proteins described herein (for example, SEQ ID NO:1, SEQ ID NO:3, SEQ ID NO:11, SEQ ID NO:13, and SEQ ID NO:15 from nucleotide position 1-99; SEQ ID NO:5, SEQ ID NO:17 and SEQ ID NO:19 from nucleotide position 1-84; SEQ ID NO:7 from nucleotide position 1-93; and SEQ ID NO:9, SEQ ID NO:21 and SEQ ID NO:23 from nucleotide position 1-78), and expression of that construct in an acrystalliferous strain of *Bacillus thuringiensis*, surprisingly results in insecticidal bioactivity of the TIC1373 protein segment as set forth in SEQ ID NO:40 from amino acid position 3 through amino acid position 282. This peptide segment is identical to the corresponding segment as set forth in SEQ ID NO:4 (TIC2463). The data described in the Examples indicates that secretion of the toxin portion of this family of proteins is obligatory in order for the mature secreted form of the toxin protein to exhibit insecticidal activity, regardless of whether the protein is being expressed in planta or within a bacterial host cell.

The second uncharacterized amino acid segment (SEQ ID NO:42) is predicted from an open reading frame as set forth in SEQ ID NO:41. The predicted segment of amino acids as set forth in SEQ ID NO:42 is derived from a *Bacillus cereus* bacterium, and is encoded by a cryptic sequence that contains a termination codon at nucleotide position 781-783 as set forth in SEQ ID NO:41 (TAA) which predicts that the encoded protein will contain an amino acid sequence identical to the sequence set forth in SEQ ID NO:4 (TIC2463) from amino acid position 1 through 260. However, the amino acid segment set forth at SEQ ID NO:42, translated from the open reading frame set forth in SEQ ID NO:41 from nucleotide position 1-780, fails to encode amino acids 261 through 313 as set forth in SEQ ID NO:4 (TIC2463). It is therefore unlikely that this predicted truncated/cryptic protein would exhibit any insecticidal activity.

The proteins described in this application are related to each other by: (a) source or origin (i.e., from *Bacillus* species of bacteria, and in particular, within Bt strains of bacteria); (b) biological activity characterized as pesticidal activity against Coleopteran insect pest species; (c) structural features absent in other proteins in the art which can be used as query sequences for identification of other members of the genus; (d) amino acid sequence length; (e) the presence of an N-terminal amino acid segment that functions at least as a signal polypeptide for use in a nascent amino acid chain for secretion of the toxin segment into the extracellular space or to the surface of the *Bacillus* (referred to variously herein as a signal amino acid sequence, signal sequence, signal peptide, or signal polypeptide, each term referring to substantially the same or a similar or related structure); and (f) the presence of a mature polypeptide (referred to variously herein as a mature polypeptide amino acid sequence, a mature toxin segment, mature polypeptide, or mature protein; each term referring substantially to the same or a similar or related structure), serving as the active form of the toxin when secreted to the surface of, or to the extracellular space surrounding, the *Bacillus*.

The full-length and mature proteins of the TIC2463-related protein toxin class can also be related by primary structure (conserved amino acid motifs), by length (about 295 amino acids for the mature proteins and about 320 amino acids for the full-length proteins) and by other characteristics. The full-length proteins from the present invention have a mass of about 35 k-Daltons and the mature proteins have a mass of about 32 k-Daltons. Characteristics of the full-length and mature forms of the TIC2463-related protein toxin class are reported in Tables 1-A and 1-B.

TABLE 1-A

Characteristics of Full-length Protein

| Protein | Molecular Weight (in Daltons) | Amino Acid Length | Isoelectric Point | Charge at PH 7.0 | No. of Strongly Basic (−) Amino Acids | No. of Strongly Acidic Amino Acids | No. of Hydrophobic Amino Acids | No. of Polar Amino Acids |
|---|---|---|---|---|---|---|---|---|
| TIC1825 | 34934.55 | 315 | 9.026 | 5.570 | 36 | 31 | 98 | 109 |
| TIC2463 | 34673.14 | 313 | 8.941 | 4.571 | 33 | 29 | 103 | 111 |
| TIC2461 | 37536.90 | 337 | 8.345 | 2.548 | 36 | 34 | 97 | 136 |
| TIC3037 | 35609.06 | 316 | 7.928 | 1.215 | 40 | 39 | 91 | 109 |
| TIC2228 | 36375.75 | 326 | 9.055 | 5.247 | 35 | 30 | 89 | 136 |
| TIC3005 | 34628.39 | 314 | 9.378 | 10.368 | 37 | 27 | 102 | 108 |
| TIC2593 | 34687.17 | 313 | 8.941 | 4.573 | 33 | 29 | 103 | 111 |
| TIC2598 | 34727.32 | 313 | 9.061 | 5.570 | 33 | 28 | 105 | 109 |
| TIC3891 | 37354.72 | 337 | 5.829 | −2.612 | 34 | 37 | 103 | 130 |
| TIC3090 | 37336.76 | 337 | 6.185 | −1.611 | 34 | 36 | 104 | 131 |
| TIC3626 | 36382.78 | 326 | 8.918 | 4.575 | 34 | 30 | 90 | 133 |
| TIC2018 | 36328.74 | 326 | 9.056 | 5.411 | 34 | 29 | 91 | 134 |

TABLE 1-B

| Characteristics of Mature Protein | | | | | | | | |
|---|---|---|---|---|---|---|---|---|
| Protein | Molecular Weight (in Daltons) | Amino Acid Length | Iso-electric Point | Charge at PH 7.0 | No. of Strongly Basic Amino Acids | No. of Strongly Acidic Amino Acids | No. of Hydro-phobic Amino Acids | No. of Polar Amino Acids |
| TIC1825 | 31387.27 | 282 | 8.516 | 2.573 | 33 | 31 | 83 | 99 |
| TIC2463 | 31034.70 | 280 | 8.137 | 1.574 | 30 | 29 | 87 | 102 |
| TIC2461 | 34370.06 | 309 | 7.409 | 0.580 | 33 | 33 | 84 | 127 |
| TIC3037 | 32292.03 | 285 | 5.553 | −2.750 | 36 | 39 | 78 | 99 |
| TIC2228 | 33683.49 | 300 | 8.530 | 2.249 | 32 | 30 | 77 | 127 |
| TIC3005 | 30951.80 | 281 | 8.995 | 5.373 | 32 | 27 | 88 | 100 |
| TIC2593 | 31048.73 | 280 | 8.137 | 1.576 | 30 | 29 | 87 | 102 |
| TIC2598 | 31118.91 | 280 | 8.549 | 2.573 | 30 | 28 | 88 | 101 |
| TIC3891 | 34296.97 | 309 | 5.167 | −5.577 | 31 | 37 | 90 | 1120 |
| TIC3090 | 34279.01 | 309 | 5.310 | −4.576 | 31 | 36 | 91 | 121 |
| TIC3626 | 33690.53 | 300 | 8.117 | 1.577 | 31 | 30 | 78 | 124 |
| TIC2081 | 33636.48 | 300 | 8.532 | 2.413 | 31 | 29 | 79 | 125 |

It is noted in this application that nucleotide segments encoding only the mature toxin segment of a TIC2463 or related toxin protein have not been found to be useful in producing pesticidally effective amounts of the toxin component. Pesticidally effective amounts of the toxin are produced only when the mature toxin segment is operably linked to a secretion signal peptide and targeted for secretion (in bacterial systems) or targeted for insertion into subcellular compartments when expressed within plant cells (for example, targeting to a chloroplast or plastid structure using a chloroplast or plastid targeting peptide or targeting the mature toxin segment to another subcellular compartment such as an amyloplast or mitochondrial structure). Expression of any of the toxin segments of the present invention from a nucleotide segment encoding a signal peptide (for bacterial expression purposes) or a targeting peptide (for plant subcellular compartment localization purposes) linked to and in frame with the mature toxin segment provides pesticidally effective amounts of the toxin component.

Based on the data presented in this application, and without being bound by any theory, a TIC2463-related toxin may need to be expressed from a gene or DNA construct that provides for a precursor or pro-form polypeptide that is subsequently processed to release a toxin segment from the precursor form of the protein. Proteases within a particular host cell will likely be present that function to cause this release by cleaving the signal peptide segment from the mature toxin segment. In some embodiments, it may be necessary to provide an engineered cleavage site between the mature toxin segment and the targeting peptide. To the extent that the precursor form of a particular toxin of the present invention is provided to a pest, a protease in the target pest may be required to cleave the precursor form at the engineered cleavage site, releasing the activated toxin segment. In other embodiments, the precursor form would be expressed within a particular host cell and one or more enzymes within the host cell would be active in cleaving the N-terminal amino acid segment from the mature toxin segment. In each case, the release of the mature toxin segment from the N-terminal secretion or targeting segment would activate the mature toxin segment, resulting in a fully functional toxin protein that exhibits Coleopteran pest inhibitory activity.

Cleavage of the signal sequence can be mediated by agents which include, but are not limited to, chemical agents and proteolytic enzymes. Some of these enzymes may be present in the target pest digestive system, for example, enzymes present within a host cell that cleave the precursor protein as the nascent precursor is being translated from mRNA within the host cell, or as the precursor is being translocated across one or more membranes within the host cell as secretion of the mature form of the toxin protein is facilitated.

Reference in this application to the terms "active" or "activity", "pesticidal activity" or "pesticidal" or "insecticidal activity", "insect inhibitory" or "insecticidal" refer to efficacy of a toxic agent, such as a protein toxin, in inhibiting (inhibiting growth, feeding, fecundity, or viability), suppressing (suppressing growth, feeding, fecundity, or viability), controlling (controlling the pest infestation, controlling the pest feeding activities on a particular crop containing an effective amount of a TIC2463-related protein) or killing (causing the morbidity, mortality, or reduced fecundity of) a pest. These terms are intended to include the result of providing a pesticidally effective amount of a toxic protein to a pest where the exposure of the pest to the toxic protein results in morbidity, mortality, reduced fecundity, or stunting. These terms also include repulsion of the pest from the plant, a tissue of the plant, a plant part, seed, plant cells, or from the particular geographic location where the plant may be growing, as a result of providing a pesticidally effective amount of the toxic protein in or on the plant. In general, pesticidal activity refers to the ability of a toxic protein to be effective in inhibiting the growth, development, viability, feeding behavior, mating behavior, fecundity, or any measurable decrease in the adverse effects caused by an insect feeding on this protein, protein fragment, protein segment or polynucleotide of a particular target pest, including but not limited to insects of the order Coleoptera. The toxic protein can be produced by the plant or can be applied to the plant or to the environment within the location where the plant is located. The terms "bioactivity", "effective", "efficacious" or variations thereof are also terms interchangeably utilized in this application to describe the effects of proteins of the present invention on target insect pests.

A pesticidally effective amount of a toxic agent, when provided to a target pest, exhibits pesticidal activity when the toxic agent contacts the pest. The toxic agent can be a pesticidal protein or one or more chemical agents known in the art. Insecticidal chemical agents and insecticidal protein agents can be used alone or in combination with each other. Chemical agents include, but are not limited to, organochlorides, organophosphates and carbamates, pyrethroids, neonicotinoids, ryanoids, and dsRNA molecules targeting specific genes for suppression in a target pest. Insecticidal protein agents include the protein toxins set forth in this application, as well as other proteinaceous toxic agents that target the same pest as the TIC2463 related toxin protein. Such other proteinaceous toxic agents include, but are not intended to be limited to, patatin, TIC100/101 binary toxin, ET33/34 binary toxin, TIC863, ET80/76 binary toxin, ET70, Cry3Bb (U.S. Pat. No. 6,501,009), Cry1C variants, Cry3A variants, Cry3, Cry3B, Cry34/35, 5307, Axmi184, Axmi205, AxmiR1, TIC901, TIC1201, TIC407, TIC417, TIC431, TIC807, TIC853, TIC3131, DIG-10, eHIPs, and ω-Hexatoxin-Hv1a toxin proteins.

It is intended that reference to a pest, particularly a pest of a crop plant, means insect pests of crop plants, particularly those that are controlled by a protein from the TIC2463-related protein toxin class, but can also include other pests such as Lepidopteran, Hemipteran, Homopteran or Thysanopteran insect pests of plants, as well as nematodes and fungi, when toxic agents targeting these pests are ω-localized or present together with a TIC2463-related toxin protein or a protein toxin that is about 34 to 100 percent identical to a TIC2463-related toxin protein.

Further, reference in this application to an "isolated DNA molecule", or an equivalent term or phrase, is intended to mean that the DNA molecule is one that is present alone or in combination with other compositions, but not within its natural environment. For example, nucleic acid elements such as a coding sequence, intron sequence, untranslated leader sequence, promoter sequence, transcriptional termination sequence, and the like, that are naturally found within the DNA of the genome of an organism are not considered to be "isolated" so long as the element is within the genome of the organism and at the location within the genome in which it is naturally found. However, each of these elements, and subparts of these elements, would be "isolated" within the scope of this disclosure so long as the element is not within the genome of the organism and at the location within the genome in which it is naturally found. Similarly, a nucleotide sequence encoding a insecticidal protein or any naturally occurring insecticidal variant of that protein would be an isolated nucleotide sequence so long as the nucleotide sequence was not within the DNA of the bacterium from which the sequence encoding the protein is naturally found. A synthetic nucleotide sequence encoding the amino acid sequence of the naturally occurring insecticidal protein would be considered to be isolated for the purposes of this disclosure. For the purposes of this disclosure, any transgenic nucleotide sequence, i.e., the nucleotide sequence of the DNA inserted into the genome of the cells of a plant or bacterium, or present in an extra-chromosomal vector would be considered to be an isolated nucleotide sequence whether it is present within the plasmid or similar structure used to transform the cells, within the genome of the plant or bacterium, or present in detectable amounts in tissues, progeny, biological samples or commodity products derived from the plant or bacterium.

The TIC2463-related proteins and polypeptides are related by primary structure, including but not limited to the number of amino acid identities along a particular length of linked amino acids forming a particular protein segment, the percent amino acid sequence identity of a first protein segment (the subject) relative to the amino acid sequence of a second protein segment (the query), the length in amino acids of a particular first protein segment compared to the length in amino acids of a second protein segment, or any combination thereof.

The term "segment" or "fragment" is used in this application to describe consecutive amino acid or nucleic acid sequences that are shorter than the complete amino acid or nucleic acid sequence describing a TIC2463-related protein. A segment or fragment exhibiting insect inhibitory activity is also disclosed in this application if alignment of such segment or fragment, with the corresponding section of a TIC2463-related protein, results in amino acid sequence identity of any fraction percentage from about 34 to about 100 percent between the segment or fragment and the corresponding section of the TIC2463-related protein.

Proteins that resemble the TIC2463-related proteins can be identified by comparison to each other using various computer-based algorithms known in the art. Amino acid identities reported in this application are a result of a Clustal W alignment using these default parameters: Weight matrix: blosum, Gap opening penalty: 10.0, Gap extension penalty: 0.05, Hydrophilic gaps: On, Hydrophilic residues: GPSNDQERK, Residue-specific gap penalties: On (Thompson, et al (1994) Nucleic Acids Research, 22:4673-4680). Percent amino acid identity is further calculated by determining a quotient obtained as a result of dividing a number representing the amino acid identities between the a query and a subject protein by the length of the subject protein, then multiplying the quotient so obtained by 100. It should be understood that use of this algorithm is not limiting and that alternative alignment algorithms known to those of ordinary skill in the art are also contemplated.

It is intended that a protein exhibiting insect inhibitory activity against a Coleopteran insect species is related to a TIC2463-related protein if the protein is used in a query, e.g., in a Clustal W alignment, and at least one of the proteins of the present invention are identified as hits in such alignment in which the query protein exhibits amino acid identity along the length of the TIC2463-related protein that is about 34%, 35%, 40%, 50%, 60%, 70%, 75%, 76%, 77%, 78%, 79%, 80%, 81%, 82%, 83%, 84%, 85%, 85%, 87%, 88%, 89%, 90%, 91%, 92%, 93%, 94%, 95%, 96%, 97%, 98%, 99%, 100%, or any fraction percentage in this range.

Alignment of proteins described in this application with each other resulted in an amino acid sequence identity for each pair as represented by the matrix shown in Table 2. The vertical columns on the left side of Table 2 and the row across the top of the table list the individual proteins by both SEQ ID NO and TIC number. The relative percent amino acid sequence identity between two different proteins is reflected in the box where the respective row and column intersect. This representation shows that the TIC2463 family members are related to each other by percent identity ranging from as little as 44% identity to as much as 99-100% identity. These percent identities are shown relative to other full length proteins within this family group. Generally, the percent identity between proteins increases when only the toxin portion of the respective proteins are aligned.

TABLE 2

Pair-wise Matrix Display of TIC2463 Related Toxin Proteins by Percent Amino Acid Sequence Identity
SEQ ID NO/TIC Ref #

| SEQ ID NO/ TIC Ref # | 4/2463 | 40/1373 | 14/2593 | 16/2598 | 42/ | 2/1825 | 12/3005 | 20/3090 | 18/3891 | 6/2461 | 24/2081 | 10/2228 | 22/3626 | 8/3037 |
|---|---|---|---|---|---|---|---|---|---|---|---|---|---|---|
| 4/2463 | | 90.1 | 99.7 | 98.1 | 81.8 | 85.3 | 77.6 | 51.8 | 50.5 | 50.8 | 52.1 | 51.4 | 51.8 | 46.6 |
| 40/1373 | 100 | | 99.6 | 98.2 | 80.1 | 86.2 | 78.7 | 55.7 | 54.3 | 55.3 | 55.7 | 55 | 55.3 | 50 |
| 14/2593 | 99.7 | 89.8 | | 97.8 | 81.5 | 85 | 77.3 | 51.4 | 50.2 | 50.5 | 51.8 | 51.1 | 51.4 | 46.3 |
| 16/2598 | 98.1 | 88.5 | 97.8 | | 80.5 | 84 | 76.4 | 51.4 | 50.2 | 50.5 | 51.4 | 50.8 | 51.1 | 46.6 |
| 42/ | 98.5 | 86.9 | 98.1 | 96.9 | | 85.8 | 78.1 | 51.2 | 50 | 50.4 | 52.3 | 51.5 | 51.9 | 45.4 |
| 2/1825 | 84.8 | 77.1 | 84.4 | 83.5 | 70.8 | | 83.2 | 53.7 | 52.7 | 52.7 | 50.8 | 50.2 | 50.5 | 48.3 |
| 12/3005 | 77.4 | 70.7 | 77.1 | 76.1 | 64.6 | 83.4 | | 54.1 | 52.9 | 51.9 | 49.7 | 48.7 | 49.4 | 47.1 |
| 20/3090 | 48.1 | 46.6 | 47.8 | 47.8 | 39.5 | 50.1 | 50.4 | | 95 | 88.1 | 55.8 | 55.5 | 55.2 (186) | 57 |
| 18/3891 | 46.9 | 45.4 | 46.6 | 46.6 | 38.6 | 49.3 | 49.3 | 95 | | 89.3 | 55.5 | 54.9 | 54.9 | 57 |
| 6/2461 | 47.2 | 46.3 | 46.9 | 46.9 | 38.9 | 49.3 | 48.4 | 88.1 | 89.3 | | 55.5 | 54.9 | 55.2 | 55.5 |
| 24/2081 | 50 | 48.2 | 49.7 | 49.4 | 41.7 | 49.1 | 47.9 | 57.7 | 57.4 | 57.4 | | 96.6 | 96.9 | 54.6 |
| 10/2228 | 49.4 | 47.5 | 49.1 | 48.8 | 41.1 | 48.5 | 46.9 | 57.4 | 56. | 56.7 | 96.6 | | 95.4 | 53.4 |
| 22/3626 | 49.7 | 47.9 | 49.4 | 49.1 | 41.4 | 48.8 | 47.5 | 57.1 | 56.7 | 57.1 | 96.9 | 95.4 | | 53.7 |
| 8/3037 | 46.2 | 44.6 | 45.9 | 46.2 | 37.3 | 48.1 | 46.8 | 60.8 | 60.8 | 59.2 | 56.3 | 55.1 | 55.4 | |

TIC2463-related toxin protein family members are also related by the exhibition of a signal peptide sequence consisting of from about 27 or 28 amino acids to about 33 to 35 amino acids in length, primary structure (conserved amino acid motifs), by length (the toxin portion of the protein exhibits a length of from about 269 amino acids to about 315 amino acids; the signal peptides of these family members exhibit from about 65 to about 100 percent amino acid sequence identity to each other) and by other characteristics.

As indicated previously in this application, the native signal sequences of the TIC2463-related toxin proteins can be substituted for each other without sacrifice of the ability of the precursor protein, whether native or chimeric, to function when expressed in *Bacillus* strains of bacteria. In addition, the native signal sequence associated with any of the TIC2463-related toxin proteins can be substituted with a non-native sequence that facilitates import into the chloroplast or into an amyloplast within a plant host cell. Examples of signal peptides capable of targeting proteins to specific intracellular compartments, or which effect secretion or insertion into a membrane, or which effect modifications in post-translational processing, are known in the art. In one embodiment, the native signal peptide of TIC2463 is substituted with other signal peptide sequences. As set forth in SEQ ID NO:36 (from amino acid position 1-75), a plant amyloplast targeting peptide is covalently linked to the mature TIC2463 toxin segment consisting of amino acid position 76 through 355 (SEQ ID NO:36). As set forth in SEQ ID NO:38, a plant chloroplast or plastid targeting peptide from amino acid position 1-61 is linked covalently to the mature TIC2463 amino acid sequence from amino acid position 62 through 341. Each of these chimeric precursor proteins is efficiently expressed in plant host cells, plants, plant parts, and seed and the mature protein is localized to the respective subcellular compartment.

The TIC2463-related toxin proteins are related by common function and exhibit insect inhibitory activity against Coleopteran insect pests, including adults, pupae, larvae and neonates. The insects of the order Coleoptera include, but are not limited to, *Agrotis* spp., *Anthonomus* spp., *Atomaria linearis, Chaetocnema tibialis, Cosmopolites* spp., *Curculio* spp., *Dermestes* spp., *Diabrotica* spp., *Epilachna* spp., *Eremnus* spp., *Leptinotarsa decemlineata, Lissorhoptrus* spp., *Melolontha* spp., *Orycaephilus* spp., *Otiorhynchus* spp., *Phlyctinus* spp., *Popillia* spp., *Psylliodes* spp., *Rhizopertha* spp., *Scarabaeidae, Sitophilus* spp., *Sitotroga* spp., *Tenebrio* spp., *Tribolium* spp. and *Trogoderma* spp., particularly when the pest is *Diabrotica virgifera virgifera* (Western Corn Rootworm, WCR), *Diabrotica barberi* (Northern Corn Rootworm, NCR), *Diabrotica virgifera zeae* (Mexican Corn Rootworm, MCR), *Diabrotica balteata* (Brazilian Corn Rootworm, BZR), *Diabrotica undecimpunctata howardii* (Southern Corn Rootworm, SCR) and a Brazilian Corn Rootworm complex (BCR) consisting of *Diabrotica viridula* and *Diabrotica speciosa.*

It is contemplated that the proteins described in this application may exhibit toxic, insect pest controlling properties against insect species other than Coleopteran insects. For example, insects in the orders Lepidoptera, Hemiptera, Homoptera, Thysanoptera, and the like, are pests of plants and may be susceptible to these toxin proteins, particularly TIC2463-related proteins that are modified to exhibit an expanded host range. Such modifications may include deletion or insertion of one or more amino acids, amino acid substitutions, and construction of chimeric proteins using one or more segments from one member of the TIC2463-related protein family in combination with one or more applicable segments from any of the one or more other members of the TIC2463-related protein family, or in combination with one or more applicable segments from any other toxin protein known in the art to exhibit pest control properties (such as, for example, any Cry or Cyt protein family member exhibiting pesticidal bioactivity as recited on the Sussex University's life sciences website for *Bacillus thuringiensis* toxin nomenclature at Sussex.ac.uk/home/Neil_Crickmore/Bt/toxins2.html). The proteins of the present invention may be combined in a composition, including a plant, with one or more different toxic agents such as a dsRNA or different coleopteran toxic proteins to control corn rootworms or Colorado potato beetles, and with proteins other than coleopteran toxic proteins to control one or more pests from other insect orders including proteins such as Cry1's, Cry2's, Cry9's, TIC807 or derivatives thereof, TIC1415 and related proteins, and the like and with genes encoding tolerance to herbicides such as dicamba, glyphosate, glufosinate, 2,4-D and its derivatives, and the like.

This disclosure also contemplates the use of molecular methods known in the art to engineer and clone commercially useful proteins comprising chimeras of proteins from pesticidal proteins; e.g., the chimeras may be assembled from segments of TIC2463-related proteins to derive additional useful embodiments including assembly of segments of TIC2463-related proteins with segments of diverse proteins different from TIC2463-related proteins. The TIC2463 family of proteins can be subjected to alignment with each other and with other Bt pesticidal proteins (whether or not these are closely or distantly related phylogenetically), and segments of each such protein can be identified that can be useful for substitution, resulting in the construction of chimeric proteins. Such chimeric proteins can be subjected to pest bioassay analysis and characterized for the presence of increased bioactivity or expanded target pest spectrum compared to the parent proteins from which each such segment in the chimera was derived. The pesticidal activity of the polypeptides can be further engineered for improved activity to a particular pest or to a broader spectrum of pests by swapping domains or segments with other proteins, by amino acid substitution, deletion, or addition, or by using directed evolution methods known in the art.

Biologically functionally equivalent protein toxins are those that exhibit a substantial amino acid sequence identity to one or more of the TIC2463-related protein toxins and that exhibit substantially the same or the same or even greater pesticidal activity than the one or more protein(s) to which such comparison is made. Such functionally equivalent proteins include those with conservative amino acid substitutions and which exhibit no loss of function relative to the comparator protein. The skilled artisan will readily understand the term "conservative amino acid". Examples of proteins that can entertain substituted amino acids, segments of amino acids (such as substituted signal peptide sequences), or N- or C-terminal deletions to obtain biological equivalents include, but are not limited to, the protein sequence as set forth in any of: SEQ ID NO:2 (TIC1825), SEQ ID NO:4 (TIC2463), SEQ ID NO:6 (TIC2461), SEQ ID NO:8 (TIC3037), SEQ ID NO:10 (TIC2228), SEQ ID NO:12 (TIC3005), SEQ ID NO:14 (TIC2593), SEQ ID NO:16 (TIC2598), SEQ ID NO:18 (TIC3891), SEQ ID NO:20 (TIC3090), SEQ ID NO:22 (TIC3626), SEQ ID NO:24 (TIC2081), SEQ ID NO:26 (TIC1825_G233A, also referred to as TIC1825v1), SEQ ID NO:28 (TIC1825_P234A, also referred to as TIC1825v2), SEQ ID NO:30 (TIC1825_K224T_D226N_G233A_P234A_L246T_T248V, also referred to as TIC1825v3), SEQ ID NO:32 (TIC2463_3), SEQ ID NO:34 (TIC2463_4), SEQ ID NO:49 (TIC1825_12), SEQ ID NO:51 (TIC1825_13), SEQ ID NO:53 (TIC1825_15), SEQ ID NO:55 (TIC2461_5), SEQ ID NO:57 (TIC2463_8), SEQ ID NO:59 (TIC2463_9), SEQ ID NO:61 (TIC2463_10).

Methods are provided for discovering new members of the TIC2463-related protein class. The DNA sequence of any bacterial genome can be obtained and the data assembled into contiguous segments of sequence information. DNA sequences within the genome contigs can be identified to contain predicted ORFs encoding prospective protein sequences. The prospective encoded protein sequences can be compared to the proteins disclosed in this application as TIC2463-related toxin proteins, and the sequences encoding such prospective proteins can be cloned and expressed in any number of bacterial expression systems and the resulting protein expressed from such clones can be tested for pesticidal activity. Prospective proteins that exhibit insecticidal activity and that exhibit at least from about 44% to about 100% amino acid sequence identity to one or more of the proteins disclosed in this application are considered to be within the scope of the TIC2463-related toxin protein class. Alternatively, DNA segments consisting of from about 20 to about 900 nucleotides corresponding to the sequences set forth herein in any of SEQ ID NO:1, 3, 5, 7, 9, 11, 13, 15, 17, 19, 21 and 23 can be used as probes or primers for detecting or amplifying, as the case may be, DNA sequences from diverse bacterial species including *Bacillus* species. The detection of DNA sequences that hybridize to such probes, or the amplification of DNA segments using such primers in an applicable thermal amplification reaction, provides the skilled artisan with the materials for capturing the necessary segment(s) of DNA that can be assembled into a contiguous nucleotide sequence encoding an amino acid sequence that can be compared to the amino acid sequences of the proteins described in this application. Proteins discovered in this way can be tested for pesticidal activity. Proteins exhibiting pesticidal activity and that exhibit from about 44% or greater amino acid sequence identity to any of the TIC2463-related protein toxins disclosed in this application are TIC2463-related protein toxin members.

It is within the skill of the art to produce agents that bind specifically to one or more of the proteins described in this application (such as, for example, antibodies, alphabodies, lipocalins, anticalins, and the like). Such agents that bind specifically can be used to screen for and to find other members of the TIC2463 genus. The binding agents can be used to bind specifically to one or more of the TIC2463-related proteins or peptide fragments that may act as epitopes of the full length proteins disclosed in this application. The binding of the antibody, lipocalin, anticalin, alphabody, and the like can be detected by using methods similar to ELISA.

An embodiment of the invention includes recombinant polynucleotide compositions that encode for the TIC2463-related proteins. For example, the TIC2463-related proteins can be expressed from recombinant DNA constructs in which a polynucleotide molecule with the ORF encoding the protein is operably linked to elements such as a promoter and any other necessary regulatory elements functional for expression in the system or host cell type for which the construct is intended. Constructs designed for expression in plants containing a plant-functional promoter operably linked to a polynucleotide segment encoding a TIC2463-related protein are specifically contemplated. Other elements that may be useful in such constructs for use in plants include enhancers, introns, untranslated leader sequences, encoded protein immobilization tags (HIS-tag), encoded sub-cellular translocation peptides (e.g., plastid transit peptides, signal peptides), encoded polypeptide sites for post-translational modifying enzymes, ribosomal binding sites, and RNAi target sites, each operably linked to applicable regulatory or expression elements in each such construct.

By reference to "designed for expression in a plant", it is intended that nucleotide sequences obtained from a bacterial system or other host system that may encode a TIC2463 or a related protein may exhibit certain inimical sequences that have been shown to reduce the level of expression of the intended protein in a plant cell. Such embodiments and means for designing a gene to avoid such problem sequences are set forth in U.S. Pat. No. 5,500,365. While it is within the skill of the art to design a gene that avoids such problem sequences when viewing the '365 patent, hundreds or thousands or even millions of different sequences are possible that meet the criteria set forth in the '365 patent, and it is intended that each of these embodiments be included within the scope of this application in reference to a sequence encoding a TIC2463 or related protein designed for expression in a plant.

A recombinant DNA construct comprising a TIC2463-related protein encoding sequence can further comprise a region of DNA that encodes for one or more insect inhibitory agents which can be configured to concomitantly express or co-express with a DNA sequence encoding a TIC2463-related protein, an insect inhibitory dsRNA molecule, or an ancillary protein. Ancillary proteins include, but are not limited to, co-factors, enzymes, binding-partners, or other agents that function to aid in the effectiveness of an insect inhibitory agent, for example, by aiding its expression, influencing its stability in plants, optimizing free energy for oligomerization, augmenting its toxicity, and increasing its spectrum of activity. An ancillary protein may facilitate the uptake of one or more insect inhibitory agents, for example, or potentiate the toxic effects of the toxic agent.

A recombinant DNA construct can be assembled so that all proteins or RNA molecules are expressed from a single promoter or each protein or dsRNA molecule is under the control of a separate promoter or some combination thereof. The proteins of this application can be expressed from a multi-gene expression system in which one or more of the TIC2463-related proteins are expressed from a common nucleotide segment which also contains other ORFs and promoters, depending on the type of expression system selected. For example, a bacterial multi-gene expression system can utilize a single promoter to drive expression of multiply-linked/tandem ORFs from within a single operon. In another example, a plant multi-gene expression system can utilize multiply-linked expression cassettes, each cassette expressing a different protein or other agent such as one or more dsRNA molecules.

Recombinant polynucleotide or recombinant DNA constructs containing a nucleotide sequence encoding a TIC2463-related protein can be delivered to host cells by vectors, e.g., a plasmid, a baculovirus, an artificial chromosome, a virion, a cosmid, a phagemid, a phage or bacteriophage, or a viral vector. Such vectors can be used to achieve stable or transient expression of the TIC2463-related protein. Any such DNA construct introduced into a host cell is referred to as a "transgene" and the host cell recipient of the construct is a "transgenic cell" or "transgenic host cell".

Transgenic bacteria, plant cells, plants, and plant parts including flowers and flower parts and seed that contain any recombinant polynucleotide designed for expression of a TIC2463-related protein are specifically contemplated in this application. The term "bacterial cell" or "bacterium" is intended to include, but is not limited to, an *Agrobacterium*, a *Bacillus*, an *Escherichia*, a *Salmonella*, a *Pseudomonas*, or a *Rhizobium* cell. The term "plant cell" or "plant" can include, but is not limited to, an alfalfa, banana, barley, bean, broccoli, cabbage, brassica, carrot, cassava, castor, cauliflower, celery, chickpea, Chinese cabbage, citrus, coconut, coffee, corn, clover, cotton, a cucurbit, cucumber, Douglas fir, eggplant, eucalyptus, flax, garlic, grape, hops, leek, lettuce, Loblolly pine, millets, melons, nut, oat, olive, onion, ornamental, palm, pasture grass, pea, peanut, pepper, pigeonpea, pine, potato, poplar, pumpkin, Radiata pine, radish, rapeseed (Canola), rice, rootstocks, rye, safflower, shrub, sorghum, Southern pine, soybean, spinach, squash, strawberry, sugar beet, sugarcane, sunflower, sweet corn, sweet gum, sweet potato, switchgrass, tea, tobacco, tomato, triticale, turf grass, watermelon, and wheat plant cell or plant. Of particular interest are cotton, alfalfa, corn, soy, or sugarcane plants having enhanced pesticidal resistance against one or more insects of the Coleopteran order. Transgenic plants and transgenic plant parts regenerated from a transgenic plant cell containing a polynucleotide construct expressing a TIC2463-related toxin protein are provided. Transgenic plants can be obtained from a transgenic seed, by propagating, cutting, snapping, grinding or otherwise disassociating cells, parts, or tissue from the plant. The plant part can be a seed, a boll, a leaf, a flower or flower part, a stem, a root, a silk, a germ, or any portion thereof, or a non-regenerable portion of a transgenic plant part. As used in this context, a "non-regenerable" portion of a transgenic plant part is a portion that can not be induced to form a whole plant or that cannot be induced to form a whole plant that is capable of sexual and/or asexual reproduction. In certain embodiments, a non-regenerable portion of a plant part is a portion of a transgenic seed, boll, leaf, flower, stem, or root.

Methods of making transgenic plants that comprise insect or Coleoptera inhibitory amounts of a TIC2463-related protein are provided in this application. Such plants can be made by introducing a recombinant polynucleotide that encodes any of the TIC2463-related proteins into a plant cell and selecting a plant derived from the transformed plant cell that expresses an insect or Coleoptera-inhibitory amount of the TIC2463-related pesticidal protein. Plants can be derived from the plant cells by regeneration, seed, pollen, or meristem transformation techniques. Methods for transforming plants are known in the art (e.g., *Agrobacterium*-mediated transformation, biolistic methods and soaking or imbibition methods for introducing transgenic DNA into tissues). In certain embodiments, transgenic plants can have two or more constructs introduced independently into substantially the same position within the plant genome using site specific integration methods known in the art. Transgenic plants expressing one or more of the TIC2463 or related proteins of the present invention can be combined with any transgenic maize plant known in the art, by conventional breeding or by introducing by site directed insertion a construct expressing the protein of the present invention near the previously existing transgenic event, such previously existing transgenic events including but not being limited to Event 176, Event 4114, Event BT11, MIR162, MIR604, Event CBH-351, Event DAS-06275-8, Event DAS-59122-7, Event DBT418, Event MIR162, Event MIR604, Event MON810, Event MON863, Event MON88017, Event MON89034, and Event TC1507, or applicable combinations thereof.

Processed plant products are also provided which contain a detectable amount of one or more of the polynucleotides or proteins described herein, an insect inhibitory segment or fragment thereof, or any distinguishing portion thereof. The processed product is selected from the group consisting of plant biomass, oil, meal, animal feed, flour, flakes, bran, lint, hulls, and processed seed, and the product may be non-regenerable. A distinguishing portion thereof may include any one or more polypeptides of at least 10, 20, 30, 50, 100, 200, or even 250 contiguous amino acids as set forth in any of SEQ ID NO:2, 4, 6, 8, 10, 12, 14, 16, 18, 20, 22 and 24.

Processed plant products (also referred to as commodity products) wherein the processed product comprises a detectable amount of a TIC2463-related protein, a segment thereof, an insect inhibitory fragment thereof, or any distinguishing portion thereof, are also contemplated in this application. In certain embodiments, the processed product is selected from the group consisting of plant biomass, oil, meal, sugar, animal feed, flour, flakes, bran, lint, hulls, processed seed, and seed. The plant product can comprise commodity or other products of commerce derived from a transgenic plant or transgenic plant part, where the commodity or other products can be tracked through commerce by detecting nucleotide segments or expressed RNA or other proteins that encode or comprise distinguishing portions of a TIC2463-related protein. A "corn commodity product" is generally any part of a corn plant that is offered for commerce other than seed, as well as by-products of the grain or plant. Corn commodity products include but are not limited to vegetative material, grain or any partition of the grain. Examples can include, but are not limited to whole grain, dried distillers grains with solubles ("DDGS"), silage, stalks used e.g. for bedding, fuel or feed, corn oil, corn sugar, corn starch, ethanol, and other non-seed corn products and by-products known in the art.

Also provided in this application is the use of a transgenic plant that expresses an insect- or Coleoptera-inhibitory amount of one or more of the pesticidal proteins described herein to control an insect or Coleoptera infestation. Any of the aforementioned transgenic plants can be used in methods for protecting a plant from insect or Coleoptera infestation. Methods of obtaining transgenic plants that express Coleopteran-active proteins such as the TIC2463-related proteins are known in the art.

Transgenic plants which contain a recombinant polynucleotide sequence encoding and expressing one or more of the TIC2463-related toxin proteins described in this application: (i) exhibit enhanced traits as compared to a control plant; and (ii) produce transgenic seed and haploid pollen containing the recombinant polynucleotide sequence. Such plants with enhanced traits are identified by selection of transformed plants or progeny seed having the enhanced trait. For efficiency, a selection method is designed to evaluate multiple transgenic plants (events) comprising the recombinant DNA (for example, multiple plants from 2 to 20 or more transgenic events). Transgenic plants grown from transgenic seed provided in this application demonstrate enhanced traits. Reference to "enhanced traits" is intended to mean that a particular transgenic plant exhibits improvement in agronomic trait characteristics that contribute to increased pesticidal tolerance, or increased harvest yield (for example, increased amounts of a harvested crop, oil, carbohydrate, protein, fruit, berry, nut, grain, seed, or lint compared to plants lacking the recombinant polynucleotide sequence) or other traits that provide increased plant value, including, for example, improved seed, germ, oil, carbohydrate, protein, or commodity quality.

Methods are provided for producing plants and harvesting crops from seed comprising a recombinant polynucleotide molecule encoding a pesticidal polypeptide corresponding to the TIC2463-related toxin proteins are provided in this application. The method includes the steps of crossing by breeding an insect resistant first plant containing a construct for expression of a TIC2463-related protein with a second plant lacking any such construct, obtaining at least one progeny plant derived from the cross, and selecting progeny that express the requisite toxin protein. The progeny are resistant against one or more target insects susceptible to the TIC2463-related toxin protein. The steps of planting the seed to produce a crop from plants grown from the seed, and harvesting the crop (grain, fruit, berries, vegetables, carbohydrate, protein, oil, lint, and the like), are included in the method. At least about 50% of the grain harvested in any such crop is intended to contain the recombinant polynucleotide molecule.

Methods of controlling insects, particularly Coleopteran insects harmful to crop plants, with TIC2463-related proteins are also disclosed in this application. One method includes growing a plant containing an insect- or Coleopteran-inhibitory amount of a TIC2463-related protein and providing the plant in the diet of the target insect. In certain embodiments, such methods can further comprise any one or more of: (i) applying any composition comprising or encoding a TIC2463-related protein to the plant or a seed that gives rise to the plant; and (ii) transforming the plant or a plant cell that gives rise to the plant with a polynucleotide encoding a TIC2463-related protein. The plant may be transiently or stably transformed transgenic plant comprising a transgene that expresses an insect- or Coleopteran-inhibitory amount of a TIC2463-related protein. The plant may also be a non-transgenic plant to which a composition comprising a TIC2463-related protein has been applied. In one embodiment, the plant is a corn and the pest species is a Coleoptera species, particularly a *Diabrotica vergifera vergifera* or related species.

In certain embodiments, a recombinant nucleic acid molecule of the TIC2463-related proteins is the insecticidally active ingredient of an insect inhibitory composition prepared by culturing recombinant *Bacillus* or any other recombinant bacterial cell transformed to express a TIC2463-related toxin protein under conditions suitable to express the TIC2463-related toxin protein. Such a process can include preparation by desiccation, lyophilization, homogenization, extraction, filtration, centrifugation, sedimentation, or concentration of a culture of recombinant *Bacillus thuringiensis* cells expressing and producing the recombinant polypeptide. The process can result in a *Bacillus thuringiensis* cell extract, cell suspension, cell homogenate, cell lysate, cell supernatant, cell filtrate, or cell pellet. By obtaining the recombinant polypeptides and proteins so produced, a composition that includes the recombinant polypeptides and proteins can include bacterial cells, bacterial spores, and parasporal inclusion bodies and can be formulated for various uses, including agricultural pesticidal spray products or as insect inhibitory formulations in diet bioassays.

In one embodiment, to reduce the likelihood of resistance development, an insect inhibitory composition comprising a TIC2463-related protein can further comprise at least one additional polypeptide that exhibits insect inhibitory activity against the same Coleopteran insect species, but which is different from the TIC2463-related toxin protein. Possible additional polypeptides for such a composition include an insect inhibitory protein and an insect inhibitory dsRNA molecule. One example for the use of such ribonucleotide sequences to control insect pests is described in Baum, et al. (U.S. Patent Publication 2006/0021087 A1). Such additional polypeptide for the control of Coleopteran pests may be selected from the group consisting of an insect inhibitory protein, such as, but not limited to, patatin, TIC100/101 binary toxin, ET33/34 binary toxin, TIC863, ET80/76 binary toxin, ET70, Cry3Bb (U.S. Pat. No. 6,501,009), Cry1C variants, Cry3A variants, Cry3, Cry3B, Cry34/35, 5307, Axmi184, Axmi205, AxmiR1, TIC901, TIC1201, TIC407, TIC417, TIC431, TIC807, TIC853, TIC3131, DIG-10, eHIPs, and ω-Hexatoxin-Hv1a.

In other embodiments, such composition/formulation can further comprise at least one additional polypeptide that exhibits insect inhibitory activity to an insect that is not inhibited by an otherwise insect inhibitory protein of the present invention to expand the spectrum of insect inhibition obtained. For example, for the control of Lepidopteran pests, combinations of insect inhibitory proteins of the present invention can be used with an additional polypeptide for the control of Lepidopteran pests such as, but not limited to, Cry1A (U.S. Pat. No. 5,880,275), Cry1Ab, Cry1Ac, Cry1A.105, Cry1Ae, Cry1B (U.S. patent Publication Ser. No. 10/525,318), Cry1C (U.S. Pat. No. 6,033,874), Cry1D, Cry1Da and variants thereof, Cry1E, Cry1F, and Cry1A/F chimeras (U.S. Pat. Nos. 7,070,982; 6,962,705; and 6,713,063), Cry1G, Cry1H, Cry1I, Cry1J, Cry1K, Cry1L, Cry1-type chimeras such as, but not limited to, TIC836, TIC860, TIC867, TIC869 and TIC1100, Cry2A, Cry2Ab (U.S. Pat. No. 7,064,249), Cry2Ae, Cry4B, Cry6, Cry7, Cry8, Cry9, Cry15, Cry43A, Cry43B, Cry51Aa1, ET66, TIC400, TIC400, TIC800, TIC834, TIC1415, TIC3242, Vip3A, VIP3Ab, VIP3B, AXMI-184, AXMI-196, DIG-3, DIG-4, DIG-5, DIG-11, AfIP-1A and derivatives thereof (U.S. Patent Publication 2014-0033361 A1), AfIP-1B and derivatives thereof (U.S. Patent Publication 2014-0033361 A1), PIP-1APIP-1B (U.S. Patent Publication 2014-0007292 A1), PSEEN3174 (U.S. Patent Publication 2014-0007292 A1), AECFG-592740 (U.S. Patent Publication 2014-0007292 A1), Pput_1063 (U.S. Patent Publication 2014-0007292 A1), Pput_1064 (U.S. Patent Publication 2014-0007292 A1), GS-135 and derivatives thereof (U.S. Patent Publication 2012-0233726 A1), GS153 and derivatives thereof (U.S. Patent Publication 2012-0192310 A1), GS154 and derivatives thereof (U.S. Patent Publication 2012-0192310 A1), GS155 and derivatives thereof (U.S. Patent Publication 2012-0192310 A1), SEQ ID NO:2 and derivatives thereof as described in U.S. Patent Publication 2012-0167259 A1, SEQ ID NO:2 and derivatives thereof as described in U.S. Patent Publication 2012-0047606 A1, SEQ ID NO:2 and derivatives thereof as described in U.S. Patent Publication 2011-0154536 A1, SEQ ID NO:2 and derivatives thereof as described in U.S. Patent Publication 2011-0112013 A1, SEQ ID NO:2 and 4 and derivatives thereof as described in U.S. Patent Publication 2010-0192256 A1, SEQ ID NO:2 and derivatives thereof as described in U.S. Patent Publication 2010-0077507 A1, SEQ ID NO:2 and derivatives thereof as described in U.S. Patent Publication 2010-0077508 A1, SEQ ID NO:2 and derivatives thereof as described in U.S. Patent Publication 2009-0313721 A1, SEQ ID NO:2 or 4 and derivatives thereof as described in U.S. Patent Publication 2010-0269221 A1, SEQ ID NO:2 and derivatives thereof as described in U.S. Pat. No. 7,772,465 (B2), CF161_0085 and derivatives thereof as described in WO2014/008054 A2, Lepidopteran toxic proteins and their derivatives as described in US Patent Publications US2008-0172762 A1, US2011-0055968 A1, and US2012-0117690 A1; SEQ ID NO:2 and derivatives thereof as described in U.S. Pat. No. 7,510,878(B2), SEQ ID NO:2 and derivatives thereof as described in U.S. Pat. No. 7,812,129(B1); and the like. Further, for the control of Hemipteran pests, combinations of insect inhibitory proteins of the present invention can be used with Hemipteran-active proteins such as TIC1415 (US Patent Application Publication No. 2013/0097735), TIC807 (U.S. Pat. No. 8,609,936), and TIC834 (U.S. Patent Application Publication No. 2013/0269060). Additional polypeptides for the control of Coleopteran, Lepidopteran, and Hemipteran insect pests can be found on the *Bacillus thuringiensis* toxin nomenclature website maintained by Neil Crickmore (on the world wide web at btnomenclature.info).

The possibility for insects to develop resistance to certain insecticides has been documented in the art. One insect resistance management strategy is to employ transgenic crops that express two distinct insect inhibitory agents that operate through different modes of action. Therefore, any insects with resistance to either one of the insect inhibitory agents can be controlled by the other insect inhibitory agent. Another insect resistance management strategy employs the use of plants that are not protected to the targeted Coleopteran pest species to provide a refuge for such unprotected plants. One particular example is described in U.S. Pat. No. 6,551,962, which is incorporated by reference in its entirety.

Other embodiments such as topically applied pesticidal chemistries that are designed for controlling pests that are also controlled by the proteins disclosed herein to be used with proteins in seed treatments, spray on, drip on, or wipe on formulations can be applied directly to the soil (a soil drench), applied to growing plants expressing the proteins disclosed herein, or formulated to be applied to seed containing one or more transgenes encoding one or more of the proteins disclosed. Such formulations for use in seed treatments can be applied with various stickers and tackifiers known in the art. Such formulations can contain pesticides that are synergistic in mode of action with the proteins disclosed, so that the formulation pesticides act through a different mode of action to control the same or similar pests that can be controlled by the proteins disclosed, or that such pesticides act to control pests within a broader host range or plant pest species that are not effectively controlled by the TIC2463-related pesticidal proteins.

A pest-inhibitory composition or formulation that includes the recombinant polypeptides and proteins can further be combined with an agriculturally-acceptable carrier, such as a powder, dust, pellet, granule, spray, emulsion, colloid, or solution, a *Bacillus* spore/crystal preparation, a seed treatment, a recombinant plant cell/plant tissue/seed/plant transformed to express one or more of the proteins, or bacterium transformed to express one or more of the proteins. Depending on the level of pesticidal or insecticidal inhibition inherent in the recombinant polypeptide and the level of formulation to be applied to a plant or diet assay, the composition or formulation can include various by weight amounts of recombinant polypeptide, e.g., from 0.0001% to 0.001% to 0.01% to 1% to 99% by weight of the recombinant polypeptide molecule.

Methods or kits for detecting DNA, RNA, or protein embodiments corresponding to the TIC2463-related proteins or distinguishing insect inhibitory fragments and segments thereof, methods for identifying additional members of the genus of proteins described in this application, methods for identifying novel proteins related to genus family members, methods for testing for control of insect growth or infestation, and methods for providing such control to plants and other recipient hosts are also provided in this application.

As referenced above, TIC2463-related proteins can be used to produce antibodies (or similar specific binding agents such as anticalins, lipocalins and/or alphabodies) that bind specifically to this class/genus of protein and these antibodies can be used to screen and find other members of the genus. By reference to the word "antibody" herein, it is intended to refer to any class of protein that can be modified by any means to effect specific binding to an antigen or epitope of a target molecule, including animal antibodies (including IgA, IgE, IgG and IgM type antibodies, and plant and bacterial protein structures such as anticalins, lipocalins and alphabodies, and lectins). An antibody by itself, or in a mixture of antibodies, that binds specifically to an epitope of one or more of the recombinant polypeptides disclosed herein as a TIC2463-related toxin protein or part thereof is specifically contemplated. A method of using this antibody by itself, or in a mixture of antibodies, to detect or quantify proteins sharing epitopes of the proteins of the disclosed herein is also contemplated. Such a method to detect or quantify can include the steps of contacting a sample with the antibody and using detection means well known in the art to detect the binding of antibody to a polypeptide target in the sample. Where one or more epitopes are contemplated and their combination is used in such a method, the binding of an antibody or mixture of antibodies recognizing different epitopes can identify a polypeptide exhibiting homology to the recombinant polypeptides that are described herein.

Kits for detecting the presence of a polypeptide target in a sample suspected of containing a TIC2463 or related polypeptide target are provided. Such kits would include one or more reagent(s) used for epitope detection and one or more control reagent(s) to show that the detection is operating within statistical variances. Reagent storage, instructions for detection means and use of reagents, and additional parts and tools that can be included in such kits are contemplated.

Methods of testing are provided for testing the TIC2463-related polypeptides described herein for pesticidal activity. Such methods are referred to herein singly as a "bioassay" and a plurality of tests as "bioassays". Described herein are qualitative insect bioassays that measure growth inhibition, mortality, or a combination of both. The insect orders tested in the following examples include Coleoptera. The diet recipe and preparation, the preparation of test and control samples, the insect preparation, and the procedures for conducting assays are typically dependent upon the type and size of the insect and/or pest being subjected to any particular evaluation.

In view of the foregoing, those of skill in the art should appreciate that changes can be made in the specific aspects which are disclosed and still obtain a like or similar result without departing from the spirit and scope of the embodiments described herein. Thus, specific details disclosed in the experimental examples described below are not intended to be limiting, nor should they be interpreted as such.

EXAMPLES

In view of the foregoing, those of skill in the art should appreciate that changes can be made in the specific aspects which are disclosed and still obtain a like or similar result without departing from the spirit and scope of the invention. Thus, specific structural and functional details disclosed herein are not to be interpreted as limiting. It should be understood that the entire disclosure of each reference cited herein is incorporated within the disclosure of this application.

Example 1

Discovery, Cloning, and Expression of TIC2463-Related Pesticidal Proteins

*Bacillus thuringiensis* ("Bt") strains exhibiting distinctive attributes, particularly pesticidal activity, were identified and genomic libraries were constructed for each strain. Genomic libraries of such bacterial strains were created in vectors from which clones were identified that contain open reading frames ("ORFs") encoding amino acid sequences that were hypothesized to exhibit pesticidal activity.

A Bt strain, EG3957, was found to exhibit Coleopteran insecticidal activity. A library constructed from the genome of this strain resulted in the identification of a clone that appeared to contain an ORF encoding a novel Bt protein, TIC1373 (SEQ ID:40). The TIC1373 amino acid sequence appeared to exhibit a distant relationship (less than 29% amino acid sequence identity) to a known Bt insecticidal toxin referred to as Cry60. Cry60 proteins contain peptide elements that are characteristic of *Clostridium* epsilon toxin ETX family members as well as mosquitocidal toxin MTX family members (pfam03318). Cry60 proteins are also related to the Cry15Aa1 protein because both Cry60 and Cry15Aa1 contain ETX/MTX pfam characteristics. Cry60 and Cry15 proteins are not known to be insecticidal except perhaps to mosquito larvae. Therefore, the distant relationship of this apparently novel Bt protein, TIC1373 (SEQ ID NO:40), to the Cry60 and Cry15 pfam was suggestive that insecticidal activity may be observed from the expression of the TIC1373 peptide from a plasmid containing a Bt sporulation promoter directing the expression of the TIC1373 ORF in an acrystalliferous strain of *Bacillus thuringiensis*. The resulting recombinant strain failed to exhibit any insecticidal activity when tested in bioassay against a battery of plant pests, and a protein corresponding to the mass of the predicted TIC1373 was not detected in the culture supernatant or spore/cell pellet.

The distant relationship of the TIC1373 protein sequence to the ETX/MTX type toxin Cry60 suggested that the TIC1373 protein may exhibit some unusual or difficult to characterize pesticidal activity. However, as explained previously, the TIC1373 peptide did not exhibit pesticidal activity against any insect tested in a battery of insect bioassays, including tests against Coleopteran, Lepidopteran, and Hemipteran pest species. It was hypothesized that proteins related to the TIC1373 peptide may be present in other microbial strains and the variations present within the amino acid sequences of related proteins may result in toxin activity. Therefore, the TIC1373 protein coding sequence was used to identify other microbial strains that contained related sequences homologous to the predicted TIC1373 protein. Such homologous sequences were cloned and sequenced and open reading frames that resembled the TIC1373 open reading frame were identified.

One additional homologous protein that was identified is set forth in SEQ ID NO:2, designated in this application as TIC1825. The sequence encoding TIC1825 as set forth in SEQ ID NO:1, was obtained from Bt strain EG5015. The predicted TIC1825 protein amino acid sequence exhibited substantial identity to TIC1373 (77% identity across the length of the TIC1373 protein). Surprisingly, TIC1825 contained an additional 31 N-terminal amino acids compared to the TIC1373 protein. Expression of the TIC1825 protein from an acrystalliferous strain of Bt surprisingly exhibited Coleopteran insecticidal activity in the cell pellet, as well as in the culture supernatant, suggesting that the protein toxin may be secreted into the culture medium.

The TIC1825 protein was collected from the culture supernatant and an N-terminal amino acid sequence analysis of the protein indicated that the TIC1825 protein predicted from the TIC1825 gene ORF was a precursor protein that contained a 33 amino acid signal peptide that was likely responsible for targeting the nascent TIC1825 protein for secretion into the culture supernatant when expressed in the acrystalliferous strain of *Bacillus thuringiensis*. It was determined that the full length TIC1825 open reading frame (SEQ ID NO:1 from nucleotide position 1-945) encoded a toxin precursor protein that is processed into a mature toxin protein encoded by nucleotides 100-945. The secreted protein amino terminal sequence information combined with the fact that the ORF encoded an N-terminal peptide segment not present in the secreted form of the protein suggested that the predicted amino terminal peptide segment is a secretory signal peptide encoded by nucleotides 1-99 as set forth in SEQ ID NO:1.

Based on the TIC1825 data, additional sequence information was obtained from Bt strain EG3957, the strain from which TIC1373 data had been originally obtained. It was determined that additional sequence information existed upstream of the original TIC1373 clone that contained a sequence encoding an N-terminal amino acid segment similar to the N-terminal signal peptide segment encoded by the TIC1825 coding sequence. Assembly of this additional information together with the TIC1373 sequence information resulted in an ORF encoding TIC2463 (SEQ ID NO:4). Surprisingly, expression of a clone containing the ORF encoding TIC2463 (SEQ ID NO:3 from nucleotide position 1 through 939) resulted in insecticidal activity toxic to Coleopteran species, present both in the culture supernatant as well as partially retained within the cell pellet of the culture.

Additional Bt strains exhibiting Coleopteran toxic activity were screened for the presence of TIC2463-related toxin proteins. Table 3 summarizes the discovered Bt strains and toxins.

TABLE 3

Bt Strains, Proteins Related to TIC2463, & SEQ ID NO's

| Protein | Bt Strain | SEQ ID NO |
|---|---|---|
| TIC1373 | EG3957 | 40 |
| TIC1825 | EG5015 | 2 |
| TIC2463 | EG3957 | 4 |
| TIC2461 | EG6106 | 6 |
| TIC3037 | CFB202735 | 8 |
| TIC2228 | EG9095 | 10 |
| TIC3005 | CFB005050 | 12 |
| TIC2593 | EG3855 | 14 |
| TIC2598 | EG4492 | 16 |
| TIC3891 | EG4227 | 18 |
| TIC3090 | EG5554 | 20 |
| TIC3626 | CFB212742 | 22 |
| TIC2081 | EG6734 | 24 |

Example 2

TIC2463-Related Proteins Exhibit Coleopteran Activity in Insect Bioassay

The TIC2463-related pesticidal proteins were expressed in Bt and assayed for toxicity to various species of Coleoptera. Preparations of each toxin from Bt were assayed against the Coleoptera species *Leptinotarsa decemlineata* (Colorado potato beetle, CPB), *Diabrotica virgifera virgifera* (Western Corn Rootworm, WCR), and *Diabrotica undecimpunctata howardii* (Southern Corn Rootworm, SCR).

Proteins discovered as described in Example 1 were produced from recombinant acrystalliferous Bt strains transformed with a vector encoding the respective TIC2463-related protein. Proteins were extracted from the recombinant bacterial fermentations and used in diet bioassays.

Protein samples for the diet bioassays were provided either as spore crystal protein suspensions or as soluble protein in spent bacterial growth media. Crystal spore protein suspensions of proteins were prepared in a buffer of Tris-HCl (10 mM, pH=8), EDTA (0.1 mM), Triton-X 100 (0.005% v/v) and benzonase (0.001% w/v). Protein concentrations were determined and diluted as appropriate using suspension buffer.

Test samples of the proteins were overlaid onto diet surfaces in individual bioassay compartments. Control samples were prepared by overlaying aliquots of suspension buffer or spent growth media, as appropriate, onto diet surfaces. Each compartment was infested with a single insect species, incubated, and scored for mortality and stunting.

For the CPB assays, each sample well was infested with eight neonates. The sample compartments were placed into a controlled environment at 25 C and 70% relative humidity without light for a period of five days. For the WCR assays, each sample well was infested with eight neonates. The sample compartments were incubated in a controlled environment at 25 C and 70% relative humidity without light for a period of six days. For the SCR assays, five to seven washed eggs which were placed onto the diet surface of each sample compartment. The plates were stored in a controlled environment at 25 C and 70% relative humidity without light for a period of about twenty four hours and monitored for hatch. The assays were scored six days after hatch.

Insecticidal activity in the CPB and WCR assays was measured by scoring samples for mortality count (based on infested wells only) and stunting levels. For the SCR assays, insect mortality was based only on the number of eggs that were observed to have hatched. Stunting (representing the relative size of surviving insects to that of untreated specimens) was visually estimated.

TIC1825 (SEQ ID NO:2) and TIC2463 (SEQ ID NO:4) were tested for efficacy against CPB in diet bioassays as described. TIC1825 was provided as a crystal spore suspension. Mortality was observed at protein concentrations of at least 0.008 micrograms of protein per milliliter of diet. Stunting was observed at all concentrations tested. No stunting or mortality was observed with the buffer control samples. TIC2463 was provided as a crystal spore preparation and as soluble protein in spent media. The crystal spore prep as well as the spent media exhibited significant mortality. The crystal spore prep exhibited mortality at concentrations as low as 0.162 micrograms of protein per milliliter of diet. The spent media exhibited mortality at concentrations as low as 0.600 micrograms per milliliter diet. No stunting or mortality was observed with the buffer control samples. Both TIC2463 and TIC1825 demonstrated insecticidal activity against CPB.

Additional TIC2463-related toxins were prepared and tested for efficacy against CPB and WCR. The results of these bioassay experiments are reported in Table 4. In addition to TIC1825 and TIC2463, TIC3891 (SEQ ID NO:18), TIC2461 (SEQ ID NO:6), TIC3626 (SEQ ID NO:22), TIC3037 (SEQ ID NO:8), TIC1825v1 (SEQ ID NO:26), TIC1825v2 (SEQ ID NO:28), and TIC1825v3 (SEQ ID NO:30) exhibited pesticidal activity.

TABLE 4

Pesticidal Activity of TIC2463 Family Proteins

| Protein | CPB | WCR |
|---|---|---|
| TIC1825 | S/M | NA |
| TIC2463 | M | S/M |
| TIC2593 | NT | NT |
| TIC2598 | NA | NA |
| TIC3005 | NT | NT |
| TIC1373 | NT | NA |
| TIC3891 | S/M | NT |
| TIC2461 | S/M | NA |
| TIC2081 | NA | NA |
| TIC2228 | NA | NA |
| TIC3626 | S | NA |
| TIC3037 | M | NA |
| TIC3090 | NT | NT |
| TIC1825v1 | NT | S/M |

TABLE 4-continued

| Pesticidal Activity of TIC2463 Family Proteins | | |
|---|---|---|
| Protein | CPB | WCR |
| TIC1825v2 | NT | S/M |
| TIC1825v3 | NT | S/M |

CPB & WCR diet bioassay only
M—mortality observed (vs buffer control) at concentrations tested
S—survivors stunted (vs buffer control) at concentrations tested
NA—not active as tested
NT—not tested
+—effective results

Example 3

TIC1825 Amino Acid Sequence Variants

This example illustrates that certain TIC1825 amino acid sequence variants exhibit improved pesticidal activity against corn rootworms in bioassay compared to native TIC1825 protein.

Alignment of the amino acid segments corresponding to the toxic portion of each of the TIC2463-related toxin protein family members shows amino acid sequence differences among the family members. Taking the alignment data as set forth in FIG. 1 together with the toxic profile data as set forth in Table 4 above, it was observed that TIC2463-related proteins that contain an alanine at the position corresponding to amino acid sequence position 233 as set forth in SEQ ID NO:4 for TIC2463 exhibit toxicity when tested against both CPB and corn rootworms. This suggested that proteins such as TIC1825, exhibiting toxic activity to CPB but not against CRW, may exhibit a broader host range and perhaps a greater toxic effect if the amino acids at or near the amino acid position 233 in TIC1825 more closely resembled the amino acids at the corresponding position in TIC2463.

To test this hypothesis, TIC1825 proteins containing various amino acid substitutions consistent with the analogous positions within TIC2463 were produced and included in bioassays against corn rootworms and CPBs. The TIC1825 coding sequence (SEQ ID NO:1) was subjected to modifications that resulted in changing the codons encoding the amino acid glycine (G) at position 233 to an alanine (A) and proline (P) at position 234 to an alanine. Each of these modifications caused the TIC1825 protein to more closely resemble TIC2463 at these positions. The TIC1825_G233A variant (TIC1825v1, SEQ ID NO:26) was constructed to contain only the G to A change at position 233 (encoded by SEQ ID NO:25). The TIC1825_P234A variant (TIC1825v2, SEQ ID NO:28) was constructed to contain only the P to A change at position 233 (encoded by SEQ ID NO:27). A third variant (TIC1825v3, SEQ ID NO:30, encoded by SEQ ID NO:29) was constructed in which an alanine substitution was introduced at positions 233 and 234, along with a substitution of threonine (T) at position 224 for lysine (K), asparagine (N) at position 226 for asparatate (D), threonine (T) at position 246 for leucine (L), and valine (V) at position 248 for threonine (T). These changes are reflected by the presence of bold characters on the line in FIG. 1D corresponding to TIC1825_V1, _V2 and _V3.

Constructs encoding these amino acid sequence variants were expressed in an acrystalliferous strain of *Bacillus thuringiensis*. Protein corresponding to the TIC1825 variant(s) produced from fermentations of these recombinant strains was isolated for subsequent testing in diet bioassay against corn rootworm as well as other *Diabrotica* species. The variants were observed to exhibit corn rootworm bioactivity, and the results are shown in last three rows of Table 4.

TIC2463-related toxin protein family members that do not contain alanine at the corresponding amino acid position 233 and which do not exhibit corn rootworm bioactivity can be tested using similar substitutions and confirmation of bioactivity against corn rootworms. It is anticipated that modifying other TIC2463-related toxin protein family members to contain an alanine at amino acid position 233 will result in insecticidal activity against corn rootworm.

Example 4

TIC2463-Related Proteins Demonstrate Activity Against Coleopteran Pests when Expressed in Stably Transformed Corn Plants This example demonstrates that the in vitro bioactivity of the TIC2463-related toxin proteins shown in Example 2 and the TIC1825 variants set forth in Example 3 is also exhibited when expressed in planta. Corn plants expressing these proteins show significant reduced root damage when infested by Coleopteran pest species such as corn rootworms.

Polynucleotide sequences encoding proteins that are derived from *Bacillus* bacterial systems are ineffective for expression in plants (U.S. Pat. No. 5,500,365). Expression cassettes have been constructed that contain artificial polynucleotide sequences designed for use in plants that encode a TIC2463-related protein toxin. Polynucleotide sequences are provided herein as set forth in SEQ ID NO's 33, 35, 43, 44, 45, 46, and 47. Each of these polynucleotide sequences encodes a TIC2463 related protein toxin, and each can be introduced into a DNA construct containing at least a plant functional promoter operably linked to the polynucleotide sequence encoding the toxin protein. The polynucleotide sequence encoding the TIC2463-related toxin proteins will also contain at the 3' end of the toxin coding sequence a translation termination codon (TAA, TAG, or TGA) followed by and operably linked to a DNA segment corresponding to a plant functional 3' transcription termination and polyadenylation sequence. The expression cassette can be introduced directly into plant cells by microparticle bombardment, infusion or other transformation methods known to those of ordinary skill in the art. Alternatively, the construct can be introduced into a plant transformation vector and inserted into the plant cell genome using *Agrobacterium* or *Rhizobium* mediated plant transformation methods. In any case, stable and heritable introduction of the construct into the plant genome allows for the selection of one or more transgenic events that can be tested for pesticidally effective amounts of expression of the TIC2463 related toxin protein. The TIC2463 related toxin protein expressed in such plants can be designed to express the native signal peptide, or a heterologous signal peptide or a targeting peptide. The heterologous signal peptide can be a signal peptide derived from a different TIC2463 related toxin protein, other bacterial signal peptides functional in *Bacillus* species, a plant functional signal peptide, or a targeting peptide. For applicable host cells, these signal/targeting peptides will result in the inserted by secretion of the mature toxin segment of the TIC2463 related toxin protein into a subcellular organelle or compartment such as a chloroplast, a plastid, a mitochondria, a vacuole, or an amyloplast.

F1 transgenic corn plants expressing Cry3Bb were used as positive controls. Negative controls contained no transgenes encoding insecticidal toxin proteins. F1 corn plants transformed to contain a construct expressing a TIC2463-related protein were compared to negative controls and to Cry3Bb transgenic events. The F1 plants were transferred to soil in caged pots, infested with sixty WCR neonates per pot, and grown for thirteen days under controlled greenhouse conditions. Plants were evaluated after sixty days for root damage and scored using the rating scale described by Oleson, et al. (Journal of Economic Entomology (2005) 98(1):1-8). A score of zero is consistent with no injury, a score of three is consistent with the observation that three or more nodes have been pruned to within 1.5 inches of the stalk. Insect mortality was assessed by counting the number of $3^{rd}$ instar larvae remaining at the end of the evaluation period.

F1 assay results were calculated for individual events. Three of eight different transgenic events that were tested expressing TIC2463 exhibited significantly reduced root damage as compared to the negative controls. Nine separate events expressing TIC1825 each exhibited damage that was no better than or worse than damage observed in the negative controls.

Recombinant/transgenic plants were also obtained that expressed TIC2463 targeted to an amyloplast (SEQ ID NO:36) or to a chloroplast (SEQ ID NO:38) from the coding sequences as set forth in SEQ ID NO:35 or SEQ ID NO:37, respectively. Transgenic plant events were tested for resistance to corn rootworm infestation. The transgenic plants were observed to be resistant to rootworm infestation when compared to plants lacking a TIC2463 protein.

Similarly, maize plants were transformed and transgenic plants were obtained that expressed the following TIC2463 related protein variants: TIC1825_12 (SEQ ID NO:49), TIC1825_13 (SEQ ID NO:51), TIC1825_15 (SEQ ID NO:53), TIC2461_5 (SEQ ID NO:55), TIC2463_3 (SEQ ID NO:32), TIC2463_4 (SEQ ID NO:34), TIC2463_8 (SEQ ID NO:57), TIC2463_9 (SEQ ID NO:59) and TIC2463_10 (SEQ ID NO:61). When tested, these transgenic plants were found to be resistant to corn rootworm damage, when compared to plants lacking a TIC2463 related protein.

Transgenic events are obtained that express TIC1825 amino acid sequence variants having the amino acid sequences as set forth in SEQ ID NO:26, SEQ ID NO:28 and SEQ ID NO:30 and compared to transgenic plants expressing either a chloroplast targeted TIC1825 native toxin segment or a chloroplast targeted TIC2463 toxin. Plants transformed to contain the TIC1825 amino acid sequence variants will exhibit substantially improved corn rootworm resistance compared to plants expressing the native TIC1825 toxin protein.

Transgenic events of corn expressing a TIC2463 related protein (corn plants transformed with a polynucleotide designed for the expression of a TIC2463 related protein) are thus specifically contemplated by the present disclosure. Such plants may have a construct expressing a TIC2463 related protein linked directly to at least one additional construct that is designed for expression of an additional toxic agent, such as a dsRNA designed for specifically targeting for suppression an essential gene in a Coleopteran pest (the Coleopteran pest can be the same or a different pest than that targeted for control by the TIC2463 related toxin protein). Alternatively, the linked additional construct designed for expression of an additional toxin agent may encode one or more additional toxin proteins, and at least one may be complementary to the TIC2463 related toxin, providing an additional mode of action that will reduce the likelihood of the development of resistance of a targeted Coleopteran pest to either of the Coleopteran specific toxins produced by the plant. The one or more additional toxin proteins may also include a toxin active against a pest of a different species, such as a Lepidopteran, Hemipteran, Homopteran, or Thysopteran pest species or a plant pathogenic nematode or fungal plant pathogen. Plants transformed to express such TIC2463 related toxins may also be combined by breeding with other traits, including but not limited to Coleopteran specific traits that are complementary to the TIC2463 related toxin mode of action, Lepidopteran traits, traits specific for increasing yield, decreasing sensitivity to drought, increase efficiency for utilization of nitrogen and the like, and traits known in the art that provide tolerance to herbicide applications. Seed treatments and topically applied formulations that complement the toxic activity of the TIC2463 related toxin mode of action are specifically contemplated, as well as chemistries that function to control genes in plants (dsRNA applications in particular), or to control other pest species as noted above.

Example 5

Minimal Active Core for TIC2463

This example illustrates a minimal active core sequence for TIC2463 pesticidal activity.

TIC2463-related protein deletion mutants were designed, cloned and expressed in an effort to determine the minimal protein sequence required for activity against western corn rootworm (WCR). To investigate the active core of TIC2463, mutants with deletions in six regions of the protein were selected for WCR bioassay testing. Deletion mutants expressing protein were purified and normalized to 50 ppm and tested in a WCR diet bioassay, with TIC2463 (SEQ ID NO:4) as a comparator. The bioassay stunting data suggests that deletions of the putative secretion signal site and the C-terminus maintain activity against WCR. The stunting score for these deletion mutant proteins was 2-3 while the wild-type was 3. Further, a deletion at amino acid 40 showed no activity, indicating that amino acid 40 is critical for activity. Deletions near the middle of the sequence and the loop toward the N-terminus of the protein resulted in loss of activity. The stunting scores for these deletion mutant proteins was 0-1 while the wild-type was 3.

Based on this bioassay data, the central sequence, from amino acid residues 40 to 309, appears to be the minimal core of TIC2463 that possesses pesticidal activity.

What is claimed is:

1. A recombinant nucleic acid molecule comprising a heterologous promoter operably linked to a polynucleotide segment encoding a polypeptide comprising SEQ ID NO: 4 and exhibiting insect inhibitory activity.

2. The recombinant nucleic acid molecule of claim 1, wherein said recombinant nucleic acid molecule comprises a heterologous promoter operably linked to a polynucleotide segment having a nucleotide sequence comprising SEQ ID NO:3 from position 100-939.

3. The recombinant nucleic acid molecule of claim 1, wherein said recombinant nucleic acid molecule encodes a polypeptide comprising a targeting peptide selected from the group consisting of a secretion peptide, a chloroplast targeting peptide, a plastid targeting peptide, and an amyloplast targeting peptide.

4. A host cell having stably incorporated into its genome at least one DNA construct comprising said recombinant nucleic acid molecule according to claim 1, wherein said host cell is a bacterial host cell, a yeast host cell, or a plant host cell.

* * * * *

SEQUENCE LISTING

```
<160> NUMBER OF SEQ ID NOS: 61

<210> SEQ ID NO 1
<211> LENGTH: 948
<212> TYPE: DNA
```

<213> ORGANISM: Bacillus thuringiensis
<220> FEATURE:
<221> NAME/KEY: misc_feature
<222> LOCATION: (1)..(945)
<223> OTHER INFORMATION: Open Reading Frame TIC1825; BT EG5015
<220> FEATURE:
<221> NAME/KEY: misc_feature
<222> LOCATION: (1)..(99)
<223> OTHER INFORMATION: signal peptide coding sequence
<220> FEATURE:
<221> NAME/KEY: misc_feature
<222> LOCATION: (100)..(945)
<223> OTHER INFORMATION: mature peptide coding sequence

<400> SEQUENCE: 1
atgacgaacc tatttaaatc tcaaaaaact tttatagcca aactaggaat tgtattagga 60
atatcaagta ccctgttttt tggaagtaat gtcatggcag ctcaaaccac aaatattaca 120
gatgtagatg cacaaatgga caaaatttct gatttttatt ttaaaaacga attagaatgg 180
aaagacttac ctgaataccc tggagcttat cattatatta gattagatag taaaaaaaca 240
aatatggatt tagatctcaa agcgagcaat ttaaaaaatt taacttatag tgatttacat 300
ccagaatata ttggtgaaaa tgaatttgat aatacaaatg gcagtataga tcaaacattc 360
acaacagcat cgtattctca tcaagttacg aactccgcta gtacaagtgt tacggaaggg 420
tttaaagtag gaggaaaaac aacgcttttt aaattaccta ttttattaac agatggtgtt 480
gatattactg cagaattcaa ctctgcaaca agtacaacaa atacagttac agatactaag 540
actttaacag cttcaccaca aaatataaaa gttccagctg gtaaaaaata tttagttaaa 600
gtggatatgg ctaaaaaaac atttaatgga gatatagaat ttagtgcaaa tggaaagaat 660
gtaaaatcga aacttgacac cttagcaact tattatggac ccggattccc acgtccaaat 720
aaatatccat cacttctatt tacaacagca gatatgtgga aaaagttatc tactagtcag 780
caaaatcaaa taaagggagt tacttttgat tctagtaaaa atcttatatt gaatgggaaa 840
gcacatgtaa atggaatctt tggaagtaaa ctacgtgtta gtgtttatga tattacggat 900
tcaaaattat cacctaaact aattcaacag aaatttatgg agcaatga 948

<210> SEQ ID NO 2
<211> LENGTH: 315
<212> TYPE: PRT
<213> ORGANISM: Bacillus thuringiensis
<220> FEATURE:
<221> NAME/KEY: MISC_FEATURE
<222> LOCATION: (1)..(315)
<223> OTHER INFORMATION: precursor TIC1825; Bt EG5015
<220> FEATURE:
<221> NAME/KEY: MISC_FEATURE
<222> LOCATION: (1)..(33)
<223> OTHER INFORMATION: signal peptide amino acid sequence
<220> FEATURE:
<221> NAME/KEY: MISC_FEATURE
<222> LOCATION: (34)..(315)
<223> OTHER INFORMATION: mature peptide amino acid sequence

<400> SEQUENCE: 2

Met Thr Asn Leu Phe Lys Ser Gln Lys Thr Phe Ile Ala Lys Leu Gly
1 5 10 15

Ile Val Leu Gly Ile Ser Ser Thr Leu Phe Phe Gly Ser Asn Val Met
20 25 30

Ala Ala Gln Thr Thr Asn Ile Thr Asp Val Asp Ala Gln Met Asp Lys
35 40 45

Ile Ser Asp Phe Tyr Phe Lys Asn Glu Leu Glu Trp Lys Asp Leu Pro
50 55 60

Glu Tyr Pro Gly Ala Tyr His Tyr Ile Arg Leu Asp Ser Lys Lys Thr
65 70 75 80

Asn Met Asp Leu Asp Leu Lys Ala Ser Asn Leu Lys Asn Leu Thr Tyr
85 90 95

Ser Asp Leu His Pro Glu Tyr Ile Gly Glu Asn Glu Phe Asp Asn Thr
100 105 110

Asn Gly Ser Ile Asp Gln Thr Phe Thr Thr Ala Ser Tyr Ser His Gln
115 120 125

Val Thr Asn Ser Ala Ser Thr Ser Val Thr Glu Gly Phe Lys Val Gly
130 135 140

Gly Lys Thr Thr Leu Phe Lys Leu Pro Ile Leu Leu Thr Asp Gly Val
145 150 155 160

Asp Ile Thr Ala Glu Phe Asn Ser Ala Thr Ser Thr Thr Asn Thr Val
165 170 175

Thr Asp Thr Lys Thr Leu Thr Ala Ser Pro Gln Asn Ile Lys Val Pro
180 185 190

Ala Gly Lys Lys Tyr Leu Val Lys Val Asp Met Ala Lys Lys Thr Phe
195 200 205

Asn Gly Asp Ile Glu Phe Ser Ala Asn Gly Lys Asn Val Lys Ser Lys
210 215 220

Leu Asp Thr Leu Ala Thr Tyr Tyr Gly Pro Gly Phe Pro Arg Pro Asn
225 230 235 240

Lys Tyr Pro Ser Leu Leu Phe Thr Thr Ala Asp Met Trp Lys Lys Leu
245 250 255

Ser Thr Ser Gln Gln Asn Gln Ile Lys Gly Val Thr Phe Asp Ser Ser
260 265 270

Lys Asn Leu Ile Leu Asn Gly Lys Ala His Val Asn Gly Ile Phe Gly
275 280 285

Ser Lys Leu Arg Val Ser Val Tyr Asp Ile Thr Asp Ser Lys Leu Ser
290 295 300

Pro Lys Leu Ile Gln Gln Lys Phe Met Glu Gln
305 310 315

<210> SEQ ID NO 3
<211> LENGTH: 942
<212> TYPE: DNA
<213> ORGANISM: Bacillus thuringiensis
<220> FEATURE:
<221> NAME/KEY: misc_feature
<222> LOCATION: (1)..(939)
<223> OTHER INFORMATION: Open Reading Frame TIC2463; Bt EG3957
<220> FEATURE:
<221> NAME/KEY: misc_feature
<222> LOCATION: (1)..(99)
<223> OTHER INFORMATION: signal peptide coding sequence
<220> FEATURE:
<221> NAME/KEY: misc_feature
<222> LOCATION: (100)..(939)
<223> OTHER INFORMATION: mature peptide coding sequence

<400> SEQUENCE: 3
atgaagattc tatggaaacc ccaaaaaact tttatttcca acctagcgat tgtattggga 60
atttcaagta ccctgttttt tggaagtaat gtcatggcag atcaaacagc aaatattaca 120
gatgtagatg cacaaatgga caagatttca gatttttatt ttaaaaacga gttagaatgg 180
aaagatttac ctgaatatcc tggagcatat cattatatta gattggatag taaaaaaaca 240
aatatggatt tagatttaaa agcgaacaat ataaaaaatt taacttatag tgatttaaat 300

-continued

```
ccagaatatg tcggtgaaaa tgaatttgat aatacaaata gtaatataga ccaaacattc    360

acaacagcgg cctattccca tcaagttaca aactcggcta gtacaaatgt tactaaaggg    420

tttaaagtgg gcggaaaaac aacgcttctt aaattaccga ttttattaac aagtggagtt    480

gagattaatg cagaatttaa ctctgcaaca agtacgacga atacagttac agataccaag    540

actttaactg cttctccaca aaatataaag gttccagccg gtaggaagtt tctagttaaa    600

gtagatatgg ccaaaaaaac atttaatgga gaagtagact ttagtgcaac aggatataat    660

gtaaaatcaa cgcttaacac gttagcaact tattatgcag cagggttccc acgtccaaat    720

aaatatccat cacttacatt tgtcacagca gatatgtgga aaaagttatc tactagtcaa    780

caaaatcaaa taaatggagt taattttgat tctagtaaag atcttgtgtt aaatgggaaa    840

gcgaatgtac atgggatttt tggaagtaca ctacgtgtga gcgtttatga tattacagat    900

tcaaaattat cacctaaact agttcaacat aaaaacatat ga                       942


<210> SEQ ID NO 4
<211> LENGTH: 313
<212> TYPE: PRT
<213> ORGANISM: Bacillus thuringiensis
<220> FEATURE:
<221> NAME/KEY: MISC_FEATURE
<222> LOCATION: (1)..(313)
<223> OTHER INFORMATION: precursor TIC2463; Bt EG3957
<220> FEATURE:
<221> NAME/KEY: MISC_FEATURE
<222> LOCATION: (1)..(33)
<223> OTHER INFORMATION: signal peptide amino acid sequence
<220> FEATURE:
<221> NAME/KEY: MISC_FEATURE
<222> LOCATION: (34)..(313)
<223> OTHER INFORMATION: mature peptide amino acid sequence

<400> SEQUENCE: 4

Met Lys Ile Leu Trp Lys Pro Gln Lys Thr Phe Ile Ser Asn Leu Ala
1               5                   10                  15

Ile Val Leu Gly Ile Ser Ser Thr Leu Phe Phe Gly Ser Asn Val Met
            20                  25                  30

Ala Asp Gln Thr Ala Asn Ile Thr Asp Val Asp Ala Gln Met Asp Lys
        35                  40                  45

Ile Ser Asp Phe Tyr Phe Lys Asn Glu Leu Glu Trp Lys Asp Leu Pro
    50                  55                  60

Glu Tyr Pro Gly Ala Tyr His Tyr Ile Arg Leu Asp Ser Lys Lys Thr
65                  70                  75                  80

Asn Met Asp Leu Asp Leu Lys Ala Asn Asn Ile Lys Asn Leu Thr Tyr
                85                  90                  95

Ser Asp Leu Asn Pro Glu Tyr Val Gly Glu Asn Glu Phe Asp Asn Thr
            100                 105                 110

Asn Ser Asn Ile Asp Gln Thr Phe Thr Thr Ala Ala Tyr Ser His Gln
        115                 120                 125

Val Thr Asn Ser Ala Ser Thr Asn Val Thr Lys Gly Phe Lys Val Gly
    130                 135                 140

Gly Lys Thr Thr Leu Leu Lys Leu Pro Ile Leu Leu Thr Ser Gly Val
145                 150                 155                 160

Glu Ile Asn Ala Glu Phe Asn Ser Ala Thr Ser Thr Thr Asn Thr Val
                165                 170                 175

Thr Asp Thr Lys Thr Leu Thr Ala Ser Pro Gln Asn Ile Lys Val Pro
            180                 185                 190

Ala Gly Arg Lys Phe Leu Val Lys Val Asp Met Ala Lys Lys Thr Phe
```

```
        195                 200                 205

Asn Gly Glu Val Asp Phe Ser Ala Thr Gly Tyr Asn Val Lys Ser Thr
    210                 215                 220

Leu Asn Thr Leu Ala Thr Tyr Tyr Ala Ala Gly Phe Pro Arg Pro Asn
225                 230                 235                 240

Lys Tyr Pro Ser Leu Thr Phe Val Thr Ala Asp Met Trp Lys Lys Leu
                245                 250                 255

Ser Thr Ser Gln Gln Asn Gln Ile Asn Gly Val Asn Phe Asp Ser Ser
            260                 265                 270

Lys Asp Leu Val Leu Asn Gly Lys Ala Asn Val His Gly Ile Phe Gly
        275                 280                 285

Ser Thr Leu Arg Val Ser Val Tyr Asp Ile Thr Asp Ser Lys Leu Ser
    290                 295                 300

Pro Lys Leu Val Gln His Lys Asn Ile
305                 310
```

<210> SEQ ID NO 5
<211> LENGTH: 1014
<212> TYPE: DNA
<213> ORGANISM: Bacillus thuringiensis
<220> FEATURE:
<221> NAME/KEY: misc_feature
<222> LOCATION: (1)..(1011)
<223> OTHER INFORMATION: Open Reading Frame TIC2461; Bt EG6106
<220> FEATURE:
<221> NAME/KEY: misc_feature
<222> LOCATION: (1)..(84)
<223> OTHER INFORMATION: signal peptide coding sequence
<220> FEATURE:
<221> NAME/KEY: misc_feature
<222> LOCATION: (85)..(1011)
<223> OTHER INFORMATION: mature peptide coding sequence

<400> SEQUENCE: 5

```
atggaactaa aaagaatatg gaaatgtctt acaatttctg ccgtcttatc ccagatcgct     60

gtctatccag taacatctta tgcagtcagc aacacggaac aaaatactga caatatgaaa    120

ataacggaag aaaaaagtaa tatgataaga aatggtttac taggaaatgt tcataaatcc    180

tctgtcaaat ctgcctactc ttccaatgtt actaacgttg acgaacagat gaacaaaatt    240

tctgattttt attatcaaaa taaccttcgg gggaaagaaa tctcgactta ctattatgta    300

aaccaattaa aagaaaaaaa gactactatg tccttagatc ttaatgcttc tgatataaat    360

aacgtaacat ataatgactt acaaccagaa tatataggtg aaaacgaatt tcaaaatact    420

acggatcaag atcaaacatt tacaacagca gcctattctc atgcagttac agacactgta    480

agttctactg ttacgaatgg atttaaaatc ggaggtagtg gagatactat tttcaaaatt    540

cctattttat taaaagatgg aataaaactg agtgcagaat tcaattccgc tacgagtaca    600

acgaacacaa ctacagatac gaagacgctt acagcatctc ctcaaaacat caaggtacca    660

gcaggtaaaa cctataaggt ggtagtaaat ctatacaaga aaagcttcga aggggatata    720

gacttcactg gtaaagcaac caatgtaaat tcaaaattaa cagtaaatgc aacatatgtt    780

ggtcatggat tccctcgacg tgataaagag cagtcctaca cctatgctac agcagacatg    840

ttgaaagatt taacgaatga tcaacgaaat caaattaccg gaatctcctt tgataataat    900

aagaatttaa cgcttaatgg gaaagcaaaa atagagggta tttatggaag taaattacaa    960

gtgagtgtat atgatattac aaataatgct catagattag tacaagtatt ctag         1014
```

<210> SEQ ID NO 6

<211> LENGTH: 337
<212> TYPE: PRT
<213> ORGANISM: Bacillus thuringiensis
<220> FEATURE:
<221> NAME/KEY: MISC_FEATURE
<222> LOCATION: (1)..(337)
<223> OTHER INFORMATION: precursor TIC2461; Bt EG6106
<220> FEATURE:
<221> NAME/KEY: MISC_FEATURE
<222> LOCATION: (1)..(28)
<223> OTHER INFORMATION: signal peptide amino acid sequence
<220> FEATURE:
<221> NAME/KEY: MISC_FEATURE
<222> LOCATION: (29)..(337)
<223> OTHER INFORMATION: mature peptide amino acid sequence

<400> SEQUENCE: 6

```
Met Glu Leu Lys Arg Ile Trp Lys Cys Leu Thr Ile Ser Ala Val Leu
1               5                   10                  15

Ser Gln Ile Ala Val Tyr Pro Val Thr Ser Tyr Ala Val Ser Asn Thr
            20                  25                  30

Glu Gln Asn Thr Asp Asn Met Lys Ile Thr Glu Glu Lys Ser Asn Met
        35                  40                  45

Ile Arg Asn Gly Leu Leu Gly Asn Val His Lys Ser Ser Val Lys Ser
    50                  55                  60

Ala Tyr Ser Ser Asn Val Thr Asn Val Asp Glu Gln Met Asn Lys Ile
65                  70                  75                  80

Ser Asp Phe Tyr Tyr Gln Asn Asn Leu Arg Gly Lys Glu Ile Ser Thr
                85                  90                  95

Tyr Tyr Tyr Val Asn Gln Leu Lys Glu Lys Lys Thr Thr Met Ser Leu
            100                 105                 110

Asp Leu Asn Ala Ser Asp Ile Asn Asn Val Thr Tyr Asn Asp Leu Gln
        115                 120                 125

Pro Glu Tyr Ile Gly Glu Asn Glu Phe Gln Asn Thr Thr Asp Gln Asp
    130                 135                 140

Gln Thr Phe Thr Thr Ala Ala Tyr Ser His Ala Val Thr Asp Thr Val
145                 150                 155                 160

Ser Ser Thr Val Thr Asn Gly Phe Lys Ile Gly Gly Ser Gly Asp Thr
                165                 170                 175

Ile Phe Lys Ile Pro Ile Leu Leu Lys Asp Gly Ile Lys Leu Ser Ala
            180                 185                 190

Glu Phe Asn Ser Ala Thr Ser Thr Thr Asn Thr Thr Thr Asp Thr Lys
        195                 200                 205

Thr Leu Thr Ala Ser Pro Gln Asn Ile Lys Val Pro Ala Gly Lys Thr
    210                 215                 220

Tyr Lys Val Val Val Asn Leu Tyr Lys Lys Ser Phe Glu Gly Asp Ile
225                 230                 235                 240

Asp Phe Thr Gly Lys Ala Thr Asn Val Asn Ser Lys Leu Thr Val Asn
                245                 250                 255

Ala Thr Tyr Val Gly His Gly Phe Pro Arg Arg Asp Lys Glu Gln Ser
            260                 265                 270

Tyr Thr Tyr Ala Thr Ala Asp Met Leu Lys Asp Leu Thr Asn Asp Gln
        275                 280                 285

Arg Asn Gln Ile Thr Gly Ile Ser Phe Asp Asn Asn Lys Asn Leu Thr
    290                 295                 300

Leu Asn Gly Lys Ala Lys Ile Glu Gly Ile Tyr Gly Ser Lys Leu Gln
305                 310                 315                 320

Val Ser Val Tyr Asp Ile Thr Asn Asn Ala His Arg Leu Val Gln Val
```

-continued 325 330 335

Phe

<210> SEQ ID NO 7
<211> LENGTH: 951
<212> TYPE: DNA
<213> ORGANISM: Bacillus thuringiensis
<220> FEATURE:
<221> NAME/KEY: misc_feature
<222> LOCATION: (1)..(948)
<223> OTHER INFORMATION: Open Reading Frame TIC3037; Bt CFB 202735
<220> FEATURE:
<221> NAME/KEY: misc_feature
<222> LOCATION: (1)..(93)
<223> OTHER INFORMATION: signal peptide coding sequence
<220> FEATURE:
<221> NAME/KEY: misc_feature
<222> LOCATION: (94)..(948)
<223> OTHER INFORMATION: mature peptide coding sequence

<400> SEQUENCE: 7
atgaagaata aaaaaaatat atttaaaatg tgttctgcta ctttagcgtt atctttagga 60
gttacagtct ttgtaccaac cgcatcatat gcggcaatta ctaatgataa atttctctct 120
cctgtaacat caactgattc taatattact aatgttgatg actcaatgaa caaaacttcc 180
gacttttatt ataaaaataa acttgataac aaagaactgg ggagttactg gcgtataaat 240
tcccttcaga gtaaaaagac tactatggat ttagagatta atagttctga tatacaaaat 300
ttaaaatata gtgattcaca accagaatat ataggtgaaa atgagtttaa aaatgatact 360
aatgaagagc aaataatgac aacggcaact tattctcatg aagttagaaa ttttgtagat 420
tctactgtta caaaaggatt tcaagcaaag ggtgaagggg catttttttaa aattcctatt 480 ttgttgcccg atggaataca gttgaatgca gaattcaatt ctaatgacac ggagaaaaag 540
acaacagatg atattaaaac gcttacagct tctcctcaaa acatcaaagt tccagctgga 600
aaaacttata aagtagaagt aactctacat aaaaagaact ttgtagggga tatagatttt 660
caaggaaaag caacaaatgt aaaatcagac ctgaatgtac gtgaaatgta tcttggacct 720
ggatttcctc gaccagatag atatccaact tatacatacg atacagcaga catgtggaaa 780
gatttaacga atgatcaaaa aaatcaaatt acaggtatta aatttgatga taataagaat 840
ttgatactaa acggaacagc taaattaaaa ggaatttatg gtagtaagtt gcaagtaaat 900
atttttgata ttacaaataa atccactcct aaattagtac aagtatttta a 951

<210> SEQ ID NO 8
<211> LENGTH: 316
<212> TYPE: PRT
<213> ORGANISM: Bacillus thuringiensis
<220> FEATURE:
<221> NAME/KEY: MISC_FEATURE
<222> LOCATION: (1)..(316)
<223> OTHER INFORMATION: precursor TIC3037; Bt CFB 202735
<220> FEATURE:
<221> NAME/KEY: MISC_FEATURE
<222> LOCATION: (1)..(31)
<223> OTHER INFORMATION: signal peptide amino acid sequence
<220> FEATURE:
<221> NAME/KEY: MISC_FEATURE
<222> LOCATION: (32)..(316)
<223> OTHER INFORMATION: mature peptide amino acid sequence

<400> SEQUENCE: 8

Met Lys Asn Lys Lys Asn Ile Phe Lys Met Cys Ser Ala Thr Leu Ala
1 5 10 15

```
Leu Ser Leu Gly Val Thr Val Phe Val Pro Thr Ala Ser Tyr Ala Ala
            20                  25                  30

Ile Thr Asn Asp Lys Phe Leu Ser Pro Val Thr Ser Thr Asp Ser Asn
        35                  40                  45

Ile Thr Asn Val Asp Asp Ser Met Asn Lys Thr Ser Asp Phe Tyr Tyr
    50                  55                  60

Lys Asn Lys Leu Asp Asn Lys Glu Leu Gly Ser Tyr Trp Arg Ile Asn
65                  70                  75                  80

Ser Leu Gln Ser Lys Lys Thr Thr Met Asp Leu Glu Ile Asn Ser Ser
                85                  90                  95

Asp Ile Gln Asn Leu Lys Tyr Ser Asp Ser Gln Pro Glu Tyr Ile Gly
            100                 105                 110

Glu Asn Glu Phe Lys Asn Asp Thr Asn Glu Glu Gln Ile Met Thr Thr
        115                 120                 125

Ala Thr Tyr Ser His Glu Val Arg Asn Phe Val Asp Ser Thr Val Thr
    130                 135                 140

Lys Gly Phe Gln Ala Lys Gly Glu Gly Ala Phe Phe Lys Ile Pro Ile
145                 150                 155                 160

Leu Leu Pro Asp Gly Ile Gln Leu Asn Ala Glu Phe Asn Ser Asn Asp
                165                 170                 175

Thr Glu Lys Lys Thr Thr Asp Asp Ile Lys Thr Leu Thr Ala Ser Pro
            180                 185                 190

Gln Asn Ile Lys Val Pro Ala Gly Lys Thr Tyr Lys Val Glu Val Thr
        195                 200                 205

Leu His Lys Lys Asn Phe Val Gly Asp Ile Asp Phe Gln Gly Lys Ala
    210                 215                 220

Thr Asn Val Lys Ser Asp Leu Asn Val Arg Glu Met Tyr Leu Gly Pro
225                 230                 235                 240

Gly Phe Pro Arg Pro Asp Arg Tyr Pro Thr Tyr Thr Tyr Asp Thr Ala
                245                 250                 255

Asp Met Trp Lys Asp Leu Thr Asn Asp Gln Lys Asn Gln Ile Thr Gly
            260                 265                 270

Ile Lys Phe Asp Asp Asn Lys Asn Leu Ile Leu Asn Gly Thr Ala Lys
        275                 280                 285

Leu Lys Gly Ile Tyr Gly Ser Lys Leu Gln Val Asn Ile Phe Asp Ile
    290                 295                 300

Thr Asn Lys Ser Thr Pro Lys Leu Val Gln Val Phe
305                 310                 315
```

<210> SEQ ID NO 9
<211> LENGTH: 981
<212> TYPE: DNA
<213> ORGANISM: Bacillus thuringiensis
<220> FEATURE:
<221> NAME/KEY: misc_feature
<222> LOCATION: (1)..(978)
<223> OTHER INFORMATION: Open Reading Frame TIC2228; Bt EG9095
<220> FEATURE:
<221> NAME/KEY: misc_feature
<222> LOCATION: (1)..(78)
<223> OTHER INFORMATION: signal peptide coding sequence
<220> FEATURE:
<221> NAME/KEY: misc_feature
<222> LOCATION: (79)..(978)
<223> OTHER INFORMATION: mature peptide coding sequence

<400> SEQUENCE: 9

```
atgagaaaaa aattaattgt aacaacagca tcattatctc tagctttaac aagttttggg     60
```

-continued

```
tccatcacat ctttggctga aagtaacaat caacaaaata aaaggattga agtaaatgga    120

actacttcca attcatctat tttaagccca attacatcta atatcattac agatgttgat    180

caacaaatga ataaaatttc agattattat tataataata atctgaaatt aaaagacata    240

ggggactatt atcacattat tcgactagaa aataaaaata ctactatgtc ttttagtctg    300

aatgctgatg atataaaaaa tttgcaatat aatgatttgc agccacaata tataggtgag    360

aatgaattta aaaatactac agatcaagaa caaacattta cgacagcatc gtattcacaa    420

gcagttacaa attctgtgag ttctactgtt attcaaggat ttaaggcaac aagcactacg    480

agtctattga aaattcctat cctcttacca gaaggaataa acttaaatgc agaattcaac    540

tctgcttcaa atacaacaac tacaaataca acaactgaaa cccttacagc tccaccgcaa    600

aatattaaag tgccatcagg tagaacttat aaagtagaag taaatctatt aaagaaaaaa    660

ttcacaggtg atatagattt tcatggaaaa ggaacagatg taaaatcaaa tttaaaagta    720

cgcgcaacat attatggtcc tggattccca cgtcctacta aatatcctag ctatacatat    780

tctacagcgg atatgtggag aggtctaaca actgagcaaa aaaaacaaat tactggtgtt    840

aattttaata acaacaaaga tttaacgata gatggtacta caaaagtgga agggatttat    900

ggcagcaatt tagaagtagt tgtttatgat ataacaaata aaaatattcc taaaatggta    960

gaaactagaa catttaaatg a                                               981
```

<210> SEQ ID NO 10
<211> LENGTH: 326
<212> TYPE: PRT
<213> ORGANISM: Bacillus thuringiensis
<220> FEATURE:
<221> NAME/KEY: MISC_FEATURE
<222> LOCATION: (1)..(326)
<223> OTHER INFORMATION: precursor TIC2228; Bt EG9095
<220> FEATURE:
<221> NAME/KEY: MISC_FEATURE
<222> LOCATION: (1)..(26)
<223> OTHER INFORMATION: signal peptide amino acid sequence
<220> FEATURE:
<221> NAME/KEY: MISC_FEATURE
<222> LOCATION: (27)..(326)
<223> OTHER INFORMATION: mature peptide amino acid sequence

<400> SEQUENCE: 10

```
Met Arg Lys Lys Leu Ile Val Thr Thr Ala Ser Leu Ser Leu Ala Leu
1               5                   10                  15

Thr Ser Phe Gly Ser Ile Thr Ser Leu Ala Glu Ser Asn Asn Gln Gln
            20                  25                  30

Asn Lys Arg Ile Glu Val Asn Gly Thr Thr Ser Asn Ser Ser Ile Leu
        35                  40                  45

Ser Pro Ile Thr Ser Asn Ile Ile Thr Asp Val Asp Gln Gln Met Asn
    50                  55                  60

Lys Ile Ser Asp Tyr Tyr Tyr Asn Asn Asn Leu Lys Leu Lys Asp Ile
65                  70                  75                  80

Gly Asp Tyr Tyr His Ile Ile Arg Leu Glu Asn Lys Asn Thr Thr Met
                85                  90                  95

Ser Phe Ser Leu Asn Ala Asp Asp Ile Lys Asn Leu Gln Tyr Asn Asp
            100                 105                 110

Leu Gln Pro Gln Tyr Ile Gly Glu Asn Glu Phe Lys Asn Thr Thr Asp
        115                 120                 125

Gln Glu Gln Thr Phe Thr Thr Ala Ser Tyr Ser Gln Ala Val Thr Asn
    130                 135                 140
```

-continued

```
Ser Val Ser Ser Thr Val Ile Gln Gly Phe Lys Ala Thr Ser Thr Thr
145                 150                 155                 160

Ser Leu Leu Lys Ile Pro Ile Leu Leu Pro Glu Gly Ile Asn Leu Asn
                165                 170                 175

Ala Glu Phe Asn Ser Ala Ser Asn Thr Thr Thr Thr Asn Thr Thr Thr
            180                 185                 190

Glu Thr Leu Thr Ala Pro Pro Gln Asn Ile Lys Val Pro Ser Gly Arg
        195                 200                 205

Thr Tyr Lys Val Glu Val Asn Leu Leu Lys Lys Lys Phe Thr Gly Asp
    210                 215                 220

Ile Asp Phe His Gly Lys Gly Thr Asp Val Lys Ser Asn Leu Lys Val
225                 230                 235                 240

Arg Ala Thr Tyr Tyr Gly Pro Gly Phe Pro Arg Pro Thr Lys Tyr Pro
                245                 250                 255

Ser Tyr Thr Tyr Ser Thr Ala Asp Met Trp Arg Gly Leu Thr Thr Glu
            260                 265                 270

Gln Lys Lys Gln Ile Thr Gly Val Asn Phe Asn Asn Asn Lys Asp Leu
        275                 280                 285

Thr Ile Asp Gly Thr Thr Lys Val Glu Gly Ile Tyr Gly Ser Asn Leu
    290                 295                 300

Glu Val Val Val Tyr Asp Ile Thr Asn Lys Asn Ile Pro Lys Met Val
305                 310                 315                 320

Glu Thr Arg Thr Phe Lys
                325


<210> SEQ ID NO 11
<211> LENGTH: 945
<212> TYPE: DNA
<213> ORGANISM: Bacillus thuringiensis
<220> FEATURE:
<221> NAME/KEY: misc_feature
<222> LOCATION: (1)..(942)
<223> OTHER INFORMATION: Open Reading Frame TIC3005; Bt CFB 005050
<220> FEATURE:
<221> NAME/KEY: misc_feature
<222> LOCATION: (1)..(99)
<223> OTHER INFORMATION: signal peptide coding sequence
<220> FEATURE:
<221> NAME/KEY: misc_feature
<222> LOCATION: (100)..(942)
<223> OTHER INFORMATION: mature peptide coding sequence

<400> SEQUENCE: 11

atgaagactc tatttaagat aaaaaaaact tttataacca agctagggat tatattagga      60

atatcaagta ccatgttttt tggaaataat gtcatggcag ctcaagccgc aaatattata     120

gatgtagacg cacaaatgga taaaatttcc gatttttatt ttaaaagtga attaaaatgg     180

aaagatgtag cggatttccc tggagcatat cattatatta gattggatag taaaaaaaca     240

aatatggatt tagatctaaa aacaagcaat ttaaaaaact taacatatag tgatttaaat     300

ccagaatata ttggtgaaaa tgaatttgat aatacaaatg gagttacaga gcaaacattc     360

acaacagcat ggtattccca tcaagttacg aactccgcta gtacaagtgt tactgaagga     420

tttaaaatag gaggaaaaac aacactcttt aaattaccta ttttattaac aggtggtatt     480

gatattactg cagaattcaa ttctgcaaca agtaaaacaa atacagttac agacactaaa     540

actttaactg cttcaccaca aaatataaaa gttccagctg gtaaaaaata tttagtcaaa     600

gtgaatatgg ctaaaaaaac atttaatgga gatatagact ttagggcaaa tggacaaaat     660

gtaaaatcaa cacttaacac gttagcaact tattatggac cgggattccc acgtccagat     720
```

```
aaatgttcat cacttacatt tacaacggca gacatatggg aaaagttatc tgctaattca    780

caaaatcaaa taaagggagt taattttgat tctaataaaa atcttatatt gaatggaaaa    840

gcacatataa atggaatttt tggaagtaca ctaagtgtga gtatttatga tattacagct    900

tcaaaaaaat cacctaaact aattcagcaa aaaaacatgg gataa                      945


<210> SEQ ID NO 12
<211> LENGTH: 314
<212> TYPE: PRT
<213> ORGANISM: Bacillus thuringiensis
<220> FEATURE:
<221> NAME/KEY: MISC_FEATURE
<222> LOCATION: (1)..(314)
<223> OTHER INFORMATION: precursor TIC3005; Bt CFB 005050
<220> FEATURE:
<221> NAME/KEY: MISC_FEATURE
<222> LOCATION: (1)..(33)
<223> OTHER INFORMATION: signal peptide amino acid sequence
<220> FEATURE:
<221> NAME/KEY: MISC_FEATURE
<222> LOCATION: (34)..(314)
<223> OTHER INFORMATION: mature peptide amino acid sequence

<400> SEQUENCE: 12

Met Lys Thr Leu Phe Lys Ile Lys Lys Thr Phe Ile Thr Lys Leu Gly
1               5                   10                  15

Ile Ile Leu Gly Ile Ser Ser Thr Met Phe Phe Gly Asn Asn Val Met
            20                  25                  30

Ala Ala Gln Ala Ala Asn Ile Ile Asp Val Asp Ala Gln Met Asp Lys
        35                  40                  45

Ile Ser Asp Phe Tyr Phe Lys Ser Glu Leu Lys Trp Lys Asp Val Ala
    50                  55                  60

Asp Phe Pro Gly Ala Tyr His Tyr Ile Arg Leu Asp Ser Lys Lys Thr
65                  70                  75                  80

Asn Met Asp Leu Asp Leu Lys Thr Ser Asn Leu Lys Asn Leu Thr Tyr
                85                  90                  95

Ser Asp Leu Asn Pro Glu Tyr Ile Gly Glu Asn Glu Phe Asp Asn Thr
            100                 105                 110

Asn Gly Val Thr Glu Gln Thr Phe Thr Thr Ala Trp Tyr Ser His Gln
        115                 120                 125

Val Thr Asn Ser Ala Ser Thr Ser Val Thr Glu Gly Phe Lys Ile Gly
    130                 135                 140

Gly Lys Thr Thr Leu Phe Lys Leu Pro Ile Leu Leu Thr Gly Gly Ile
145                 150                 155                 160

Asp Ile Thr Ala Glu Phe Asn Ser Ala Thr Ser Lys Thr Asn Thr Val
                165                 170                 175

Thr Asp Thr Lys Thr Leu Thr Ala Ser Pro Gln Asn Ile Lys Val Pro
            180                 185                 190

Ala Gly Lys Lys Tyr Leu Val Lys Val Asn Met Ala Lys Lys Thr Phe
        195                 200                 205

Asn Gly Asp Ile Asp Phe Arg Ala Asn Gly Gln Asn Val Lys Ser Thr
    210                 215                 220

Leu Asn Thr Leu Ala Thr Tyr Tyr Gly Pro Gly Phe Pro Arg Pro Asp
225                 230                 235                 240

Lys Cys Ser Ser Leu Thr Phe Thr Thr Ala Asp Ile Trp Glu Lys Leu
                245                 250                 255

Ser Ala Asn Ser Gln Asn Gln Ile Lys Gly Val Asn Phe Asp Ser Asn
            260                 265                 270
```

Lys Asn Leu Ile Leu Asn Gly Lys Ala His Ile Asn Gly Ile Phe Gly
        275                 280                 285

Ser Thr Leu Ser Val Ser Ile Tyr Asp Ile Thr Ala Ser Lys Lys Ser
    290                 295                 300

Pro Lys Leu Ile Gln Gln Lys Asn Met Gly
305                 310

<210> SEQ ID NO 13
<211> LENGTH: 942
<212> TYPE: DNA
<213> ORGANISM: Bacillus thuringiensis
<220> FEATURE:
<221> NAME/KEY: misc_feature
<222> LOCATION: (1)..(939)
<223> OTHER INFORMATION: Open Reading Frame TIC2593; Bt EG3855
<220> FEATURE:
<221> NAME/KEY: misc_feature
<222> LOCATION: (1)..(99)
<223> OTHER INFORMATION: signal peptide coding sequence
<220> FEATURE:
<221> NAME/KEY: misc_feature
<222> LOCATION: (100)..(939)
<223> OTHER INFORMATION: mature peptide coding sequence

<400> SEQUENCE: 13
atgaagattc tatggaaacc ccaaaaaact tttatttcca acctagcgat tgtattggga 60
atttcaagta ccctgttttt tggaagtaat gtcatggcag atcaaacagc aaatattaca 120
gatgtagatg cacaaatgga caagatttca gatttttatt ttaaaaacga gttagaatgg 180
aaagatttac ctgaatatcc tggagcatat cattatatta gattggatag taaaaaaaca 240
aatatggatt tagatttaaa agcgaacaat ataaaaaatt taacttatag tgagttaaat 300
ccagaatatg tcggtgaaaa tgaatttgat aatacaaata gtaatataga ccaaacattc 360
acaacagcgg cctattccca tcaagttaca aactcggcta gtacaaatgt tactaaaggg 420
tttaaagtgg gcggaaaaac aacgcttctt aaattaccga ttttattaac aagtggagtt 480
gagattaatg cagaatttaa ctctgcaaca agtacgacga atacagttac agataccaag 540
actttaactg cttctccaca aaatataaag gttccagccg gtaggaagtt tctagttaaa 600
gtagatatgg ccaaaaaaac atttaatgga gaagtagact ttagtgcaac aggatataat 660
gtaaaatcaa cgcttaacac gttagcaact tattatgcag cagggttccc acgtccaaat 720
aaatatccat cacttacatt tgtcacagca gatatgtgga aaaagttatc tactagtcaa 780
caaaatcaaa taaatggagt taattttgat tctagtaaag atcttgtgtt aaatgggaaa 840
gcgaatgtac atgggatttt tggaagtaca ctacgtgtga gcgtttatga tattacagat 900
tcaaaattat cacctaaact agttcaacat aaaaacatat ga 942

<210> SEQ ID NO 14
<211> LENGTH: 313
<212> TYPE: PRT
<213> ORGANISM: Bacillus thuringiensis
<220> FEATURE:
<221> NAME/KEY: MISC_FEATURE
<222> LOCATION: (1)..(313)
<223> OTHER INFORMATION: precursor TIC2593; Bt EG3855
<220> FEATURE:
<221> NAME/KEY: MISC_FEATURE
<222> LOCATION: (1)..(33)
<223> OTHER INFORMATION: signal peptide amino acid sequence
<220> FEATURE:
<221> NAME/KEY: MISC_FEATURE
<222> LOCATION: (34)..(313)
<223> OTHER INFORMATION: mature peptide amino acid sequence

<400> SEQUENCE: 14

Met Lys Ile Leu Trp Lys Pro Gln Lys Thr Phe Ile Ser Asn Leu Ala
1 5 10 15

Ile Val Leu Gly Ile Ser Ser Thr Leu Phe Phe Gly Ser Asn Val Met
20 25 30

Ala Asp Gln Thr Ala Asn Ile Thr Asp Val Asp Ala Gln Met Asp Lys
35 40 45

Ile Ser Asp Phe Tyr Phe Lys Asn Glu Leu Glu Trp Lys Asp Leu Pro
50 55 60

Glu Tyr Pro Gly Ala Tyr His Tyr Ile Arg Leu Asp Ser Lys Lys Thr
65 70 75 80

Asn Met Asp Leu Asp Leu Lys Ala Asn Asn Ile Lys Asn Leu Thr Tyr
85 90 95

Ser Glu Leu Asn Pro Glu Tyr Val Gly Glu Asn Glu Phe Asp Asn Thr
100 105 110

Asn Ser Asn Ile Asp Gln Thr Phe Thr Thr Ala Ala Tyr Ser His Gln
115 120 125

Val Thr Asn Ser Ala Ser Thr Asn Val Thr Lys Gly Phe Lys Val Gly
130 135 140

Gly Lys Thr Thr Leu Leu Lys Leu Pro Ile Leu Leu Thr Ser Gly Val
145 150 155 160

Glu Ile Asn Ala Glu Phe Asn Ser Ala Thr Ser Thr Thr Asn Thr Val
165 170 175

Thr Asp Thr Lys Thr Leu Thr Ala Ser Pro Gln Asn Ile Lys Val Pro
180 185 190

Ala Gly Arg Lys Phe Leu Val Lys Val Asp Met Ala Lys Lys Thr Phe
195 200 205

Asn Gly Glu Val Asp Phe Ser Ala Thr Gly Tyr Asn Val Lys Ser Thr
210 215 220

Leu Asn Thr Leu Ala Thr Tyr Tyr Ala Ala Gly Phe Pro Arg Pro Asn
225 230 235 240

Lys Tyr Pro Ser Leu Thr Phe Val Thr Ala Asp Met Trp Lys Lys Leu
245 250 255

Ser Thr Ser Gln Gln Asn Gln Ile Asn Gly Val Asn Phe Asp Ser Ser
260 265 270

Lys Asp Leu Val Leu Asn Gly Lys Ala Asn Val His Gly Ile Phe Gly
275 280 285

Ser Thr Leu Arg Val Ser Val Tyr Asp Ile Thr Asp Ser Lys Leu Ser
290 295 300

Pro Lys Leu Val Gln His Lys Asn Ile
305 310

<210> SEQ ID NO 15
<211> LENGTH: 942
<212> TYPE: DNA
<213> ORGANISM: Bacillus thuringiensis
<220> FEATURE:
<221> NAME/KEY: misc_feature
<222> LOCATION: (1)..(939)
<223> OTHER INFORMATION: Open Reading Frame TIC2598; Bt EG4492
<220> FEATURE:
<221> NAME/KEY: misc_feature
<222> LOCATION: (1)..(99)
<223> OTHER INFORMATION: signal peptide coding sequence
<220> FEATURE:
<221> NAME/KEY: misc_feature
<222> LOCATION: (100)..(939)

-continued

<223> OTHER INFORMATION: mature peptide coding sequence

<400> SEQUENCE: 15
atgaagattc tatggaaacc ccaaaaagct tttatttcca acctagcgat tgtattggga 60
atttcaagta ccctgttttt tggaagtaat gtcatggcag atcaaacagc aaatattaca 120
gatgtagatg cacaaatgga caagatttca gatttttatt ttaaaaacga gttagaatgg 180
aaatatttac ctgaatatcc tggagcatat cattatatta gattggatag taaaaaaaca 240
aatatggatt tagatttaaa agcgaacaat ataaaaaatt taatttatag tgatttaaat 300
ccagaatatg tcggtgaaaa tgaatttgat aatacacata gtaatataga ccaaacattc 360
acaacagcag cctattccca tcaagttaca aactcggcta gtacaaatgt tactaaaggg 420
tttaaagtgg gcggaaaaac aacgcttcta aaattaccga ttttattaac aagtggagtt 480
gagattaatg cagaatttaa ctctgcaaca agtacgacga atacagttac agataccaag 540
acattaactg cttctccaca aaatataaag gttccagctg gtaggaagtt tctagttaaa 600
gtagatatgg ccaaaaaaac atttaatgga gaagtagact ttagtgcaac aggatataat 660
gtaaaatcaa cgcttaacac gttagcaact tattatgccg cagggtttcc acgtccaaat 720
aaatatccat cacttacatt tgtcacagca gatatgtgga aaaagttatc tactagtcaa 780
caaaatcaaa taaatggagt taattttgat tctagtaaag atcttgtgtt aaatgggaaa 840
gcgaatgtac atggaatttt tggaagtaca ctacgtgtga gcgtttatga tattaccgat 900
ccaaaattat cacctaaact agttcaacaa aaaaacatat aa 942

<210> SEQ ID NO 16
<211> LENGTH: 313
<212> TYPE: PRT
<213> ORGANISM: Bacillus thuringiensis
<220> FEATURE:
<221> NAME/KEY: MISC_FEATURE
<222> LOCATION: (1)..(313)
<223> OTHER INFORMATION: precursor TIC2598; Bt EG4492
<220> FEATURE:
<221> NAME/KEY: MISC_FEATURE
<222> LOCATION: (1)..(33)
<223> OTHER INFORMATION: signal peptide amino acid sequence
<220> FEATURE:
<221> NAME/KEY: MISC_FEATURE
<222> LOCATION: (34)..(313)
<223> OTHER INFORMATION: mature peptide amino acid sequence

<400> SEQUENCE: 16

```
Met Lys Ile Leu Trp Lys Pro Gln Lys Ala Phe Ile Ser Asn Leu Ala
1               5                   10                  15

Ile Val Leu Gly Ile Ser Ser Thr Leu Phe Phe Gly Ser Asn Val Met
            20                  25                  30

Ala Asp Gln Thr Ala Asn Ile Thr Asp Val Asp Ala Gln Met Asp Lys
        35                  40                  45

Ile Ser Asp Phe Tyr Phe Lys Asn Glu Leu Glu Trp Lys Tyr Leu Pro
    50                  55                  60

Glu Tyr Pro Gly Ala Tyr His Tyr Ile Arg Leu Asp Ser Lys Lys Thr
65                  70                  75                  80

Asn Met Asp Leu Asp Leu Lys Ala Asn Asn Ile Lys Asn Leu Ile Tyr
                85                  90                  95

Ser Asp Leu Asn Pro Glu Tyr Val Gly Glu Asn Glu Phe Asp Asn Thr
            100                 105                 110

His Ser Asn Ile Asp Gln Thr Phe Thr Thr Ala Ala Tyr Ser His Gln
        115                 120                 125
```

-continued

```
Val Thr Asn Ser Ala Ser Thr Asn Val Thr Lys Gly Phe Lys Val Gly
    130                 135                 140

Gly Lys Thr Thr Leu Leu Lys Leu Pro Ile Leu Leu Thr Ser Gly Val
145                 150                 155                 160

Glu Ile Asn Ala Glu Phe Asn Ser Ala Thr Ser Thr Thr Asn Thr Val
                165                 170                 175

Thr Asp Thr Lys Thr Leu Thr Ala Ser Pro Gln Asn Ile Lys Val Pro
            180                 185                 190

Ala Gly Arg Lys Phe Leu Val Lys Val Asp Met Ala Lys Lys Thr Phe
        195                 200                 205

Asn Gly Glu Val Asp Phe Ser Ala Thr Gly Tyr Asn Val Lys Ser Thr
    210                 215                 220

Leu Asn Thr Leu Ala Thr Tyr Tyr Ala Ala Gly Phe Pro Arg Pro Asn
225                 230                 235                 240

Lys Tyr Pro Ser Leu Thr Phe Val Thr Ala Asp Met Trp Lys Lys Leu
                245                 250                 255

Ser Thr Ser Gln Gln Asn Gln Ile Asn Gly Val Asn Phe Asp Ser Ser
            260                 265                 270

Lys Asp Leu Val Leu Asn Gly Lys Ala Asn Val His Gly Ile Phe Gly
        275                 280                 285

Ser Thr Leu Arg Val Ser Val Tyr Asp Ile Thr Asp Pro Lys Leu Ser
    290                 295                 300

Pro Lys Leu Val Gln Gln Lys Asn Ile
305                 310
```

<210> SEQ ID NO 17
<211> LENGTH: 1014
<212> TYPE: DNA
<213> ORGANISM: Bacillus thuringiensis
<220> FEATURE:
<221> NAME/KEY: misc_feature
<222> LOCATION: (1)..(1011)
<223> OTHER INFORMATION: Open Reading Frame TIC3891; Bt EG4227
<220> FEATURE:
<221> NAME/KEY: misc_feature
<222> LOCATION: (1)..(84)
<223> OTHER INFORMATION: signal peptide coding sequence
<220> FEATURE:
<221> NAME/KEY: misc_feature
<222> LOCATION: (85)..(1011)
<223> OTHER INFORMATION: mature peptide coding sequence

<400> SEQUENCE: 17

```
atgaaactaa aaagtatatt taaatgtgtc acaattaccg cagtattatc ccagattgct      60

gtatatccag taacatctta tgcagtaagc aacattgaac agaattctga caataagaaa     120

ataacggaag aaaaaagcga tatgttagga aatggttcac tattaaatgt tcatgaatcc     180

tctgtaaaag cagcctattc ttctaatgtt actaatgttg acgaacagat gaacaaaatt     240

tctgattttt attatcagaa taaccttgca tggaaagaaa tctctactta ctatttggta     300

gaccaattaa aagaaaaaaa gactactatg tccttagatc ttaacgcctc tgatataaat     360

aacttaacat ataatgactt acaaccagaa tatataggtg aaaacgaatt tgaaaataaa     420

acggatcagg aacaaacatt tactacagca ccctattctc atacagttac agacactgta     480

agttctactg ttacgaatgg atttaaaatc ggaggtagtg gagatactat tttcaaaatt     540

cctattttat taaaagatgg aataaaactg agtgcagaat tcaattcagc tacaagtaca     600

acaaatacaa ctacagatac gaagactctt acagctcctt ctcaaaacat caaggtacca     660
```

-continued

```
gccggtaaaa cctacaaggt ggaagtaaac ctacaaaaga agaacttcgc aggagatata    720

gacttcactg gaaaagcaac caatgtaaat tcaaaattaa cagtaaatgc agcatatgtt    780

ggtcctggat tccctcgact tgataaagag cagtccttca catatgctac agcagacatg    840

tggaaagatt taacgaatga tcaacgaaat caaattaccg gaatctcctt tgataataat    900

aagaatttaa cacttaatgg taaagcaaaa atagagggta tttatggaag taaattacaa    960

gtgagtgttt atgatattac aaataatgct catagattag tacaagtatt ctaa         1014
```

```
<210> SEQ ID NO 18
<211> LENGTH: 337
<212> TYPE: PRT
<213> ORGANISM: Bacillus thuringiensis
<220> FEATURE:
<221> NAME/KEY: MISC_FEATURE
<222> LOCATION: (1)..(337)
<223> OTHER INFORMATION: precursor TIC3891; BT EG4227
<220> FEATURE:
<221> NAME/KEY: MISC_FEATURE
<222> LOCATION: (1)..(28)
<223> OTHER INFORMATION: signal peptide amino acid sequence
<220> FEATURE:
<221> NAME/KEY: MISC_FEATURE
<222> LOCATION: (29)..(337)
<223> OTHER INFORMATION: mature peptide amino acid sequence

<400> SEQUENCE: 18

Met Lys Leu Lys Ser Ile Phe Lys Cys Val Thr Ile Thr Ala Val Leu
1               5                   10                  15

Ser Gln Ile Ala Val Tyr Pro Val Thr Ser Tyr Ala Val Ser Asn Ile
            20                  25                  30

Glu Gln Asn Ser Asp Asn Lys Lys Ile Thr Glu Glu Lys Ser Asp Met
        35                  40                  45

Leu Gly Asn Gly Ser Leu Leu Asn Val His Glu Ser Ser Val Lys Ala
    50                  55                  60

Ala Tyr Ser Ser Asn Val Thr Asn Val Asp Glu Gln Met Asn Lys Ile
65                  70                  75                  80

Ser Asp Phe Tyr Tyr Gln Asn Asn Leu Ala Trp Lys Glu Ile Ser Thr
                85                  90                  95

Tyr Tyr Leu Val Asp Gln Leu Lys Glu Lys Lys Thr Thr Met Ser Leu
            100                 105                 110

Asp Leu Asn Ala Ser Asp Ile Asn Asn Leu Thr Tyr Asn Asp Leu Gln
        115                 120                 125

Pro Glu Tyr Ile Gly Glu Asn Glu Phe Glu Asn Lys Thr Asp Gln Glu
    130                 135                 140

Gln Thr Phe Thr Thr Ala Pro Tyr Ser His Thr Val Thr Asp Thr Val
145                 150                 155                 160

Ser Ser Thr Val Thr Asn Gly Phe Lys Ile Gly Gly Ser Gly Asp Thr
                165                 170                 175

Ile Phe Lys Ile Pro Ile Leu Leu Lys Asp Gly Ile Lys Leu Ser Ala
            180                 185                 190

Glu Phe Asn Ser Ala Thr Ser Thr Thr Asn Thr Thr Thr Asp Thr Lys
        195                 200                 205

Thr Leu Thr Ala Pro Ser Gln Asn Ile Lys Val Pro Ala Gly Lys Thr
    210                 215                 220

Tyr Lys Val Glu Val Asn Leu Gln Lys Lys Asn Phe Ala Gly Asp Ile
225                 230                 235                 240

Asp Phe Thr Gly Lys Ala Thr Asn Val Asn Ser Lys Leu Thr Val Asn
                245                 250                 255
```

```
Ala Ala Tyr Val Gly Pro Gly Phe Pro Arg Leu Asp Lys Glu Gln Ser
            260                 265                 270

Phe Thr Tyr Ala Thr Ala Asp Met Trp Lys Asp Leu Thr Asn Asp Gln
        275                 280                 285

Arg Asn Gln Ile Thr Gly Ile Ser Phe Asp Asn Asn Lys Asn Leu Thr
    290                 295                 300

Leu Asn Gly Lys Ala Lys Ile Glu Gly Ile Tyr Gly Ser Lys Leu Gln
305                 310                 315                 320

Val Ser Val Tyr Asp Ile Thr Asn Asn Ala His Arg Leu Val Gln Val
                325                 330                 335

Phe

<210> SEQ ID NO 19
<211> LENGTH: 1014
<212> TYPE: DNA
<213> ORGANISM: Bacillus thuringiensis
<220> FEATURE:
<221> NAME/KEY: misc_feature
<222> LOCATION: (1)..(1011)
<223> OTHER INFORMATION: Open Reading Frame TIC3090; Bt EG5554
<220> FEATURE:
<221> NAME/KEY: misc_feature
<222> LOCATION: (1)..(84)
<223> OTHER INFORMATION: signal peptide coding sequence
<220> FEATURE:
<221> NAME/KEY: misc_feature
<222> LOCATION: (85)..(1011)
<223> OTHER INFORMATION: mature peptide coding sequence

<400> SEQUENCE: 19
atgaaactaa aaagtatatt taaatgtgtc acaattaccg cagtattatc ccagattgct      60
gtatatccag taacatctta tgcagtaagc aacattgaac agaattctga caataagaaa     120
ataacggaag aaaaaagtga tatgttagga aatagtttac tattaaatgt tcacgaatcc     180
tctgtaaaag cagcctattc ttcaaatatt actaacgttg acgaacagat gaacaaaatt     240
tctgattttt attatcaaaa taaccttgca tggaaagaaa tctctactaa ctttttggta     300
gacagattaa aagaaaaaaa gactactatg tccttagatc ttaacgcctc tgatataaat     360
aacttaacat ataatgactt acaaccagaa tatataggtg aaaacgaatt tgaaaataca     420
acggatcagg aacaaacatt tactacagca tcctattctc atacagttac tgacactgta     480
agttctactg ttacgaatgg atttaaaatc ggaggtagtg gagatactat tttcaaaatt     540
cctattttat taaaagatgg aataaaactg agtgcagaat tcaattccgc tacgagtaca     600
acgaacacaa ctacagatac gaagactctt acagcttctc ctcaaagcat taaggtacca     660
gctggtaaga cgtacaaagt ggtagtaaac ctacaaaaga agaacttcac aggagatata     720
gacttcactg gaaaagcaac caatgtaaat tcaacattaa cagtaaatgt agcatatgtt     780
ggtcctggat tccctcgacc tgataaagag cagtccttca catatgctac agcagacatg     840
tggaaagatt taacgaatga tcaacgaaat caaattaccg gaatctcctt tgataataat     900
aagaatttaa cgcttaatgg taaagcaaaa atagagggta tttatggaag taaattacga     960
gtgagtgttt atgatattac aaataatgct catagattag tacaagtatt ctaa          1014

<210> SEQ ID NO 20
<211> LENGTH: 337
<212> TYPE: PRT
<213> ORGANISM: Bacillus thuringiensis
<220> FEATURE:
<221> NAME/KEY: MISC_FEATURE
```

<222> LOCATION: (1)..(337)
<223> OTHER INFORMATION: precursor TIC3090; Bt EG5554
<220> FEATURE:
<221> NAME/KEY: MISC_FEATURE
<222> LOCATION: (1)..(28)
<223> OTHER INFORMATION: signal peptide amino acid sequence
<220> FEATURE:
<221> NAME/KEY: MISC_FEATURE
<222> LOCATION: (29)..(337)
<223> OTHER INFORMATION: mature peptide amino acid sequence

<400> SEQUENCE: 20

```
Met Lys Leu Lys Ser Ile Phe Lys Cys Val Thr Ile Thr Ala Val Leu
1               5                   10                  15

Ser Gln Ile Ala Val Tyr Pro Val Thr Ser Tyr Ala Val Ser Asn Ile
            20                  25                  30

Glu Gln Asn Ser Asp Asn Lys Lys Ile Thr Glu Glu Lys Ser Asp Met
        35                  40                  45

Leu Gly Asn Ser Leu Leu Leu Asn Val His Glu Ser Ser Val Lys Ala
    50                  55                  60

Ala Tyr Ser Ser Asn Ile Thr Asn Val Asp Glu Gln Met Asn Lys Ile
65                  70                  75                  80

Ser Asp Phe Tyr Tyr Gln Asn Asn Leu Ala Trp Lys Glu Ile Ser Thr
                85                  90                  95

Asn Phe Leu Val Asp Arg Leu Lys Glu Lys Lys Thr Thr Met Ser Leu
            100                 105                 110

Asp Leu Asn Ala Ser Asp Ile Asn Asn Leu Thr Tyr Asn Asp Leu Gln
        115                 120                 125

Pro Glu Tyr Ile Gly Glu Asn Glu Phe Glu Asn Thr Thr Asp Gln Glu
    130                 135                 140

Gln Thr Phe Thr Thr Ala Ser Tyr Ser His Thr Val Thr Asp Thr Val
145                 150                 155                 160

Ser Ser Thr Val Thr Asn Gly Phe Lys Ile Gly Gly Ser Gly Asp Thr
                165                 170                 175

Ile Phe Lys Ile Pro Ile Leu Leu Lys Asp Gly Ile Lys Leu Ser Ala
            180                 185                 190

Glu Phe Asn Ser Ala Thr Ser Thr Thr Asn Thr Thr Thr Asp Thr Lys
        195                 200                 205

Thr Leu Thr Ala Ser Pro Gln Ser Ile Lys Val Pro Ala Gly Lys Thr
    210                 215                 220

Tyr Lys Val Val Val Asn Leu Gln Lys Lys Asn Phe Thr Gly Asp Ile
225                 230                 235                 240

Asp Phe Thr Gly Lys Ala Thr Asn Val Asn Ser Thr Leu Thr Val Asn
                245                 250                 255

Val Ala Tyr Val Gly Pro Gly Phe Pro Arg Pro Asp Lys Glu Gln Ser
            260                 265                 270

Phe Thr Tyr Ala Thr Ala Asp Met Trp Lys Asp Leu Thr Asn Asp Gln
        275                 280                 285

Arg Asn Gln Ile Thr Gly Ile Ser Phe Asp Asn Asn Lys Asn Leu Thr
    290                 295                 300

Leu Asn Gly Lys Ala Lys Ile Glu Gly Ile Tyr Gly Ser Lys Leu Arg
305                 310                 315                 320

Val Ser Val Tyr Asp Ile Thr Asn Asn Ala His Arg Leu Val Gln Val
                325                 330                 335

Phe
```

<210> SEQ ID NO 21
<211> LENGTH: 981
<212> TYPE: DNA
<213> ORGANISM: Bacillus thuringiensis
<220> FEATURE:
<221> NAME/KEY: misc_feature
<222> LOCATION: (1)..(978)
<223> OTHER INFORMATION: Open Reading Frame TIC3626; Bt CFB 212742
<220> FEATURE:
<221> NAME/KEY: misc_feature
<222> LOCATION: (1)..(78)
<223> OTHER INFORMATION: signal peptide coding sequence
<220> FEATURE:
<221> NAME/KEY: misc_feature
<222> LOCATION: (79)..(978)
<223> OTHER INFORMATION: mature peptide coding sequence

<400> SEQUENCE: 21
atgagaaaaa aattaattgt aacaacagca tcattatctc tagctttaac aagttttggg 60
tccatcacat ctttggctga aagtaacaat caacaaaata aaatgattga aataaatgga 120
aatacttccg attcatctat tttaagccca attacatcta atatcattac agatgttgat 180
caacaaatga ataaaatttc agattattat tataataata atctgaaatt aaaagacata 240
ggggactatt atcacattat tcgactagaa aataaaaata ctactatgtc ttttgatctg 300
aatgctgatc atataaaaaa tttgcactat aatgatttac agccacaata tataggtgag 360
aatgaattta aaaatactac agatcaagaa caaacattta cgacagcatc gtattcacaa 420
gcagttacaa attctgtgag ttctactgtt attcaaggat ttaaggcaac aagcactact 480
agtctattga aaattcctat cctcttacca ggaggaataa acttaaatgc agaattcaac 540
tctgcttcaa acacaacaac tacaaataca acaactgaaa cccttacagc tccaccgcaa 600
aatattaaag tgccagcagg tagaacttat aaagtagaag taaatctatt aaagaaaaaa 660
ttcacaggtg atatagattt tcatggaaaa ggaacggatg taaaatcaaa tttaaaagta 720
cgtgcaacat attatggtcc tggattccca cgtcctacta aatatcctac ctatacatat 780
tctacagcgg atatgtggag aggtctaaca actgagcaaa aaaaacaaat tactggtgtt 840
aattttaata acaacaaaga tttaacgata gatggtacta caaaagtgga aggaatttat 900
ggaagcgatt tacaagtagt tgtttatgat ataacatata aaaatacacc taaaatagta 960
gaaactagaa cctttaaata a 981

<210> SEQ ID NO 22
<211> LENGTH: 326
<212> TYPE: PRT
<213> ORGANISM: Bacillus thuringiensis
<220> FEATURE:
<221> NAME/KEY: MISC_FEATURE
<222> LOCATION: (1)..(326)
<223> OTHER INFORMATION: precursor TIC3626; Bt CFB 212742
<220> FEATURE:
<221> NAME/KEY: MISC_FEATURE
<222> LOCATION: (1)..(26)
<223> OTHER INFORMATION: signal peptide amino acid sequence
<220> FEATURE:
<221> NAME/KEY: MISC_FEATURE
<222> LOCATION: (27)..(326)
<223> OTHER INFORMATION: mature peptide amino acid sequence

<400> SEQUENCE: 22

Met Arg Lys Lys Leu Ile Val Thr Thr Ala Ser Leu Ser Leu Ala Leu
1 5 10 15

Thr Ser Phe Gly Ser Ile Thr Ser Leu Ala Glu Ser Asn Asn Gln Gln
20 25 30

```
Asn Lys Met Ile Glu Ile Asn Gly Asn Thr Ser Asp Ser Ser Ile Leu
        35                  40                  45

Ser Pro Ile Thr Ser Asn Ile Ile Thr Asp Val Asp Gln Gln Met Asn
    50                  55                  60

Lys Ile Ser Asp Tyr Tyr Tyr Asn Asn Asn Leu Lys Leu Lys Asp Ile
65                  70                  75                  80

Gly Asp Tyr Tyr His Ile Ile Arg Leu Glu Asn Lys Asn Thr Thr Met
                85                  90                  95

Ser Phe Asp Leu Asn Ala Asp His Ile Lys Asn Leu His Tyr Asn Asp
            100                 105                 110

Leu Gln Pro Gln Tyr Ile Gly Glu Asn Glu Phe Lys Asn Thr Thr Asp
        115                 120                 125

Gln Glu Gln Thr Phe Thr Thr Ala Ser Tyr Ser Gln Ala Val Thr Asn
    130                 135                 140

Ser Val Ser Ser Thr Val Ile Gln Gly Phe Lys Ala Thr Ser Thr Thr
145                 150                 155                 160

Ser Leu Leu Lys Ile Pro Ile Leu Leu Pro Gly Gly Ile Asn Leu Asn
                165                 170                 175

Ala Glu Phe Asn Ser Ala Ser Asn Thr Thr Thr Thr Asn Thr Thr Thr
            180                 185                 190

Glu Thr Leu Thr Ala Pro Pro Gln Asn Ile Lys Val Pro Ala Gly Arg
        195                 200                 205

Thr Tyr Lys Val Glu Val Asn Leu Leu Lys Lys Lys Phe Thr Gly Asp
    210                 215                 220

Ile Asp Phe His Gly Lys Gly Thr Asp Val Lys Ser Asn Leu Lys Val
225                 230                 235                 240

Arg Ala Thr Tyr Tyr Gly Pro Gly Phe Pro Arg Pro Thr Lys Tyr Pro
                245                 250                 255

Thr Tyr Thr Tyr Ser Thr Ala Asp Met Trp Arg Gly Leu Thr Thr Glu
            260                 265                 270

Gln Lys Lys Gln Ile Thr Gly Val Asn Phe Asn Asn Asn Lys Asp Leu
        275                 280                 285

Thr Ile Asp Gly Thr Thr Lys Val Glu Gly Ile Tyr Gly Ser Asp Leu
    290                 295                 300

Gln Val Val Val Tyr Asp Ile Thr Tyr Lys Asn Thr Pro Lys Ile Val
305                 310                 315                 320

Glu Thr Arg Thr Phe Lys
                325
```

<210> SEQ ID NO 23
<211> LENGTH: 981
<212> TYPE: DNA
<213> ORGANISM: Bacillus thuringiensis
<220> FEATURE:
<221> NAME/KEY: misc_feature
<222> LOCATION: (1)..(978)
<223> OTHER INFORMATION: Open Reading Frame TIC2081; Bt EG6734
<220> FEATURE:
<221> NAME/KEY: misc_feature
<222> LOCATION: (1)..(78)
<223> OTHER INFORMATION: signal peptide coding sequence
<220> FEATURE:
<221> NAME/KEY: misc_feature
<222> LOCATION: (79)..(978)
<223> OTHER INFORMATION: mature peptide coding sequence

<400> SEQUENCE: 23

```
atgagaaaaa aattaattgt aacaacagca tcattatctc tagctttaac aagttttggg     60
```

```
tccatcacat ctttggctga aagtaacaat caacaaaata aaatggttga agtaaatgga    120

actacttcca attcatttat tttaagccca attacatcta atatcattac agatgttgat    180

caacaaatga ataaaatttc agattattat tataataata atctgaaatt aaaagacata    240

ggggactatt atcatattat acgactagaa aataaaaata ctactatgtc ttttgatctg    300

aatgctgatg atataaaaaa tttgcactat aatgatttac agccacaata tataggtgag    360

aatgaattta aaaatactac agatcaagaa caaacattta cgacagcatc gtattcacaa    420

gcagttacaa attctgtgag ttctactgtt attcaaggat ttaaggcaac aagcactact    480

agtctattga aaattcctat cctcttacca ggaggaataa acttaaatgc agaattcaac    540

tctgcttcaa atacaacaac tacaaataca acaactgaaa cccttacagc tccaccgcaa    600

aatattaaag tgccagcagg tagaacttat aaagtagaag taaatctatt aaagaaaaaa    660

ttcacaggtg atatagattt tcatggaaaa ggaacaaatg taaaatcaaa tttaaaagta    720

cgtgcaacat attatggtcc tggattcccg cgtcctacta aatatcctac ctatacatat    780

tctacagcgg atatgtggag aggtctaaca actgagcaaa aaaaacaaat tactggtgtt    840

aattttaata acaacaaaga tttaacgata gatggtacta caaaagtgga agggatttat    900

ggaagcaatt tagaagtagt tgtttatgat ataacaaata aaaatactcc taaaatagta    960

gaaactagaa cctttaaata a                                                981
```

<210> SEQ ID NO 24
<211> LENGTH: 326
<212> TYPE: PRT
<213> ORGANISM: Bacillus thuringiensis
<220> FEATURE:
<221> NAME/KEY: MISC_FEATURE
<222> LOCATION: (1)..(326)
<223> OTHER INFORMATION: precursor TIC2081; Bt EG6734
<220> FEATURE:
<221> NAME/KEY: MISC_FEATURE
<222> LOCATION: (1)..(26)
<223> OTHER INFORMATION: signal peptide amino acid sequence
<220> FEATURE:
<221> NAME/KEY: MISC_FEATURE
<222> LOCATION: (27)..(326)
<223> OTHER INFORMATION: mature peptide amino acid sequence

<400> SEQUENCE: 24

```
Met Arg Lys Lys Leu Ile Val Thr Thr Ala Ser Leu Ser Leu Ala Leu
1               5                   10                  15

Thr Ser Phe Gly Ser Ile Thr Ser Leu Ala Glu Ser Asn Asn Gln Gln
            20                  25                  30

Asn Lys Met Val Glu Val Asn Gly Thr Thr Ser Asn Ser Phe Ile Leu
        35                  40                  45

Ser Pro Ile Thr Ser Asn Ile Ile Thr Asp Val Asp Gln Gln Met Asn
    50                  55                  60

Lys Ile Ser Asp Tyr Tyr Tyr Asn Asn Asn Leu Lys Leu Lys Asp Ile
65                  70                  75                  80

Gly Asp Tyr Tyr His Ile Ile Arg Leu Glu Asn Lys Asn Thr Thr Met
                85                  90                  95

Ser Phe Asp Leu Asn Ala Asp Asp Ile Lys Asn Leu His Tyr Asn Asp
            100                 105                 110

Leu Gln Pro Gln Tyr Ile Gly Glu Asn Glu Phe Lys Asn Thr Thr Asp
        115                 120                 125

Gln Glu Gln Thr Phe Thr Thr Ala Ser Tyr Ser Gln Ala Val Thr Asn
    130                 135                 140
```

-continued

```
Ser Val Ser Ser Thr Val Ile Gln Gly Phe Lys Ala Thr Ser Thr Thr
145                 150                 155                 160

Ser Leu Leu Lys Ile Pro Ile Leu Leu Pro Gly Gly Ile Asn Leu Asn
                165                 170                 175

Ala Glu Phe Asn Ser Ala Ser Asn Thr Thr Thr Thr Asn Thr Thr Thr
            180                 185                 190

Glu Thr Leu Thr Ala Pro Pro Gln Asn Ile Lys Val Pro Ala Gly Arg
        195                 200                 205

Thr Tyr Lys Val Glu Val Asn Leu Leu Lys Lys Lys Phe Thr Gly Asp
    210                 215                 220

Ile Asp Phe His Gly Lys Gly Thr Asn Val Lys Ser Asn Leu Lys Val
225                 230                 235                 240

Arg Ala Thr Tyr Tyr Gly Pro Gly Phe Pro Arg Pro Thr Lys Tyr Pro
                245                 250                 255

Thr Tyr Thr Tyr Ser Thr Ala Asp Met Trp Arg Gly Leu Thr Thr Glu
            260                 265                 270

Gln Lys Lys Gln Ile Thr Gly Val Asn Phe Asn Asn Asn Lys Asp Leu
        275                 280                 285

Thr Ile Asp Gly Thr Thr Lys Val Glu Gly Ile Tyr Gly Ser Asn Leu
    290                 295                 300

Glu Val Val Val Tyr Asp Ile Thr Asn Lys Asn Thr Pro Lys Ile Val
305                 310                 315                 320

Glu Thr Arg Thr Phe Lys
                325


<210> SEQ ID NO 25
<211> LENGTH: 948
<212> TYPE: DNA
<213> ORGANISM: Artificial Sequence
<220> FEATURE:
<223> OTHER INFORMATION: TIC1825_G233A
<220> FEATURE:
<221> NAME/KEY: misc_feature
<222> LOCATION: (1)..(945)
<223> OTHER INFORMATION: Open Reading Frame TIC1825_G233A
<220> FEATURE:
<221> NAME/KEY: misc_feature
<222> LOCATION: (1)..(99)
<223> OTHER INFORMATION: signal peptide coding sequence
<220> FEATURE:
<221> NAME/KEY: misc_feature
<222> LOCATION: (100)..(945)
<223> OTHER INFORMATION: mature peptide coding sequence

<400> SEQUENCE: 25

atgacgaacc tatttaaatc tcaaaagact tttatagcca aactaggaat tgtattagga      60

atatcaagta ccctgttctt tggaagtaat gtcatggcag ctcaaaccac aaatattaca     120

gatgtagatg cacaaatgga caaaatttct gatttctatt ttaagaacga attagaatgg     180

aaagacttac ctgaataccc tggagcttat cattatatta gattagatag taagaaaaca     240

aatatggatt tagatctcaa agcgagcaat ttaaagaatt taacttatag tgatttacat     300

ccagaatata ttggtgaaaa tgaatttgat aatacaaatg gcagtataga tcaaacattc     360

acaacagcat cgtattctca tcaagttacg aactccgcta gtacaagtgt tacggaaggg     420

tttaaagtag gaggaaagac aacgcttttc aaattaccta ttttattaac agatggtgtt     480

gatattactg cagaattcaa ctctgcaaca agtacaacaa atacagttac agatactaag     540

actttaacag cttcaccaca aaatataaaa gttccagctg gtaagaaata tttagttaaa     600

gtggatatgg ctaagaaaac atttaatgga gatatagaat ttagtgcaaa tggaaagaat     660
```

```
gtaaaatcga aacttgacac cttagcaact tattatgcac ccggattccc acgtccaaat    720

aaatatccat cacttctatt tacaacagca gatatgtgga agaagttatc tactagtcag    780

caaaatcaaa taaagggagt tacttttgat tctagtaaga atcttatatt gaatgggaaa    840

gcacatgtaa atggaatctt tggaagtaaa ctacgtgtta gtgtttatga tattacggat    900

tcaaaattat cacctaaact aattcaacag aaatttatgg agcaatag                 948


<210> SEQ ID NO 26
<211> LENGTH: 315
<212> TYPE: PRT
<213> ORGANISM: Artificial Sequence
<220> FEATURE:
<223> OTHER INFORMATION: TIC1825_G233A
<220> FEATURE:
<221> NAME/KEY: MISC_FEATURE
<222> LOCATION: (1)..(315)
<223> OTHER INFORMATION: precursor TIC1825_G233A
<220> FEATURE:
<221> NAME/KEY: MISC_FEATURE
<222> LOCATION: (1)..(33)
<223> OTHER INFORMATION: signal peptide amino acid sequence
<220> FEATURE:
<221> NAME/KEY: MISC_FEATURE
<222> LOCATION: (34)..(315)
<223> OTHER INFORMATION: mature peptide amino acid sequence

<400> SEQUENCE: 26

Met Thr Asn Leu Phe Lys Ser Gln Lys Thr Phe Ile Ala Lys Leu Gly
1               5                   10                  15

Ile Val Leu Gly Ile Ser Ser Thr Leu Phe Phe Gly Ser Asn Val Met
            20                  25                  30

Ala Ala Gln Thr Thr Asn Ile Thr Asp Val Asp Ala Gln Met Asp Lys
        35                  40                  45

Ile Ser Asp Phe Tyr Phe Lys Asn Glu Leu Glu Trp Lys Asp Leu Pro
    50                  55                  60

Glu Tyr Pro Gly Ala Tyr His Tyr Ile Arg Leu Asp Ser Lys Lys Thr
65                  70                  75                  80

Asn Met Asp Leu Asp Leu Lys Ala Ser Asn Leu Lys Asn Leu Thr Tyr
                85                  90                  95

Ser Asp Leu His Pro Glu Tyr Ile Gly Glu Asn Glu Phe Asp Asn Thr
            100                 105                 110

Asn Gly Ser Ile Asp Gln Thr Phe Thr Thr Ala Ser Tyr Ser His Gln
        115                 120                 125

Val Thr Asn Ser Ala Ser Thr Ser Val Thr Glu Gly Phe Lys Val Gly
    130                 135                 140

Gly Lys Thr Thr Leu Phe Lys Leu Pro Ile Leu Leu Thr Asp Gly Val
145                 150                 155                 160

Asp Ile Thr Ala Glu Phe Asn Ser Ala Thr Ser Thr Thr Asn Thr Val
                165                 170                 175

Thr Asp Thr Lys Thr Leu Thr Ala Ser Pro Gln Asn Ile Lys Val Pro
            180                 185                 190

Ala Gly Lys Lys Tyr Leu Val Lys Val Asp Met Ala Lys Lys Thr Phe
        195                 200                 205

Asn Gly Asp Ile Glu Phe Ser Ala Asn Gly Lys Asn Val Lys Ser Lys
    210                 215                 220

Leu Asp Thr Leu Ala Thr Tyr Tyr Ala Pro Gly Phe Pro Arg Pro Asn
225                 230                 235                 240

Lys Tyr Pro Ser Leu Leu Phe Thr Thr Ala Asp Met Trp Lys Lys Leu
```

```
            245                 250                 255

Ser Thr Ser Gln Gln Asn Gln Ile Lys Gly Val Thr Phe Asp Ser Ser
            260                 265                 270

Lys Asn Leu Ile Leu Asn Gly Lys Ala His Val Asn Gly Ile Phe Gly
        275                 280                 285

Ser Lys Leu Arg Val Ser Val Tyr Asp Ile Thr Asp Ser Lys Leu Ser
    290                 295                 300

Pro Lys Leu Ile Gln Gln Lys Phe Met Glu Gln
305                 310                 315
```

<210> SEQ ID NO 27
<211> LENGTH: 948
<212> TYPE: DNA
<213> ORGANISM: Artificial Sequence
<220> FEATURE:
<223> OTHER INFORMATION: TIC1825_P234A
<220> FEATURE:
<221> NAME/KEY: misc_feature
<222> LOCATION: (1)..(945)
<223> OTHER INFORMATION: Open Reading Frame TIC1825_G234A
<220> FEATURE:
<221> NAME/KEY: misc_feature
<222> LOCATION: (1)..(99)
<223> OTHER INFORMATION: signal peptide coding sequence
<220> FEATURE:
<221> NAME/KEY: misc_feature
<222> LOCATION: (100)..(945)
<223> OTHER INFORMATION: mature peptide coding sequence

<400> SEQUENCE: 27

```
atgacgaacc tatttaaatc tcaaaaaact tttatagcca aactaggaat tgtattagga     60

atatcaagta ccctgttttt tggaagtaat gtcatggcag ctcaaaccac aaatattaca    120

gatgtagatg cacaaatgga caaaatttct gatttttatt ttaaaaacga attagaatgg    180

aaagacttac ctgaataccc tggagcttat cattatatta gattagatag taaaaaaaca    240

aatatggatt tagatctcaa agcgagcaat ttaaaaaatt taacttatag tgatttacat    300

ccagaatata ttggtgaaaa tgaatttgat aatacaaatg gcagtataga tcaaacattc    360

acaacagcat cgtattctca tcaagttacg aactccgcta gtacaagtgt tacggaaggg    420

tttaaagtag gaggaaaaac aacgcttttt aaattaccta ttttattaac agatggtgtt    480

gatattactg cagaattcaa ctctgcaaca agtacaacaa atacagttac agatactaag    540

actttaacag cttcaccaca aaatataaaa gttccagctg gtaaaaaata tttagttaaa    600

gtggatatgg ctaaaaaaac atttaatgga gatatagaat ttagtgcaaa tggaaagaat    660

gtaaaatcga aacttgacac cttagcaact tattatggag caggattccc acgtccaaat    720

aaatatccat cacttctatt tacaacagca gatatgtgga aaaagttatc tactagtcag    780

caaaatcaaa taaagggagt tacttttgat tctagtaaaa atcttatatt gaatgggaaa    840

gcacatgtaa atggaatctt tggaagtaaa ctacgtgtta gtgtttatga tattacggat    900

tcaaaattat cacctaaact aattcaacag aaatttatgg agcaataa                 948
```

<210> SEQ ID NO 28
<211> LENGTH: 315
<212> TYPE: PRT
<213> ORGANISM: Artificial Sequence
<220> FEATURE:
<223> OTHER INFORMATION: TIC1825_P234A
<220> FEATURE:
<221> NAME/KEY: MISC_FEATURE
<222> LOCATION: (1)..(315)
<223> OTHER INFORMATION: precursor TIC1825_G234A
<220> FEATURE:
<221> NAME/KEY: MISC_FEATURE
<222> LOCATION: (1)..(33)
<223> OTHER INFORMATION: signal peptide amino acid sequence
<220> FEATURE:
<221> NAME/KEY: MISC_FEATURE
<222> LOCATION: (34)..(315)
<223> OTHER INFORMATION: mature peptide amino acid sequence

<400> SEQUENCE: 28

```
Met Thr Asn Leu Phe Lys Ser Gln Lys Thr Phe Ile Ala Lys Leu Gly
1               5                   10                  15

Ile Val Leu Gly Ile Ser Ser Thr Leu Phe Phe Gly Ser Asn Val Met
            20                  25                  30

Ala Ala Gln Thr Thr Asn Ile Thr Asp Val Asp Ala Gln Met Asp Lys
        35                  40                  45

Ile Ser Asp Phe Tyr Phe Lys Asn Glu Leu Glu Trp Lys Asp Leu Pro
    50                  55                  60

Glu Tyr Pro Gly Ala Tyr His Tyr Ile Arg Leu Asp Ser Lys Lys Thr
65                  70                  75                  80

Asn Met Asp Leu Asp Leu Lys Ala Ser Asn Leu Lys Asn Leu Thr Tyr
                85                  90                  95

Ser Asp Leu His Pro Glu Tyr Ile Gly Glu Asn Glu Phe Asp Asn Thr
            100                 105                 110

Asn Gly Ser Ile Asp Gln Thr Phe Thr Thr Ala Ser Tyr Ser His Gln
        115                 120                 125

Val Thr Asn Ser Ala Ser Thr Ser Val Thr Glu Gly Phe Lys Val Gly
    130                 135                 140

Gly Lys Thr Thr Leu Phe Lys Leu Pro Ile Leu Leu Thr Asp Gly Val
145                 150                 155                 160

Asp Ile Thr Ala Glu Phe Asn Ser Ala Thr Ser Thr Thr Asn Thr Val
                165                 170                 175

Thr Asp Thr Lys Thr Leu Thr Ala Ser Pro Gln Asn Ile Lys Val Pro
            180                 185                 190

Ala Gly Lys Lys Tyr Leu Val Lys Val Asp Met Ala Lys Lys Thr Phe
        195                 200                 205

Asn Gly Asp Ile Glu Phe Ser Ala Asn Gly Lys Asn Val Lys Ser Lys
    210                 215                 220

Leu Asp Thr Leu Ala Thr Tyr Tyr Gly Ala Gly Phe Pro Arg Pro Asn
225                 230                 235                 240

Lys Tyr Pro Ser Leu Leu Phe Thr Thr Ala Asp Met Trp Lys Lys Leu
                245                 250                 255

Ser Thr Ser Gln Gln Asn Gln Ile Lys Gly Val Thr Phe Asp Ser Ser
            260                 265                 270

Lys Asn Leu Ile Leu Asn Gly Lys Ala His Val Asn Gly Ile Phe Gly
        275                 280                 285

Ser Lys Leu Arg Val Ser Val Tyr Asp Ile Thr Asp Ser Lys Leu Ser
    290                 295                 300

Pro Lys Leu Ile Gln Gln Lys Phe Met Glu Gln
305                 310                 315
```

<210> SEQ ID NO 29
<211> LENGTH: 948
<212> TYPE: DNA
<213> ORGANISM: Artificial Sequence
<220> FEATURE:
<223> OTHER INFORMATION: TIC1825_K224T_D226N_G233A_P234A_L246T_T248V
<220> FEATURE:

<221> NAME/KEY: misc_feature
<222> LOCATION: (1)..(945)
<223> OTHER INFORMATION: Open Reading Frame
      TIC1825_K224T_D226N_G233A_P234A_L246T_T248V
<220> FEATURE:
<221> NAME/KEY: misc_feature
<222> LOCATION: (1)..(99)
<223> OTHER INFORMATION: signal peptide coding sequence
<220> FEATURE:
<221> NAME/KEY: misc_feature
<222> LOCATION: (100)..(945)
<223> OTHER INFORMATION: mature peptide coding sequence

<400> SEQUENCE: 29
atgacgaacc tatttaaatc tcaaaagact tttatagcca aactaggaat tgtattagga 60
atatcaagta ccctgttctt tggaagtaat gtcatggcag ctcaaaccac aaatattaca 120
gatgtagatg cacaaatgga caaaatttct gatttctatt ttaagaacga attagaatgg 180
aaagacttac ctgaataccc tggagcttat cattatatta gattagatag taagaaaaca 240
aatatggatt tagatctcaa agcgagcaat ttaaagaatt taacttatag tgatttacat 300
ccagaatata ttggtgaaaa tgaatttgat aatacaaatg gcagtataga tcaaacattc 360
acaacagcat cgtattctca tcaagttacg aactccgcta gtacaagtgt tacggaaggg 420
tttaaagtag gaggaaagac aacgcttttc aaattaccta ttttattaac agatggtgtt 480
gatattactg cagaattcaa ctctgcaaca agtacaacaa atacagttac agatactaag 540
actttaacag cttcaccaca aaatataaaa gttccagctg gtaagaaata tttagttaaa 600
gtggatatgg ctaagaaaac atttaatgga gatatagaat ttagtgcaaa tggaaagaat 660
gtaaaatcga cacttaatac cttagcaact tattatgcag caggattccc acgtccaaat 720
aaatatccat cacttacatt tgtaacagca gatatgtgga agaagttatc tactagtcag 780
caaaatcaaa taaagggagt tacttttgat tctagtaaga atcttatatt gaatgggaaa 840
gcacatgtaa atggaatctt tggaagtaaa ctacgtgtta gtgtttatga tattacggat 900
tcaaaattat cacctaaact aattcaacag aaatttatgg agcaatag 948

<210> SEQ ID NO 30
<211> LENGTH: 315
<212> TYPE: PRT
<213> ORGANISM: Artificial Sequence
<220> FEATURE:
<223> OTHER INFORMATION: TIC1825_K224T_D226N_G233A_P234A_L246T_T248V
<220> FEATURE:
<221> NAME/KEY: MISC_FEATURE
<222> LOCATION: (1)..(315)
<223> OTHER INFORMATION: precursor
      TIC1825_K224T_D226N_G233A_P234A_L246T_T248V
<220> FEATURE:
<221> NAME/KEY: MISC_FEATURE
<222> LOCATION: (1)..(33)
<223> OTHER INFORMATION: signal peptide amino acid sequence
<220> FEATURE:
<221> NAME/KEY: MISC_FEATURE
<222> LOCATION: (34)..(315)
<223> OTHER INFORMATION: mature peptide amino acid sequence

<400> SEQUENCE: 30

Met Thr Asn Leu Phe Lys Ser Gln Lys Thr Phe Ile Ala Lys Leu Gly
1               5                   10                  15

Ile Val Leu Gly Ile Ser Ser Thr Leu Phe Phe Gly Ser Asn Val Met
            20                  25                  30

Ala Ala Gln Thr Thr Asn Ile Thr Asp Val Asp Ala Gln Met Asp Lys
        35                  40                  45

```
Ile Ser Asp Phe Tyr Phe Lys Asn Glu Leu Glu Trp Lys Asp Leu Pro
    50                  55                  60

Glu Tyr Pro Gly Ala Tyr His Tyr Ile Arg Leu Asp Ser Lys Lys Thr
65                  70                  75                  80

Asn Met Asp Leu Asp Leu Lys Ala Ser Asn Leu Lys Asn Leu Thr Tyr
                85                  90                  95

Ser Asp Leu His Pro Glu Tyr Ile Gly Glu Asn Glu Phe Asp Asn Thr
            100                 105                 110

Asn Gly Ser Ile Asp Gln Thr Phe Thr Thr Ala Ser Tyr Ser His Gln
        115                 120                 125

Val Thr Asn Ser Ala Ser Thr Ser Val Thr Glu Gly Phe Lys Val Gly
    130                 135                 140

Gly Lys Thr Thr Leu Phe Lys Leu Pro Ile Leu Leu Thr Asp Gly Val
145                 150                 155                 160

Asp Ile Thr Ala Glu Phe Asn Ser Ala Thr Ser Thr Thr Asn Thr Val
                165                 170                 175

Thr Asp Thr Lys Thr Leu Thr Ala Ser Pro Gln Asn Ile Lys Val Pro
            180                 185                 190

Ala Gly Lys Lys Tyr Leu Val Lys Val Asp Met Ala Lys Lys Thr Phe
        195                 200                 205

Asn Gly Asp Ile Glu Phe Ser Ala Asn Gly Lys Asn Val Lys Ser Thr
    210                 215                 220

Leu Asn Thr Leu Ala Thr Tyr Tyr Ala Ala Gly Phe Pro Arg Pro Asn
225                 230                 235                 240

Lys Tyr Pro Ser Leu Thr Phe Val Thr Ala Asp Met Trp Lys Lys Leu
                245                 250                 255

Ser Thr Ser Gln Gln Asn Gln Ile Lys Gly Val Thr Phe Asp Ser Ser
            260                 265                 270

Lys Asn Leu Ile Leu Asn Gly Lys Ala His Val Asn Gly Ile Phe Gly
        275                 280                 285

Ser Lys Leu Arg Val Ser Val Tyr Asp Ile Thr Asp Ser Lys Leu Ser
    290                 295                 300

Pro Lys Leu Ile Gln Gln Lys Phe Met Glu Gln
305                 310                 315
```

<210> SEQ ID NO 31
<211> LENGTH: 849
<212> TYPE: DNA
<213> ORGANISM: Artificial Sequence
<220> FEATURE:
<223> OTHER INFORMATION: useful in plants.
<220> FEATURE:
<221> NAME/KEY: misc_feature
<222> LOCATION: (1)..(6)
<223> OTHER INFORMATION: TIC2463_3 variant of mature peptide coding sequence starting with MA (bonus alanine)
<220> FEATURE:
<221> NAME/KEY: misc_feature
<222> LOCATION: (7)..(846)
<223> OTHER INFORMATION: TIC2463 mature peptide coding sequence.

<400> SEQUENCE: 31

```
atggccgacc agaccgccaa catcaccgac gtggacgccc agatggacaa gatcagcgac      60

ttctacttca agaacgagct ggagtggaag gacttgcccg agtaccctgg cgcgtaccac     120

tacatccgcc tggacagcaa gaagacgaac atggacctcg acctcaaggc caacaacatc     180

aagaacctca cctactccga cctgaaccct gagtacgtgg gcgagaacga gttcgacaac     240

accaactcca acatcgacca gaccttcacc accgccgcct actcccacca agtgaccaac     300
```

```
tccgcctcca ccaacgtgac caagggcttc aaggtgggcg gcaagaccac cctcctcaag    360

ctgcctatcc tgctgaccag cggcgtggag atcaacgccg agttcaacag cgctaccagc    420

actaccaaca ctgtcactga caccaagact ctgacggcta gtcctcagaa catcaaggtg    480

cccgctggta ggaagttcct ggtcaaggtg gacatggcga agaagacgtt caacggtgaa    540

gtggacttct ctgcgacggg ctacaacgtc aagagcacgc tgaacacgct ggcgacgtac    600

tacgcggcgg gctttcctcg gccgaacaag tacccgtctc tgacattcgt caccgccgac    660

atgtggaaga agctctctac ctcgcagcag aatcagatca acggcgtgaa cttcgatagc    720

agcaaggact tggtgctgaa tggaaaggcc aatgtgcacg gaatcttcgg ctccaccctg    780

cgtgttagtg tgtacgacat cacagactcg aagctgtcgc cgaagctggt acagcacaag    840

aacatctga                                                            849


<210> SEQ ID NO 32
<211> LENGTH: 282
<212> TYPE: PRT
<213> ORGANISM: Artificial Sequence
<220> FEATURE:
<223> OTHER INFORMATION: Variant of mature peptide amino acid sequence
      segment of SEQ ID NO:4 (residues 34-313).
<220> FEATURE:
<221> NAME/KEY: MISC_FEATURE
<222> LOCATION: (1)..(2)
<223> OTHER INFORMATION: TIC2463_3 variant of mature peptide amino acid
      sequence starting with MA (bonus alanine).
<220> FEATURE:
<221> NAME/KEY: MISC_FEATURE
<222> LOCATION: (3)..(282)
<223> OTHER INFORMATION: TIC2463 mature peptide amino acid sequence.

<400> SEQUENCE: 32

Met Ala Asp Gln Thr Ala Asn Ile Thr Asp Val Asp Ala Gln Met Asp
1               5                   10                  15

Lys Ile Ser Asp Phe Tyr Phe Lys Asn Glu Leu Glu Trp Lys Asp Leu
            20                  25                  30

Pro Glu Tyr Pro Gly Ala Tyr His Tyr Ile Arg Leu Asp Ser Lys Lys
        35                  40                  45

Thr Asn Met Asp Leu Asp Leu Lys Ala Asn Asn Ile Lys Asn Leu Thr
    50                  55                  60

Tyr Ser Asp Leu Asn Pro Glu Tyr Val Gly Glu Asn Glu Phe Asp Asn
65                  70                  75                  80

Thr Asn Ser Asn Ile Asp Gln Thr Phe Thr Thr Ala Ala Tyr Ser His
                85                  90                  95

Gln Val Thr Asn Ser Ala Ser Thr Asn Val Thr Lys Gly Phe Lys Val
            100                 105                 110

Gly Gly Lys Thr Thr Leu Leu Lys Leu Pro Ile Leu Leu Thr Ser Gly
        115                 120                 125

Val Glu Ile Asn Ala Glu Phe Asn Ser Ala Thr Ser Thr Thr Asn Thr
    130                 135                 140

Val Thr Asp Thr Lys Thr Leu Thr Ala Ser Pro Gln Asn Ile Lys Val
145                 150                 155                 160

Pro Ala Gly Arg Lys Phe Leu Val Lys Val Asp Met Ala Lys Lys Thr
                165                 170                 175

Phe Asn Gly Glu Val Asp Phe Ser Ala Thr Gly Tyr Asn Val Lys Ser
            180                 185                 190

Thr Leu Asn Thr Leu Ala Thr Tyr Tyr Ala Ala Gly Phe Pro Arg Pro
        195                 200                 205
```

-continued

```
Asn Lys Tyr Pro Ser Leu Thr Phe Val Thr Ala Asp Met Trp Lys Lys
    210                 215                 220

Leu Ser Thr Ser Gln Gln Asn Gln Ile Asn Gly Val Asn Phe Asp Ser
225                 230                 235                 240

Ser Lys Asp Leu Val Leu Asn Gly Lys Ala Asn Val His Gly Ile Phe
                245                 250                 255

Gly Ser Thr Leu Arg Val Ser Val Tyr Asp Ile Thr Asp Ser Lys Leu
            260                 265                 270

Ser Pro Lys Leu Val Gln His Lys Asn Ile
        275                 280
```

```
<210> SEQ ID NO 33
<211> LENGTH: 846
<212> TYPE: DNA
<213> ORGANISM: Artificial Sequence
<220> FEATURE:
<223> OTHER INFORMATION: useful in plants.
<220> FEATURE:
<221> NAME/KEY: misc_feature
<222> LOCATION: (1)..(3)
<223> OTHER INFORMATION: TIC2463_4 variant of mature peptide coding
      sequence starting with M.
<220> FEATURE:
<221> NAME/KEY: misc_feature
<222> LOCATION: (4)..(843)
<223> OTHER INFORMATION: TIC2463 mature peptide coding sequence.

<400> SEQUENCE: 33

atggaccaga ccgccaacat caccgacgtg gacgcccaga tggacaagat cagcgacttc      60

tacttcaaga acgagctgga gtggaaggac ttgcccgagt accctggcgc gtaccactac     120

atccgcctgg acagcaagaa gacgaacatg gacctcgacc tcaaggccaa caacatcaag     180

aacctcacct actccgacct gaaccctgag tacgtgggcg agaacgagtt cgacaacacc     240

aactccaaca tcgaccagac cttcaccacc gccgcctact cccaccaagt gaccaactcc     300

gcctccacca acgtgaccaa gggcttcaag gtgggcggca agaccaccct cctcaagctg     360

cctatcctgc tgaccagcgg cgtggagatc aacgccgagt tcaacagcgc taccagcact     420

accaacactg tcactgacac caagactctg acggctagtc ctcagaacat caaggtgccc     480

gctggtagga agttcctggt caaggtggac atggcgaaga agacgttcaa cggtgaagtg     540

gacttctctg cgacgggcta caacgtcaag agcacgctga acacgctggc gacgtactac     600

gcggcgggct ttcctcggcc gaacaagtac ccgtctctga cattcgtcac cgccgacatg     660

tggaagaagc tctctacctc gcagcagaat cagatcaacg gcgtgaactt cgatagcagc     720

aaggacttgg tgctgaatgg aaaggccaat gtgcacggaa tcttcggctc caccctgcgt     780

gttagtgtgt acgacatcac agactcgaag ctgtcgccga agctggtaca gcacaagaac     840

atctga                                                                846
```

```
<210> SEQ ID NO 34
<211> LENGTH: 281
<212> TYPE: PRT
<213> ORGANISM: Artificial Sequence
<220> FEATURE:
<223> OTHER INFORMATION: Variant of mature peptide amino acid sequence
      segment of SEQ ID NO:4 (residues 34 to 313).
<220> FEATURE:
<221> NAME/KEY: MISC_FEATURE
<222> LOCATION: (1)..(1)
<223> OTHER INFORMATION: TIC2463_4 variant of mature peptide amino acid
      sequence starting with M.
<220> FEATURE:
```

```
<221> NAME/KEY: MISC_FEATURE
<222> LOCATION: (2)..(281)
<223> OTHER INFORMATION: TIC2463 mature peptide amino acid sequence.

<400> SEQUENCE: 34

Met Asp Gln Thr Ala Asn Ile Thr Asp Val Asp Ala Gln Met Asp Lys
1               5                   10                  15

Ile Ser Asp Phe Tyr Phe Lys Asn Glu Leu Glu Trp Lys Asp Leu Pro
            20                  25                  30

Glu Tyr Pro Gly Ala Tyr His Tyr Ile Arg Leu Asp Ser Lys Lys Thr
        35                  40                  45

Asn Met Asp Leu Asp Leu Lys Ala Asn Asn Ile Lys Asn Leu Thr Tyr
    50                  55                  60

Ser Asp Leu Asn Pro Glu Tyr Val Gly Glu Asn Glu Phe Asp Asn Thr
65                  70                  75                  80

Asn Ser Asn Ile Asp Gln Thr Phe Thr Thr Ala Ala Tyr Ser His Gln
                85                  90                  95

Val Thr Asn Ser Ala Ser Thr Asn Val Thr Lys Gly Phe Lys Val Gly
            100                 105                 110

Gly Lys Thr Thr Leu Leu Lys Leu Pro Ile Leu Leu Thr Ser Gly Val
        115                 120                 125

Glu Ile Asn Ala Glu Phe Asn Ser Ala Thr Ser Thr Thr Asn Thr Val
    130                 135                 140

Thr Asp Thr Lys Thr Leu Thr Ala Ser Pro Gln Asn Ile Lys Val Pro
145                 150                 155                 160

Ala Gly Arg Lys Phe Leu Val Lys Val Asp Met Ala Lys Lys Thr Phe
                165                 170                 175

Asn Gly Glu Val Asp Phe Ser Ala Thr Gly Tyr Asn Val Lys Ser Thr
            180                 185                 190

Leu Asn Thr Leu Ala Thr Tyr Tyr Ala Ala Gly Phe Pro Arg Pro Asn
        195                 200                 205

Lys Tyr Pro Ser Leu Thr Phe Val Thr Ala Asp Met Trp Lys Lys Leu
    210                 215                 220

Ser Thr Ser Gln Gln Asn Gln Ile Asn Gly Val Asn Phe Asp Ser Ser
225                 230                 235                 240

Lys Asp Leu Val Leu Asn Gly Lys Ala Asn Val His Gly Ile Phe Gly
                245                 250                 255

Ser Thr Leu Arg Val Ser Val Tyr Asp Ile Thr Asp Ser Lys Leu Ser
            260                 265                 270

Pro Lys Leu Val Gln His Lys Asn Ile
        275                 280


<210> SEQ ID NO 35
<211> LENGTH: 1068
<212> TYPE: DNA
<213> ORGANISM: Artificial Sequence
<220> FEATURE:
<223> OTHER INFORMATION: useful in plants.
<220> FEATURE:
<221> NAME/KEY: misc_feature
<222> LOCATION: (1)..(1065)
<223> OTHER INFORMATION: TIC2463_Ts-Wx (amyloplast)
<220> FEATURE:
<221> NAME/KEY: misc_feature
<222> LOCATION: (1)..(225)
<223> OTHER INFORMATION: amyloplast target peptide coding sequence
<220> FEATURE:
<221> NAME/KEY: misc_feature
<222> LOCATION: (226)..(1065)
<223> OTHER INFORMATION: TIC2463 mature peptide coding sequence
```

<400> SEQUENCE: 35

```
atggcggctc tggccacttc ccagctcgcc accacccgcg ccggcttcgg cctcggcgac     60
gcctcctcct ccatgttccg ccccggcgtc cagggcctca ggggctcccg ggcctcctcc    120
ccggcggcca cgctcagcgt gcggaccagc gcgcgcgccg cgcccaggca gcagcaccgc    180
cgggcgcagc gcggcgccag gttcccctcc ctcgtcgtct gcgccgacca gaccgccaac    240
atcaccgacg tggacgccca gatggacaag atcagcgact tctacttcaa gaacgagctg    300
gagtggaagg acttgcccga gtaccctggc gcgtaccact acatccgcct ggacagcaag    360
aagacgaaca tggacctcga cctcaaggcc aacaacatca agaacctcac ctactccgac    420
ctgaaccctg agtacgtggg cgagaacgag ttcgacaaca ccaactccaa catcgaccag    480
accttcacca ccgccgccta ctcccaccaa gtgaccaact ccgcctccac caacgtgacc    540
aagggcttca aggtgggcgg caagaccacc ctcctcaagc tgcctatcct gctgaccagc    600
ggcgtggaga tcaacgccga gttcaacagc gctaccagca ctaccaacac tgtcactgac    660
accaagactc tgacggctag tcctcagaac atcaaggtgc ccgctggtag gaagttcctg    720
gtcaaggtgg acatggcgaa gaagacgttc aacggtgaag tggacttctc tgcgacgggc    780
tacaacgtca agagcacgct gaacacgctg gcgacgtact acgcggcggg ctttcctcgg    840
ccgaacaagt acccgtctct gacattcgtc accgccgaca tgtggaagaa gctctctacc    900
tcgcagcaga atcagatcaa cggcgtgaac ttcgatagca gcaaggactt ggtgctgaat    960
ggaaaggcca atgtgcacgg aatcttcggc tccaccctgc gtgttagtgt gtacgacatc   1020
acagactcga agctgtcgcc gaagctggta cagcacaaga acatctga               1068
```

<210> SEQ ID NO 36
<211> LENGTH: 355
<212> TYPE: PRT
<213> ORGANISM: Artificial Sequence
<220> FEATURE:
<223> OTHER INFORMATION: TIC2463_Ts-Wx (amyloplast)
<220> FEATURE:
<221> NAME/KEY: MISC_FEATURE
<222> LOCATION: (1)..(75)
<223> OTHER INFORMATION: amyloplast target peptide amino acid sequence
<220> FEATURE:
<221> NAME/KEY: MISC_FEATURE
<222> LOCATION: (76)..(355)
<223> OTHER INFORMATION: TIC2463 mature peptide amino acid sequence

<400> SEQUENCE: 36

```
Met Ala Ala Leu Ala Thr Ser Gln Leu Ala Thr Thr Arg Ala Gly Phe
1               5                   10                  15

Gly Leu Gly Asp Ala Ser Ser Ser Met Phe Arg Pro Gly Val Gln Gly
            20                  25                  30

Leu Arg Gly Ser Arg Ala Ser Ser Pro Ala Ala Thr Leu Ser Val Arg
        35                  40                  45

Thr Ser Ala Arg Ala Ala Pro Arg Gln Gln His Arg Arg Ala Gln Arg
    50                  55                  60

Gly Ala Arg Phe Pro Ser Leu Val Val Cys Ala Asp Gln Thr Ala Asn
65                  70                  75                  80

Ile Thr Asp Val Asp Ala Gln Met Asp Lys Ile Ser Asp Phe Tyr Phe
                85                  90                  95

Lys Asn Glu Leu Glu Trp Lys Asp Leu Pro Glu Tyr Pro Gly Ala Tyr
            100                 105                 110

His Tyr Ile Arg Leu Asp Ser Lys Lys Thr Asn Met Asp Leu Asp Leu
```

```
        115                 120                 125

Lys Ala Asn Asn Ile Lys Asn Leu Thr Tyr Ser Asp Leu Asn Pro Glu
    130                 135                 140

Tyr Val Gly Glu Asn Glu Phe Asp Asn Thr Asn Ser Asn Ile Asp Gln
145                 150                 155                 160

Thr Phe Thr Thr Ala Ala Tyr Ser His Gln Val Thr Asn Ser Ala Ser
                165                 170                 175

Thr Asn Val Thr Lys Gly Phe Lys Val Gly Gly Lys Thr Thr Leu Leu
            180                 185                 190

Lys Leu Pro Ile Leu Leu Thr Ser Gly Val Glu Ile Asn Ala Glu Phe
        195                 200                 205

Asn Ser Ala Thr Ser Thr Thr Asn Thr Val Thr Asp Thr Lys Thr Leu
    210                 215                 220

Thr Ala Ser Pro Gln Asn Ile Lys Val Pro Ala Gly Arg Lys Phe Leu
225                 230                 235                 240

Val Lys Val Asp Met Ala Lys Lys Thr Phe Asn Gly Glu Val Asp Phe
                245                 250                 255

Ser Ala Thr Gly Tyr Asn Val Lys Ser Thr Leu Asn Thr Leu Ala Thr
            260                 265                 270

Tyr Tyr Ala Ala Gly Phe Pro Arg Pro Asn Lys Tyr Pro Ser Leu Thr
        275                 280                 285

Phe Val Thr Ala Asp Met Trp Lys Lys Leu Ser Thr Ser Gln Gln Asn
    290                 295                 300

Gln Ile Asn Gly Val Asn Phe Asp Ser Ser Lys Asp Leu Val Leu Asn
305                 310                 315                 320

Gly Lys Ala Asn Val His Gly Ile Phe Gly Ser Thr Leu Arg Val Ser
                325                 330                 335

Val Tyr Asp Ile Thr Asp Ser Lys Leu Ser Pro Lys Leu Val Gln His
            340                 345                 350

Lys Asn Ile
        355


<210> SEQ ID NO 37
<211> LENGTH: 1026
<212> TYPE: DNA
<213> ORGANISM: Artificial Sequence
<220> FEATURE:
<223> OTHER INFORMATION: useful in plants.
<220> FEATURE:
<221> NAME/KEY: misc_feature
<222> LOCATION: (1)..(1023)
<223> OTHER INFORMATION: TIC2463_Ts-CR88 (chloroplast)
<220> FEATURE:
<221> NAME/KEY: misc_feature
<222> LOCATION: (1)..(183)
<223> OTHER INFORMATION: chloroplast target peptide coding sequence
<220> FEATURE:
<221> NAME/KEY: misc_feature
<222> LOCATION: (184)..(1023)
<223> OTHER INFORMATION: TIC2463 mature peptide coding sequence

<400> SEQUENCE: 37

atggccccgg cgctgagccg gagcctgtac accagcccgc tgaccagcgt gccgatcacc      60

ccggtcagct ccaggctcag ccacctgcgc tccagcttcc tgccgcacgg aggggccctg     120

aggaccggcg tgagctgctc ctggaacctc gagaagcggt gcaaccggtt cgcggtcaag     180

tgcgaccaga ccgccaacat caccgacgtg gacgcccaga tggacaagat cagcgacttc     240

tacttcaaga acgagctgga gtggaaggac ttgcccgagt accctggcgc gtaccactac     300
```

```
atccgcctgg acagcaagaa gacgaacatg gacctcgacc tcaaggccaa caacatcaag    360

aacctcacct actccgacct gaaccctgag tacgtgggcg agaacgagtt cgacaacacc    420

aactccaaca tcgaccagac cttcaccacc gccgcctact cccaccaagt gaccaactcc    480

gcctccacca acgtgaccaa gggcttcaag gtgggcggca agaccaccct cctcaagctg    540

cctatcctgc tgaccagcgg cgtggagatc aacgccgagt tcaacagcgc taccagcact    600

accaacactg tcactgacac caagactctg acggctagtc ctcagaacat caaggtgccc    660

gctggtagga agttcctggt caaggtggac atggcgaaga agacgttcaa cggtgaagtg    720

gacttctctg cgacgggcta caacgtcaag agcacgctga acacgctggc gacgtactac    780

gcggcgggct ttcctcggcc gaacaagtac ccgtctctga cattcgtcac cgccgacatg    840

tggaagaagc tctctacctc gcagcagaat cagatcaacg gcgtgaactt cgatagcagc    900

aaggacttgg tgctgaatgg aaaggccaat gtgcacggaa tcttcggctc caccctgcgt    960

gttagtgtgt acgacatcac agactcgaag ctgtcgccga agctggtaca gcacaagaac   1020

atctga                                                              1026
```

```
<210> SEQ ID NO 38
<211> LENGTH: 341
<212> TYPE: PRT
<213> ORGANISM: Artificial Sequence
<220> FEATURE:
<223> OTHER INFORMATION: TIC2463_Ts-CR88 (chloroplast)
<220> FEATURE:
<221> NAME/KEY: MISC_FEATURE
<222> LOCATION: (1)..(61)
<223> OTHER INFORMATION: chloroplast target peptide amino acid sequence
<220> FEATURE:
<221> NAME/KEY: MISC_FEATURE
<222> LOCATION: (62)..(341)
<223> OTHER INFORMATION: TIC2463 mature peptide amino acid sequence

<400> SEQUENCE: 38

Met Ala Pro Ala Leu Ser Arg Ser Leu Tyr Thr Ser Pro Leu Thr Ser
1               5                   10                  15

Val Pro Ile Thr Pro Val Ser Ser Arg Leu Ser His Leu Arg Ser Ser
            20                  25                  30

Phe Leu Pro His Gly Gly Ala Leu Arg Thr Gly Val Ser Cys Ser Trp
        35                  40                  45

Asn Leu Glu Lys Arg Cys Asn Arg Phe Ala Val Lys Cys Asp Gln Thr
    50                  55                  60

Ala Asn Ile Thr Asp Val Asp Ala Gln Met Asp Lys Ile Ser Asp Phe
65                  70                  75                  80

Tyr Phe Lys Asn Glu Leu Glu Trp Lys Asp Leu Pro Glu Tyr Pro Gly
                85                  90                  95

Ala Tyr His Tyr Ile Arg Leu Asp Ser Lys Lys Thr Asn Met Asp Leu
            100                 105                 110

Asp Leu Lys Ala Asn Asn Ile Lys Asn Leu Thr Tyr Ser Asp Leu Asn
        115                 120                 125

Pro Glu Tyr Val Gly Glu Asn Glu Phe Asp Asn Thr Asn Ser Asn Ile
    130                 135                 140

Asp Gln Thr Phe Thr Thr Ala Ala Tyr Ser His Gln Val Thr Asn Ser
145                 150                 155                 160

Ala Ser Thr Asn Val Thr Lys Gly Phe Lys Val Gly Gly Lys Thr Thr
                165                 170                 175

Leu Leu Lys Leu Pro Ile Leu Leu Thr Ser Gly Val Glu Ile Asn Ala
            180                 185                 190
```

```
Glu Phe Asn Ser Ala Thr Ser Thr Thr Asn Thr Val Thr Asp Thr Lys
        195                 200                 205

Thr Leu Thr Ala Ser Pro Gln Asn Ile Lys Val Pro Ala Gly Arg Lys
    210                 215                 220

Phe Leu Val Lys Val Asp Met Ala Lys Lys Thr Phe Asn Gly Glu Val
225                 230                 235                 240

Asp Phe Ser Ala Thr Gly Tyr Asn Val Lys Ser Thr Leu Asn Thr Leu
                245                 250                 255

Ala Thr Tyr Tyr Ala Ala Gly Phe Pro Arg Pro Asn Lys Tyr Pro Ser
            260                 265                 270

Leu Thr Phe Val Thr Ala Asp Met Trp Lys Lys Leu Ser Thr Ser Gln
        275                 280                 285

Gln Asn Gln Ile Asn Gly Val Asn Phe Asp Ser Ser Lys Asp Leu Val
    290                 295                 300

Leu Asn Gly Lys Ala Asn Val His Gly Ile Phe Gly Ser Thr Leu Arg
305                 310                 315                 320

Val Ser Val Tyr Asp Ile Thr Asp Ser Lys Leu Ser Pro Lys Leu Val
                325                 330                 335

Gln His Lys Asn Ile
            340


<210> SEQ ID NO 39
<211> LENGTH: 849
<212> TYPE: DNA
<213> ORGANISM: Bacillus thuringiensis
<220> FEATURE:
<221> NAME/KEY: misc_feature
<222> LOCATION: (1)..(846)
<223> OTHER INFORMATION: TIC1373 (WP_003308447); Bt EG3957

<400> SEQUENCE: 39

atggcagatc aaacagcaaa tattacagat gtagatgcac aaatggacaa gatttcagat      60

ttttatttta aaaacgagtt agaatggaaa gatttacctg aatatcctgg agcatatcat     120

tatattagat tggatagtaa aaaaacaaat atggatttag atttaaaagc gaacaatata     180

aaaaatttaa cttatagtga tttaaatcca gaatatgtcg gtgaaaatga atttgataat     240

acaaatagta atatagacca aacattcaca acagcggcct attcccatca agttacaaac     300

tcggctagta caaatgttac taaagggttt aaagtgggcg gaaaaacaac gcttcttaaa     360

ttaccgattt tattaacaag tggagttgag attaatgcag aatttaactc tgcaacaagt     420

acgacgaata cagttacaga taccaagact ttaactgctt ctccacaaaa tataaaggtt     480

ccagccggta ggaagtttct agttaaagta gatatggcca aaaaaacatt taatggagaa     540

gtagacttta gtgcaacagg atataatgta aaatcaacgc ttaacacgtt agcaacttat     600

tatgcagcag ggttcccacg tccaaataaa tatccatcac ttacatttgt cacagcagat     660

atgtggaaaa agttatctac tagtcaacaa aatcaaataa atggagttaa ttttgattct     720

agtaaagatc ttgtgttaaa tgggaaagcg aatgtacatg ggatttttgg aagtacacta     780

cgtgtgagcg tttatgatat tacagattca aaattatcac ctaaactagt tcaacataaa     840

aacatatga                                                             849


<210> SEQ ID NO 40
<211> LENGTH: 282
<212> TYPE: PRT
<213> ORGANISM: Bacillus thuringiensis
<220> FEATURE:
```

-continued

<221> NAME/KEY: MISC_FEATURE
<222> LOCATION: (1)..(282)
<223> OTHER INFORMATION: TIC1373 (WP_003308447); Bt EG3957

<400> SEQUENCE: 40

Met Ala Asp Gln Thr Ala Asn Ile Thr Asp Val Asp Ala Gln Met Asp
1 5 10 15

Lys Ile Ser Asp Phe Tyr Phe Lys Asn Glu Leu Glu Trp Lys Asp Leu
20 25 30

Pro Glu Tyr Pro Gly Ala Tyr His Tyr Ile Arg Leu Asp Ser Lys Lys
35 40 45

Thr Asn Met Asp Leu Asp Leu Lys Ala Asn Asn Ile Lys Asn Leu Thr
50 55 60

Tyr Ser Asp Leu Asn Pro Glu Tyr Val Gly Glu Asn Glu Phe Asp Asn
65 70 75 80

Thr Asn Ser Asn Ile Asp Gln Thr Phe Thr Thr Ala Ala Tyr Ser His
85 90 95

Gln Val Thr Asn Ser Ala Ser Thr Asn Val Thr Lys Gly Phe Lys Val
100 105 110

Gly Gly Lys Thr Thr Leu Leu Lys Leu Pro Ile Leu Leu Thr Ser Gly
115 120 125

Val Glu Ile Asn Ala Glu Phe Asn Ser Ala Thr Ser Thr Thr Asn Thr
130 135 140

Val Thr Asp Thr Lys Thr Leu Thr Ala Ser Pro Gln Asn Ile Lys Val
145 150 155 160

Pro Ala Gly Arg Lys Phe Leu Val Lys Val Asp Met Ala Lys Lys Thr
165 170 175

Phe Asn Gly Glu Val Asp Phe Ser Ala Thr Gly Tyr Asn Val Lys Ser
180 185 190

Thr Leu Asn Thr Leu Ala Thr Tyr Tyr Ala Ala Gly Phe Pro Arg Pro
195 200 205

Asn Lys Tyr Pro Ser Leu Thr Phe Val Thr Ala Asp Met Trp Lys Lys
210 215 220

Leu Ser Thr Ser Gln Gln Asn Gln Ile Asn Gly Val Asn Phe Asp Ser
225 230 235 240

Ser Lys Asp Leu Val Leu Asn Gly Lys Ala Asn Val His Gly Ile Phe
245 250 255

Gly Ser Thr Leu Arg Val Ser Val Tyr Asp Ile Thr Asp Ser Lys Leu
260 265 270

Ser Pro Lys Leu Val Gln His Lys Asn Ile
275 280

<210> SEQ ID NO 41
<211> LENGTH: 942
<212> TYPE: DNA
<213> ORGANISM: Bacillus cereus
<220> FEATURE:
<221> NAME/KEY: misc_feature
<222> LOCATION: (1)..(780)
<223> OTHER INFORMATION: WP_000699779 (TAA_781-783)
<220> FEATURE:
<221> NAME/KEY: misc_feature
<222> LOCATION: (1)..(99)
<223> OTHER INFORMATION: signal peptide coding sequence
<220> FEATURE:
<221> NAME/KEY: misc_feature
<222> LOCATION: (100)..(780)
<223> OTHER INFORMATION: cryptic peptide coding sequence (TAA_781-783)

<400> SEQUENCE: 41
atgaagattc tatggaaacc tcaaaaaact tttatttcta acctagggat tgtattggga 60
atttcaagta ccctgttttt tggaagtaat gtcatggcag atcaaacagc aaatattaca 120
gatgtagatg tacaaatgga caaaatttcg gatttttatt ttaaaaacga gttacaatgg 180
aaagatttac ctgaatatcc tggagcatat cattatatta gattggatag taaaaaaaca 240
aatatggatt tagatttaaa agcgaacaat ataaaaaatt taacttatag tgatttaaat 300
ccggaatatg tcggtgaaaa tgaatttgat aatacaaata gtaatataga ccaaacattc 360
acaacagcag cctattctca tcaagttaca aactcggcta gtacaaatgt tactaaaggg 420
tttaaagtgg gcggaaaaac aacacttctt aaattaccga ttttattaac aagtggagtt 480
gagattaatg cagaatttaa ctctgcaaca agtacgacga atacagttac agatactaag 540
actttaactg cttctccaca aaatataaag gttccagccg gtaggaaatt tttagttaaa 600
gtagatatgg ccaaaaaaac atttaatgga gaagtagact ttagtgcaac aggatataat 660
gtacaatcaa cgcttaacac gttagcaact tattatgcag caggattccc acgtccaaat 720
aaatatccat cacttacatt tgttacagca gatatgtgga aaaagttatc tactagtcaa 780
taaaatcaaa taaatggagt taactttgat tctagtaaag atcttgtgtt aaatgggaaa 840
gcgaatgtac atgggatttt tggaagtaca ctacgtgtga gcgtttatga tattaccgat 900
tcaaaattat cacctaaact agttcaacaa aaaaacatat ga 942

<210> SEQ ID NO 42
<211> LENGTH: 260
<212> TYPE: PRT
<213> ORGANISM: Bacillus cereus
<220> FEATURE:
<221> NAME/KEY: MISC_FEATURE
<222> LOCATION: (1)..(260)
<223> OTHER INFORMATION: WP_000699779 (C-terminal truncated)
<220> FEATURE:
<221> NAME/KEY: MISC_FEATURE
<222> LOCATION: (1)..(33)
<223> OTHER INFORMATION: signal peptide amino acid sequence
<220> FEATURE:
<221> NAME/KEY: MISC_FEATURE
<222> LOCATION: (34)..(260)
<223> OTHER INFORMATION: mature peptide amino acid sequence (C-terminal
truncated)

<400> SEQUENCE: 42

Met Lys Ile Leu Trp Lys Pro Gln Lys Thr Phe Ile Ser Asn Leu Gly
1 5 10 15

Ile Val Leu Gly Ile Ser Ser Thr Leu Phe Phe Gly Ser Asn Val Met
20 25 30

Ala Asp Gln Thr Ala Asn Ile Thr Asp Val Asp Val Gln Met Asp Lys
35 40 45

Ile Ser Asp Phe Tyr Phe Lys Asn Glu Leu Gln Trp Lys Asp Leu Pro
50 55 60

Glu Tyr Pro Gly Ala Tyr His Tyr Ile Arg Leu Asp Ser Lys Lys Thr
65 70 75 80

Asn Met Asp Leu Asp Leu Lys Ala Asn Asn Ile Lys Asn Leu Thr Tyr
85 90 95

Ser Asp Leu Asn Pro Glu Tyr Val Gly Glu Asn Glu Phe Asp Asn Thr
100 105 110

Asn Ser Asn Ile Asp Gln Thr Phe Thr Thr Ala Ala Tyr Ser His Gln
115 120 125

Val Thr Asn Ser Ala Ser Thr Asn Val Thr Lys Gly Phe Lys Val Gly

```
    130                 135                 140

Gly Lys Thr Thr Leu Leu Lys Leu Pro Ile Leu Leu Thr Ser Gly Val
145                 150                 155                 160

Glu Ile Asn Ala Glu Phe Asn Ser Ala Thr Ser Thr Thr Asn Thr Val
                165                 170                 175

Thr Asp Thr Lys Thr Leu Thr Ala Ser Pro Gln Asn Ile Lys Val Pro
            180                 185                 190

Ala Gly Arg Lys Phe Leu Val Lys Val Asp Met Ala Lys Lys Thr Phe
        195                 200                 205

Asn Gly Glu Val Asp Phe Ser Ala Thr Gly Tyr Asn Val Gln Ser Thr
    210                 215                 220

Leu Asn Thr Leu Ala Thr Tyr Tyr Ala Ala Gly Phe Pro Arg Pro Asn
225                 230                 235                 240

Lys Tyr Pro Ser Leu Thr Phe Val Thr Ala Asp Met Trp Lys Lys Leu
                245                 250                 255

Ser Thr Ser Gln
            260


<210> SEQ ID NO 43
<211> LENGTH: 948
<212> TYPE: DNA
<213> ORGANISM: Artificial Sequence
<220> FEATURE:
<223> OTHER INFORMATION: useful in plants.
<220> FEATURE:
<221> NAME/KEY: misc_feature
<222> LOCATION: (1)..(945)
<223> OTHER INFORMATION: TIC1825.nno; full length
<220> FEATURE:
<221> NAME/KEY: misc_feature
<222> LOCATION: (1)..(99)
<223> OTHER INFORMATION: native Bt signal peptide coding sequence
<220> FEATURE:
<221> NAME/KEY: misc_feature
<222> LOCATION: (100)..(945)
<223> OTHER INFORMATION: mature peptide coding sequence (useful in
      plants)

<400> SEQUENCE: 43

atgaccaacc tgttcaagtc ccagaagacc ttcatcgcca agctgggcat cgtgctgggc      60

attagcagca ccctgttctt cggcagcaac gtgatggccg cccagaccac caacatcacc     120

gacgtggacg cccagatgga caagatcagc gacttctact tcaagaacga gctggagtgg     180

aaggatctcc cggagtaccc tggcgcgtac cactacatcc gcctggacag caagaagacc     240

aacatggacc tcgacctcaa ggccagcaac ctcaagaacc tgacctactc cgatctgcac     300

ccggagtaca tcggcgagaa cgagttcgac aacaccaacg gctccatcga ccagaccttc     360

accactgcct cctactccca ccaagtgacc aacagcgcca gcaccagcgt gaccgagggc     420

ttcaaagtgg gcggcaagac cactctgttc aagctgccta tcctgctgac cgacggcgtg     480

gacatcaccg ctgagttcaa cagcgccacc agcaccacca acaccgtcac tgatacgaag     540

acgctgacgg ctagtcctca gaacatcaag gtgcctgcgg gcaagaagta cctggtcaag     600

gtggacatgg cgaagaagac gttcaacggt gacattgagt tcagcgcgaa tgggaagaac     660

gtgaagtcca agctggacac gcttgccacg tactacgggc cgggctttcc gcgcccgaac     720

aagtacccaa gcctgctgtt cacaacagca gacatgtgga agaagctgtc cacatcgcag     780

cagaatcaga tcaagggcgt tacgttcgac tcgtcgaaga acctgatcct gaatgggaag     840

gcgcacgtga atggaatctt cggaagcaag ctcagggtga gtgtgtacga catcacagat     900
```

tcgaagctga gtccaaagct gatccagcag aagttcatgg agcagtga 948

<210> SEQ ID NO 44
<211> LENGTH: 942
<212> TYPE: DNA
<213> ORGANISM: Artificial Sequence
<220> FEATURE:
<223> OTHER INFORMATION: useful in plants.
<220> FEATURE:
<221> NAME/KEY: misc_feature
<222> LOCATION: (1)..(939)
<223> OTHER INFORMATION: TIC2463.nno; full length
<220> FEATURE:
<221> NAME/KEY: misc_feature
<222> LOCATION: (1)..(99)
<223> OTHER INFORMATION: native Bt signal peptide coding sequence
<220> FEATURE:
<221> NAME/KEY: misc_feature
<222> LOCATION: (100)..(939)
<223> OTHER INFORMATION: mature peptide coding sequence (useful in plants)

<400> SEQUENCE: 44
atgaagatcc tgtggaagcc gcagaagacc ttcatcagca acctggccat cgtgctcggc 60
atcagcagca ccctgttctt cggcagcaac gtgatggccg accagaccgc caacatcacc 120
gacgtggacg cccagatgga caagatcagc gacttctact tcaagaacga gctggagtgg 180
aaggacttgc ccgagtaccc tggcgcgtac cactacatcc gcctggacag caagaagacg 240
aacatggacc tcgacctcaa ggccaacaac atcaagaacc tcacctactc cgacctgaac 300
cctgagtacg tgggcgagaa cgagttcgac aacaccaact ccaacatcga ccagaccttc 360
accaccgccg cctactccca ccaagtgacc aactccgcct ccaccaacgt gaccaagggc 420
ttcaaggtgg gcggcaagac caccctcctc aagctgccta tcctgctgac cagcggcgtg 480
gagatcaacg ccgagttcaa cagcgctacc agcactacca acactgtcac tgacaccaag 540
actctgacgg ctagtcctca gaacatcaag gtgcccgctg gtaggaagtt cctggtcaag 600
gtggacatgg cgaagaagac gttcaacggt gaagtggact tctctgcgac gggctacaac 660
gtcaagagca cgctgaacac gctggcgacg tactacgcgg cgggctttcc tcggccgaac 720
aagtacccgt ctctgacatt cgtcaccgcc gacatgtgga agaagctctc tacctcgcag 780
cagaatcaga tcaacggcgt gaacttcgat agcagcaagg acttggtgct gaatggaaag 840
gccaatgtgc acggaatctt cggctccacc ctgcgtgtta gtgtgtacga catcacagac 900
tcgaagctgt cgccgaagct ggtacagcac aagaacatct ga 942

<210> SEQ ID NO 45
<211> LENGTH: 1014
<212> TYPE: DNA
<213> ORGANISM: Artificial Sequence
<220> FEATURE:
<223> OTHER INFORMATION: useful in plants.
<220> FEATURE:
<221> NAME/KEY: misc_feature
<222> LOCATION: (1)..(1011)
<223> OTHER INFORMATION: TIC2461.nno; full length
<220> FEATURE:
<221> NAME/KEY: misc_feature
<222> LOCATION: (1)..(84)
<223> OTHER INFORMATION: native BT signal peptide coding sequence
<220> FEATURE:
<221> NAME/KEY: misc_feature
<222> LOCATION: (85)..(1011)
<223> OTHER INFORMATION: mature peptide coding sequence (useful in plants)

<400> SEQUENCE: 45

-continued

```
atggagctta agcgcatctg gaagtgcctg accatcagcg ccgtgctgag ccagatcgcc      60

gtgtacccgg tgacctccta cgccgtcagc aacacggagc agaacaccga caacatgaag     120

atcaccgagg agaagtccaa catgatccgc aacggcctgc tgggcaacgt gcacaagtcc     180

tccgtgaagt ccgcctacag cagcaacgtg accaacgtgg acgagcagat gaacaagatc     240

agcgacttct actaccagaa caacctgcgc ggcaaggaga tcagtaccta ctactacgtg     300

aaccagctca aggagaagaa gaccaccatg tccctggacc tgaacgcctc cgacatcaac     360

aacgtgacct acaacgacct ccagccggag tacatcggcg agaacgagtt ccagaacacc     420

acggaccagg accagacctt caccaccgcc gcgtactccc acgctgtcac cgacaccgtc     480

tcctccaccg tcaccaacgg cttcaagatc ggcggtagtg gcgacaccat cttcaagatc     540

ccgatcctgc tcaaggacgg catcaagctc tcggctgagt tcaactcggc taccagcacc     600

accaacacca cgacggacac caagacgctg acggcgtcgc ctcagaacat caaggtgcct     660

gcgggcaaga cgtacaaggt cgtcgtcaac ctgtacaaga agtcgttcga gggtgacatc     720

gacttcacgg gcaaggcgac gaacgtcaac tcgaagctga cggtcaacgc gacgtacgtc     780

gggcacgggt ttccacgccg ggacaaggag cagagctaca cctacgcgac cgcagacatg     840

ctcaaggatc tcacgaacga ccagaggaat cagattaccg ggatctcctt cgataacaac     900

aagaacctca cgctcaatgg aaaggccaag atcgagggaa tctacggaag caagctgcaa     960

gtgagcgtgt acgacatcac gaacaacgca catcgcctgg tgcaagtgtt ctga          1014
```

```
<210> SEQ ID NO 46
<211> LENGTH: 951
<212> TYPE: DNA
<213> ORGANISM: Artificial Sequence
<220> FEATURE:
<223> OTHER INFORMATION: useful in plants.
<220> FEATURE:
<221> NAME/KEY: misc_feature
<222> LOCATION: (1)..(948)
<223> OTHER INFORMATION: TIC3037.nno; full length
<220> FEATURE:
<221> NAME/KEY: misc_feature
<222> LOCATION: (1)..(93)
<223> OTHER INFORMATION: native Bt signal peptide coding sequence
<220> FEATURE:
<221> NAME/KEY: misc_feature
<222> LOCATION: (94)..(948)
<223> OTHER INFORMATION: mature peptide coding sequence (useful in
      plants)

<400> SEQUENCE: 46

atgaagaaca agaagaacat cttcaagatg tgctcggcga ccctggcgct gtcgctcggc      60

gtgacggtgt tcgtgccgac tgcctcctac gctgcgatca ccaacgacaa gttcctgagc     120

ccggtcacca gcaccgactc caacatcacc aacgtggacg actcgatgaa caagacctcc     180

gacttctact acaagaacaa gctggacaac aaggaactgg gcagctactg gaggatcaat     240

tcgctccagt cgaagaagac cacgatggac ctcgagatca actcatcgga catacagaac     300

ctgaagtact ccgactccca gccggagtac atcggtgaga acgagttcaa gaacgacacc     360

aacgaggagc agatcatgac caccgcgacg tactcgcacg aggtgcgcaa cttcgtggac     420

tcgacggtga cgaagggctt ccaggcgaag ggcgagggcg cgttcttcaa gatccctatc     480

ctcctcccgg acggcatcca gctcaacgcc gagttcaact cgaacgacac ggagaagaag     540

accacggacg acatcaagac ccttacggcc agccctcaga acatcaaggt cccggcgggc     600

aagacctaca aggtggaggt gacccttcac aagaagaact tcgtgggcga cattgacttc     660
```

cagggcaagg ctactaacgt caagtcggac ctgaacgtgc gggagatgta cctcggccct 720
gggttccctc ggcccgaccg ctacccgacg tacacctacg acacggcgga catgtggaag 780
gacctgacga acgaccagaa gaaccagata accggcatca agttcgacga caacaagaac 840
ctgatcctga acgggacagc gaagctgaag ggcatctacg ggagcaagtt gcaagtgaac 900
atcttcgaca tcacgaacaa gtccactccc aagctcgtgc aagtgttctg a 951

<210> SEQ ID NO 47
<211> LENGTH: 981
<212> TYPE: DNA
<213> ORGANISM: Artificial Sequence
<220> FEATURE:
<223> OTHER INFORMATION: useful in plants.
<220> FEATURE:
<221> NAME/KEY: misc_feature
<222> LOCATION: (1)..(978)
<223> OTHER INFORMATION: TIC2228.nno; full length
<220> FEATURE:
<221> NAME/KEY: misc_feature
<222> LOCATION: (1)..(78)
<223> OTHER INFORMATION: native Bt signal peptide coding sequence
<220> FEATURE:
<221> NAME/KEY: misc_feature
<222> LOCATION: (79)..(978)
<223> OTHER INFORMATION: mature peptide coding sequence (useful in plants)

<400> SEQUENCE: 47
atgcggaaga aactgatcgt cacgacggcc agcctgtcgc tcgccctcac gtccttcggc 60
tcgatcacca gcctcgcgga gagcaacaac cagcagaaca agcggatcga agtgaacggc 120
acgacctcga acagcagcat cctctctccg atcacgagca acatcattac ggacgtggac 180
cagcagatga acaagatcag cgactactac tacaacaaca acctcaagct caaagacatc 240
ggcgactact accacatcat ccgcctggag aacaagaaca ccaccatgag cttctccctg 300
aacgcggacg acatcaagaa cctccagtac aacgacctcc agccgcagta catcggcgag 360
aacgagttca agaacaccac cgaccaggag cagacgttca cgaccgcgag ctacagccag 420
gcggtgacca acagcgtgag cagcacggtg atccagggct tcaaggccac cagcaccacc 480
tccctcctca agattccgat cctgctgccg gagggcatca acctcaacgc cgagttcaac 540
tcggcctcga acaccaccac gacgaacacg accaccgaga ccctcactgc tcctccgcag 600
aacattaagg tgccctcggg acgcacgtac aaggtcgagg tgaacctgct caagaagaag 660
ttcaccggag acatcgactt ccacgggaag ggcacggacg tcaagagcaa cctcaaggtg 720
cgggccacgt actacgggcc aggctttcct cggccgacga agtaccctag ctacacctac 780
tcgacggcgg acatgtggcg cggcctgacg actgagcaga agaagcagat caccggcgta 840
aacttcaaca acaacaaaga tttgactatc gacgggacca cgaaggtcga gggcatctac 900
ggcagcaacc tggaggtcgt ggtgtacgac atcacgaaca agaacatccc gaagatggtg 960
gagacccgga cattcaagtg a 981

<210> SEQ ID NO 48
<211> LENGTH: 852
<212> TYPE: DNA
<213> ORGANISM: Artificial Sequence
<220> FEATURE:
<223> OTHER INFORMATION: Open Reading Frame TIC1825_12 Variant

<400> SEQUENCE: 48
atggcccaga ccaccaacat caccgacgtg gacgcccaga tggacaagat cagcgacttc 60

```
tacttcaaga acgagctgga gtggaaggat ctcccggagt accctggcgc gtaccactac    120

atccgcctgg acagcaagaa gaccaacatg gacctcgacc tcaaggccag caacctcaag    180

aacctgacct actccgatct gcacccggag tacatcggcg agaacgagtt cgacaacacc    240

aacggctcca tcgaccagac cttcaccact gcctcctact cccaccaagt gaccaacagc    300

gccagcacca gcgtgaccga gggcttcaaa gtgggcggca agaccactct gttcaagctg    360

cctatcctgc tgaccgacgg cgtggacatc accgctgagt tcaacagcgc caccagcacc    420

accaacaccg tcactgatac gaagacgctg acggctagtc ctcagaacat caaggtgcct    480

gcgggcaaga agtacctggt caaggtggac atggcgaaga agacgttcaa cggtgacatt    540

gagttcagcg cgaatgggaa gaacgtgaag tccaccctga acacgcttgc cacgtactac    600

gccgccggct ttccgcgccc gaacaagtac ccaagcctga ccttcgtgac agcagacatg    660

tggaagaagc tgtccacatc gcagcagaat cagatcaagg gcgttacgtt cgactcgtcg    720

aagaacctga tcctgaatgg gaaggcgcac gtgaatggaa tcttcggaag caagctcagg    780

gtgagtgtgt acgacatcac agattcgaag ctgagtccaa agctgatcca gcagaagttc    840

atggagcagt ga                                                        852
```

<210> SEQ ID NO 49
<211> LENGTH: 283
<212> TYPE: PRT
<213> ORGANISM: Artificial Sequence
<220> FEATURE:
<223> OTHER INFORMATION: TIC1825_12 Variant of mature peptide amino acid sequence of SEQ ID NO:2

<400> SEQUENCE: 49

```
Met Ala Gln Thr Thr Asn Ile Thr Asp Val Asp Ala Gln Met Asp Lys
1               5                   10                  15

Ile Ser Asp Phe Tyr Phe Lys Asn Glu Leu Glu Trp Lys Asp Leu Pro
            20                  25                  30

Glu Tyr Pro Gly Ala Tyr His Tyr Ile Arg Leu Asp Ser Lys Lys Thr
        35                  40                  45

Asn Met Asp Leu Asp Leu Lys Ala Ser Asn Leu Lys Asn Leu Thr Tyr
    50                  55                  60

Ser Asp Leu His Pro Glu Tyr Ile Gly Glu Asn Glu Phe Asp Asn Thr
65                  70                  75                  80

Asn Gly Ser Ile Asp Gln Thr Phe Thr Thr Ala Ser Tyr Ser His Gln
                85                  90                  95

Val Thr Asn Ser Ala Ser Thr Ser Val Thr Glu Gly Phe Lys Val Gly
            100                 105                 110

Gly Lys Thr Thr Leu Phe Lys Leu Pro Ile Leu Leu Thr Asp Gly Val
        115                 120                 125

Asp Ile Thr Ala Glu Phe Asn Ser Ala Thr Ser Thr Thr Asn Thr Val
    130                 135                 140

Thr Asp Thr Lys Thr Leu Thr Ala Ser Pro Gln Asn Ile Lys Val Pro
145                 150                 155                 160

Ala Gly Lys Lys Tyr Leu Val Lys Val Asp Met Ala Lys Lys Thr Phe
                165                 170                 175

Asn Gly Asp Ile Glu Phe Ser Ala Asn Gly Lys Asn Val Lys Ser Thr
            180                 185                 190

Leu Asn Thr Leu Ala Thr Tyr Tyr Ala Ala Gly Phe Pro Arg Pro Asn
        195                 200                 205
```

-continued

```
Lys Tyr Pro Ser Leu Thr Phe Val Thr Ala Asp Met Trp Lys Lys Leu
    210                 215                 220

Ser Thr Ser Gln Gln Asn Gln Ile Lys Gly Val Thr Phe Asp Ser Ser
225                 230                 235                 240

Lys Asn Leu Ile Leu Asn Gly Lys Ala His Val Asn Gly Ile Phe Gly
                245                 250                 255

Ser Lys Leu Arg Val Ser Val Tyr Asp Ile Thr Asp Ser Lys Leu Ser
            260                 265                 270

Pro Lys Leu Ile Gln Gln Lys Phe Met Glu Gln
        275                 280


<210> SEQ ID NO 50
<211> LENGTH: 852
<212> TYPE: DNA
<213> ORGANISM: Artificial Sequence
<220> FEATURE:
<223> OTHER INFORMATION: Open Reading Frame TIC1825_13 Variant

<400> SEQUENCE: 50

atggcccaga ccaccaacat caccgacgtg gacgcccaga tggacaagat cagcgacttc      60

tacttcaaga acgagctgga gtggaaggat ctcccggagt accctggcgc gtaccactac     120

atccgcctgg acagcaagaa gaccaacatg gacctcgacc tcaaggccag caacctcaag     180

aacctgacct actccgatct gcacccggag tacatcggcg agaacgagtt cgacaacacc     240

aacggctcca tcgaccagac cttcaccact gcctcctact cccaccaagt gaccaacagc     300

gccagcacca gcgtgaccga gggcttcaaa gtgggcggca agaccactct gttcaagctg     360

cctatcctgc tgaccgacgg cgtggacatc accgctgagt tcaacagcgc caccagcacc     420

accaacaccg tcactgatac gaagacgctg acggctagtc ctcagaacat caaggtgcct     480

gcgggcaaga agtacctggt caaggtggac atggcgaaga agacgttcaa cggtgacatt     540

gagttcagcg cgaatggcta caacgtgaag tccaccctga acacgcttgc cacgtactac     600

gccgccggct ttccgcgccc gaacaagtac ccaagcctga ccttcgtgac agcagacatg     660

tggaagaagc tgtccacatc gcagcagaat cagatcaagg gcgttacgtt cgactcgtcg     720

aaggacctga tcctgaatgg gaaggcgcac gtgaatggaa tcttcggaag caagctcagg     780

gtgagtgtgt acgacatcac agattcgaag ctgagtccaa agctgatcca gcagaagttc     840

atggagcagt ga                                                         852


<210> SEQ ID NO 51
<211> LENGTH: 283
<212> TYPE: PRT
<213> ORGANISM: Artificial Sequence
<220> FEATURE:
<223> OTHER INFORMATION: TIC1825_13 Variant of mature peptide amino
      acid sequence of SEQ ID NO:2

<400> SEQUENCE: 51

Met Ala Gln Thr Thr Asn Ile Thr Asp Val Asp Ala Gln Met Asp Lys
1               5                   10                  15

Ile Ser Asp Phe Tyr Phe Lys Asn Glu Leu Glu Trp Lys Asp Leu Pro
            20                  25                  30

Glu Tyr Pro Gly Ala Tyr His Tyr Ile Arg Leu Asp Ser Lys Lys Thr
        35                  40                  45

Asn Met Asp Leu Asp Leu Lys Ala Ser Asn Leu Lys Asn Leu Thr Tyr
    50                  55                  60

Ser Asp Leu His Pro Glu Tyr Ile Gly Glu Asn Glu Phe Asp Asn Thr
```

-continued

```
65                  70                  75                  80

Asn Gly Ser Ile Asp Gln Thr Phe Thr Thr Ala Ser Tyr Ser His Gln
                85                  90                  95

Val Thr Asn Ser Ala Ser Thr Ser Val Thr Glu Gly Phe Lys Val Gly
            100                 105                 110

Gly Lys Thr Thr Leu Phe Lys Leu Pro Ile Leu Leu Thr Asp Gly Val
        115                 120                 125

Asp Ile Thr Ala Glu Phe Asn Ser Ala Thr Ser Thr Thr Asn Thr Val
    130                 135                 140

Thr Asp Thr Lys Thr Leu Thr Ala Ser Pro Gln Asn Ile Lys Val Pro
145                 150                 155                 160

Ala Gly Lys Lys Tyr Leu Val Lys Val Asp Met Ala Lys Lys Thr Phe
                165                 170                 175

Asn Gly Asp Ile Glu Phe Ser Ala Asn Gly Tyr Asn Val Lys Ser Thr
            180                 185                 190

Leu Asn Thr Leu Ala Thr Tyr Tyr Ala Ala Gly Phe Pro Arg Pro Asn
        195                 200                 205

Lys Tyr Pro Ser Leu Thr Phe Val Thr Ala Asp Met Trp Lys Lys Leu
    210                 215                 220

Ser Thr Ser Gln Gln Asn Gln Ile Lys Gly Val Thr Phe Asp Ser Ser
225                 230                 235                 240

Lys Asp Leu Ile Leu Asn Gly Lys Ala His Val Asn Gly Ile Phe Gly
                245                 250                 255

Ser Lys Leu Arg Val Ser Val Tyr Asp Ile Thr Asp Ser Lys Leu Ser
            260                 265                 270

Pro Lys Leu Ile Gln Gln Lys Phe Met Glu Gln
        275                 280
```

<210> SEQ ID NO 52
<211> LENGTH: 852
<212> TYPE: DNA
<213> ORGANISM: Artificial Sequence
<220> FEATURE:
<223> OTHER INFORMATION: Open Reading Frame TIC1825_15 Variant

<400> SEQUENCE: 52

```
atggcccaga ccaccaacat caccgacgtg gacgcccaga tggacaagat cagcgacttc     60

tacttcaaga acgagctgga gtggaaggat ctcccggagt accctggcgc gtaccactac    120

atccgcctgg acagcaagaa gaccaacatg gacctcgacc tcaaggccag caacctcaag    180

aacctgacct actccgatct gcacccggag tacatcggcg agaacgagtt cgacaacacc    240

aacggctcca tcgaccagac cttcaccact gcctcctact cccaccaagt gaccaacagc    300

gccagcacca gcgtgaccga gggcttcaaa gtgggcggca agaccactct gttcaagctg    360

cctatcctgc tgaccgacgg cgtggacatc accgctgagt tcaacagcgc caccagcacc    420

accaacaccg tcactgatac gaagacgctg acggctagtc ctcagaacat caaggtgcct    480

gcgggcaaga agtacctggt caaggtggac atggcgaaga agacgttcaa cggtgacatt    540

gagttcagcg cgaatggcaa gaacgtgaag tccaccctga acacgcttgc cacgtactac    600

gccgccggct ttccgcgccc gaacaagtac ccaagcctga ccttcgtgac agcagacatg    660

tggaagaagc tgtccacatc gcagcagaat cagatcaacg gcgttacgtt cgactcgtcg    720

aagaacctga tcctgaatgg gaaggcgcac gtgaatggaa tcttcggaag caagctcagg    780

gtgagtgtgt acgacatcac agattcgaag ctgagtccaa agctgatcca gcagaagttc    840
```

atggagcagt ga 852

<210> SEQ ID NO 53
<211> LENGTH: 283
<212> TYPE: PRT
<213> ORGANISM: Artificial Sequence
<220> FEATURE:
<223> OTHER INFORMATION: TIC1825_15 Variant of mature peptide amino acid sequence of SEQ ID NO:2

<400> SEQUENCE: 53

```
Met Ala Gln Thr Thr Asn Ile Thr Asp Val Asp Ala Gln Met Asp Lys
1               5                   10                  15

Ile Ser Asp Phe Tyr Phe Lys Asn Glu Leu Glu Trp Lys Asp Leu Pro
            20                  25                  30

Glu Tyr Pro Gly Ala Tyr His Tyr Ile Arg Leu Asp Ser Lys Lys Thr
        35                  40                  45

Asn Met Asp Leu Asp Leu Lys Ala Ser Asn Leu Lys Asn Leu Thr Tyr
    50                  55                  60

Ser Asp Leu His Pro Glu Tyr Ile Gly Glu Asn Glu Phe Asp Asn Thr
65                  70                  75                  80

Asn Gly Ser Ile Asp Gln Thr Phe Thr Thr Ala Ser Tyr Ser His Gln
                85                  90                  95

Val Thr Asn Ser Ala Ser Thr Ser Val Thr Glu Gly Phe Lys Val Gly
            100                 105                 110

Gly Lys Thr Thr Leu Phe Lys Leu Pro Ile Leu Leu Thr Asp Gly Val
        115                 120                 125

Asp Ile Thr Ala Glu Phe Asn Ser Ala Thr Ser Thr Thr Asn Thr Val
    130                 135                 140

Thr Asp Thr Lys Thr Leu Thr Ala Ser Pro Gln Asn Ile Lys Val Pro
145                 150                 155                 160

Ala Gly Lys Lys Tyr Leu Val Lys Val Asp Met Ala Lys Lys Thr Phe
                165                 170                 175

Asn Gly Asp Ile Glu Phe Ser Ala Asn Gly Lys Asn Val Lys Ser Thr
            180                 185                 190

Leu Asn Thr Leu Ala Thr Tyr Tyr Ala Ala Gly Phe Pro Arg Pro Asn
        195                 200                 205

Lys Tyr Pro Ser Leu Thr Phe Val Thr Ala Asp Met Trp Lys Lys Leu
    210                 215                 220

Ser Thr Ser Gln Gln Asn Gln Ile Asn Gly Val Thr Phe Asp Ser Ser
225                 230                 235                 240

Lys Asn Leu Ile Leu Asn Gly Lys Ala His Val Asn Gly Ile Phe Gly
                245                 250                 255

Ser Lys Leu Arg Val Ser Val Tyr Asp Ile Thr Asp Ser Lys Leu Ser
            260                 265                 270

Pro Lys Leu Ile Gln Gln Lys Phe Met Glu Gln
        275                 280
```

<210> SEQ ID NO 54
<211> LENGTH: 933
<212> TYPE: DNA
<213> ORGANISM: Artificial Sequence
<220> FEATURE:
<223> OTHER INFORMATION: Open Reading Frame TIC2461_5 Variant

<400> SEQUENCE: 54
atggtcagca acacggagca gaacaccgac aacatgaaga tcaccgagga gaagtccaac 60

```
atgatccgca acggcctgct gggcaacgtg cacaagtcct ccgtgaagtc cgcctacagc    120

agcaacgtga ccaacgtgga cgagcagatg aacaagatca gcgacttcta ctaccagaac    180

aacctgcgcg gcaaggagat cagtacctac tactacgtga accagctcaa ggagaagaag    240

accaccatgt ccctggacct gaacgcctcc gacatcaaca acgtgaccta caacgacctc    300

cagccggagt acatcggcga gaacgagttc cagaacacca cggaccagga ccagaccttc    360

accaccgccg cgtactccca cgctgtcacc gacaccgtct cctccaccgt caccaacggc    420

ttcaagatcg gcggtagtgg cgacaccatc ttcaagatcc cgatcctgct caaggacggc    480

atcaagctct cggctgagtt caactcggct accagcacca ccaacaccac gacggacacc    540

aagacgctga cggcgtcgcc tcagaacatc aaggtgcctg cgggcaagac gtacaaggtc    600

gtcgtcaacc tgtacaagaa gtcgttcgag ggtgacatcg acttcacggg caaggcgacg    660

aacgtcaact cgaagctgac ggtcaacgcg acgtacgtcg ggcacgggtt tccacgccgg    720

gacaaggagc agagctacac ctacgcgacc gcagacatgc tcaaggatct cacgaacgac    780

cagaggaatc agattaccgg gatctccttc gataacaaca agaacctcac gctcaatgga    840

aaggccaaga tcgagggaat ctacggaagc aagctgcaag tgagcgtgta cgacatcacg    900

aacaacgcac atcgcctggt gcaagtgttc tga                                 933
```

```
<210> SEQ ID NO 55
<211> LENGTH: 310
<212> TYPE: PRT
<213> ORGANISM: Artificial Sequence
<220> FEATURE:
<223> OTHER INFORMATION: TIC2461_5 Variant of precursor peptide amino
      acid sequence of SEQ ID NO:6

<400> SEQUENCE: 55

Met Val Ser Asn Thr Glu Gln Asn Thr Asp Asn Met Lys Ile Thr Glu
1               5                   10                  15

Glu Lys Ser Asn Met Ile Arg Asn Gly Leu Leu Gly Asn Val His Lys
            20                  25                  30

Ser Ser Val Lys Ser Ala Tyr Ser Ser Asn Val Thr Asn Val Asp Glu
        35                  40                  45

Gln Met Asn Lys Ile Ser Asp Phe Tyr Tyr Gln Asn Asn Leu Arg Gly
    50                  55                  60

Lys Glu Ile Ser Thr Tyr Tyr Tyr Val Asn Gln Leu Lys Glu Lys Lys
65                  70                  75                  80

Thr Thr Met Ser Leu Asp Leu Asn Ala Ser Asp Ile Asn Asn Val Thr
                85                  90                  95

Tyr Asn Asp Leu Gln Pro Glu Tyr Ile Gly Glu Asn Glu Phe Gln Asn
            100                 105                 110

Thr Thr Asp Gln Asp Gln Thr Phe Thr Thr Ala Ala Tyr Ser His Ala
        115                 120                 125

Val Thr Asp Thr Val Ser Ser Thr Val Thr Asn Gly Phe Lys Ile Gly
    130                 135                 140

Gly Ser Gly Asp Thr Ile Phe Lys Ile Pro Ile Leu Leu Lys Asp Gly
145                 150                 155                 160

Ile Lys Leu Ser Ala Glu Phe Asn Ser Ala Thr Ser Thr Thr Asn Thr
                165                 170                 175

Thr Thr Asp Thr Lys Thr Leu Thr Ala Ser Pro Gln Asn Ile Lys Val
            180                 185                 190

Pro Ala Gly Lys Thr Tyr Lys Val Val Val Asn Leu Tyr Lys Lys Ser
        195                 200                 205
```

```
Phe Glu Gly Asp Ile Asp Phe Thr Gly Lys Ala Thr Asn Val Asn Ser
    210                 215                 220

Lys Leu Thr Val Asn Ala Thr Tyr Val Gly His Gly Phe Pro Arg Arg
225                 230                 235                 240

Asp Lys Glu Gln Ser Tyr Thr Tyr Ala Thr Ala Asp Met Leu Lys Asp
                245                 250                 255

Leu Thr Asn Asp Gln Arg Asn Gln Ile Thr Gly Ile Ser Phe Asp Asn
            260                 265                 270

Asn Lys Asn Leu Thr Leu Asn Gly Lys Ala Lys Ile Glu Gly Ile Tyr
        275                 280                 285

Gly Ser Lys Leu Gln Val Ser Val Tyr Asp Ile Thr Asn Asn Ala His
    290                 295                 300

Arg Leu Val Gln Val Phe
305                 310


<210> SEQ ID NO 56
<211> LENGTH: 942
<212> TYPE: DNA
<213> ORGANISM: Artificial Sequence
<220> FEATURE:
<223> OTHER INFORMATION: Open Reading Frame TIC2463_8 Variant

<400> SEQUENCE: 56

atgaagatcc tgtggaagcc gcagaagacc ttcatcagca acctggccat cgtgctcggc      60

gccgccccct tcctgttctt cggcagcaac gtgatggccg accagaccgc caacatcacc     120

gacgtggacg cccagatgga caagatcagc gacttctact tcaagaacga gctggagtgg     180

aaggacttgc ccgagtaccc tggcgcgtac cactacatcc gcctggacag caagaagacg     240

aacatggacc tcgacctcaa ggccaacaac atcaagaacc tcacctactc cgacctgaac     300

cctgagtacg tgggcgagaa cgagttcgac aacaccaact ccaacatcga ccagaccttc     360

accaccgccg cctactccca ccaagtgacc aactccgcct ccaccaacgt gaccaagggc     420

ttcaaggtgg gcggcaagac caccctcctc aagctgccta tcctgctgac cagcggcgtg     480

gagatcaacg ccgagttcaa cagcgctacc agcactacca acactgtcac tgacaccaag     540

actctgacgg ctagtcctca gaacatcaag gtgcccgctg gtaggaagtt cctggtcaag     600

gtggacatgg cgaagaagac gttcaacggt gaagtggact tctctgcgac gggctacaac     660

gtcaagagca cgctgaacac gctggcgacg tactacgcgg cgggctttcc tcggccgaac     720

aagtacccgt ctctgacatt cgtcaccgcc gacatgtgga agaagctctc tacctcgcag     780

cagaatcaga tcaacggcgt gaacttcgat agcagcaagg acttggtgct gaatggaaag     840

gccaatgtgc acggaatctt cggctccacc ctgcgtgtta gtgtgtacga catcacagac     900

tcgaagctgt cgccgaagct ggtacagcac aagaacatct ga                        942


<210> SEQ ID NO 57
<211> LENGTH: 313
<212> TYPE: PRT
<213> ORGANISM: Artificial Sequence
<220> FEATURE:
<223> OTHER INFORMATION: TIC2463_8 Variant of precursor peptide amino
      acid sequence of SEQ ID NO:4

<400> SEQUENCE: 57

Met Lys Ile Leu Trp Lys Pro Gln Lys Thr Phe Ile Ser Asn Leu Ala
1               5                   10                  15

Ile Val Leu Gly Ala Ala Pro Phe Leu Phe Phe Gly Ser Asn Val Met
```

```
            20                  25                  30

Ala Asp Gln Thr Ala Asn Ile Thr Asp Val Asp Ala Gln Met Asp Lys
        35                  40                  45

Ile Ser Asp Phe Tyr Phe Lys Asn Glu Leu Glu Trp Lys Asp Leu Pro
    50                  55                  60

Glu Tyr Pro Gly Ala Tyr His Tyr Ile Arg Leu Asp Ser Lys Lys Thr
65                  70                  75                  80

Asn Met Asp Leu Asp Leu Lys Ala Asn Asn Ile Lys Asn Leu Thr Tyr
                85                  90                  95

Ser Asp Leu Asn Pro Glu Tyr Val Gly Glu Asn Glu Phe Asp Asn Thr
            100                 105                 110

Asn Ser Asn Ile Asp Gln Thr Phe Thr Thr Ala Ala Tyr Ser His Gln
        115                 120                 125

Val Thr Asn Ser Ala Ser Thr Asn Val Thr Lys Gly Phe Lys Val Gly
    130                 135                 140

Gly Lys Thr Thr Leu Leu Lys Leu Pro Ile Leu Leu Thr Ser Gly Val
145                 150                 155                 160

Glu Ile Asn Ala Glu Phe Asn Ser Ala Thr Ser Thr Thr Asn Thr Val
                165                 170                 175

Thr Asp Thr Lys Thr Leu Thr Ala Ser Pro Gln Asn Ile Lys Val Pro
            180                 185                 190

Ala Gly Arg Lys Phe Leu Val Lys Val Asp Met Ala Lys Lys Thr Phe
        195                 200                 205

Asn Gly Glu Val Asp Phe Ser Ala Thr Gly Tyr Asn Val Lys Ser Thr
    210                 215                 220

Leu Asn Thr Leu Ala Thr Tyr Tyr Ala Ala Gly Phe Pro Arg Pro Asn
225                 230                 235                 240

Lys Tyr Pro Ser Leu Thr Phe Val Thr Ala Asp Met Trp Lys Lys Leu
                245                 250                 255

Ser Thr Ser Gln Gln Asn Gln Ile Asn Gly Val Asn Phe Asp Ser Ser
            260                 265                 270

Lys Asp Leu Val Leu Asn Gly Lys Ala Asn Val His Gly Ile Phe Gly
        275                 280                 285

Ser Thr Leu Arg Val Ser Val Tyr Asp Ile Thr Asp Ser Lys Leu Ser
    290                 295                 300

Pro Lys Leu Val Gln His Lys Asn Ile
305                 310
```

<210> SEQ ID NO 58
<211> LENGTH: 942
<212> TYPE: DNA
<213> ORGANISM: Artificial Sequence
<220> FEATURE:
<223> OTHER INFORMATION: Open Reading Frame TIC2463_9 Variant

<400> SEQUENCE: 58

```
atgaagatcc tgtggaagcc gcagaagacc ttcatcagca acctggccat cgtgctcggc     60

atcagcagca ccctgttctt cggcagcaac gtgatgcgcg accagaccgc caacatcacc    120

gacgtggacg cccagatgga caagatcagc gacttctact tcaagaacga gctggagtgg    180

aaggacttgc ccgagtaccc tggcgcgtac cactacatcc gcctggacag caagaagacg    240

aacatggacc tcgacctcaa ggccaacaac atcaagaacc tcacctactc cgacctgaac    300

cctgagtacg tgggcgagaa cgagttcgac aacaccaact ccaacatcga ccagaccttc    360

accaccgccg cctactccca ccaagtgacc aactccgcct ccaccaacgt gaccaagggc    420
```

```
ttcaaggtgg gcggcaagac caccctcctc aagctgccta tcctgctgac cagcggcgtg    480

gagatcaacg ccgagttcaa cagcgctacc agcactacca acactgtcac tgacaccaag    540

actctgacgg ctagtcctca gaacatcaag gtgcccgctg gtaggaagtt cctggtcaag    600

gtggacatgg cgaagaagac gttcaacggt gaagtggact tctctgcgac gggctacaac    660

gtcaagagca cgctgaacac gctggcgacg tactacgcgg cgggctttcc tcggccgaac    720

aagtacccgt ctctgacatt cgtcaccgcc gacatgtgga agaagctctc tacctcgcag    780

cagaatcaga tcaacggcgt gaacttcgat agcagcaagg acttggtgct gaatggaaag    840

gccaatgtgc acggaatctt cggctccacc ctgcgtgtta gtgtgtacga catcacagac    900

tcgaagctgt cgccgaagct ggtacagcac aagaacatct ga                       942
```

```
<210> SEQ ID NO 59
<211> LENGTH: 313
<212> TYPE: PRT
<213> ORGANISM: Artificial Sequence
<220> FEATURE:
<223> OTHER INFORMATION: TIC2463_9 Variant of precursor peptide amino
      acid sequence of SEQ ID NO:4

<400> SEQUENCE: 59

Met Lys Ile Leu Trp Lys Pro Gln Lys Thr Phe Ile Ser Asn Leu Ala
1               5                   10                  15

Ile Val Leu Gly Ile Ser Ser Thr Leu Phe Phe Gly Ser Asn Val Met
            20                  25                  30

Arg Asp Gln Thr Ala Asn Ile Thr Asp Val Asp Ala Gln Met Asp Lys
        35                  40                  45

Ile Ser Asp Phe Tyr Phe Lys Asn Glu Leu Glu Trp Lys Asp Leu Pro
    50                  55                  60

Glu Tyr Pro Gly Ala Tyr His Tyr Ile Arg Leu Asp Ser Lys Lys Thr
65                  70                  75                  80

Asn Met Asp Leu Asp Leu Lys Ala Asn Asn Ile Lys Asn Leu Thr Tyr
                85                  90                  95

Ser Asp Leu Asn Pro Glu Tyr Val Gly Glu Asn Glu Phe Asp Asn Thr
            100                 105                 110

Asn Ser Asn Ile Asp Gln Thr Phe Thr Thr Ala Ala Tyr Ser His Gln
        115                 120                 125

Val Thr Asn Ser Ala Ser Thr Asn Val Thr Lys Gly Phe Lys Val Gly
    130                 135                 140

Gly Lys Thr Thr Leu Leu Lys Leu Pro Ile Leu Leu Thr Ser Gly Val
145                 150                 155                 160

Glu Ile Asn Ala Glu Phe Asn Ser Ala Thr Ser Thr Thr Asn Thr Val
                165                 170                 175

Thr Asp Thr Lys Thr Leu Thr Ala Ser Pro Gln Asn Ile Lys Val Pro
            180                 185                 190

Ala Gly Arg Lys Phe Leu Val Lys Val Asp Met Ala Lys Lys Thr Phe
        195                 200                 205

Asn Gly Glu Val Asp Phe Ser Ala Thr Gly Tyr Asn Val Lys Ser Thr
    210                 215                 220

Leu Asn Thr Leu Ala Thr Tyr Tyr Ala Ala Gly Phe Pro Arg Pro Asn
225                 230                 235                 240

Lys Tyr Pro Ser Leu Thr Phe Val Thr Ala Asp Met Trp Lys Lys Leu
                245                 250                 255

Ser Thr Ser Gln Gln Asn Gln Ile Asn Gly Val Asn Phe Asp Ser Ser
```

-continued

```
            260                 265                 270

Lys Asp Leu Val Leu Asn Gly Lys Ala Asn Val His Gly Ile Phe Gly
        275                 280                 285

Ser Thr Leu Arg Val Ser Val Tyr Asp Ile Thr Asp Ser Lys Leu Ser
    290                 295                 300

Pro Lys Leu Val Gln His Lys Asn Ile
305                 310


<210> SEQ ID NO 60
<211> LENGTH: 942
<212> TYPE: DNA
<213> ORGANISM: Artificial Sequence
<220> FEATURE:
<223> OTHER INFORMATION: Open Reading Frame TIC2463_10 Variant

<400> SEQUENCE: 60

atgaagatcc tgtggaagcc gcagaagacc ttcatcagca acctggccat cgtgctcggc     60

atcagcagca ccctgttctt cggcagcaac gtgatggccg accagaccgc caacatcacc    120

gacgtgcgcg cccagatgga caagatcagc gacttctact tcaagaacga gctggagtgg    180

aaggacttgc ccgagtaccc tggcgcgtac cactacatcc gcctggacag caagaagacg    240

aacatggacc tcgacctcaa ggccaacaac atcaagaacc tcacctactc cgacctgaac    300

cctgagtacg tgggcgagaa cgagttcgac aacaccaact ccaacatcga ccagaccttc    360

accaccgccg cctactccca ccaagtgacc aactccgcct ccaccaacgt gaccaagggc    420

ttcaaggtgg gcggcaagac caccctcctc aagctgccta tcctgctgac cagcggcgtg    480

gagatcaacg ccgagttcaa cagcgctacc agcactacca acactgtcac tgacaccaag    540

actctgacgg ctagtcctca gaacatcaag gtgcccgctg gtaggaagtt cctggtcaag    600

gtggacatgg cgaagaagac gttcaacggt gaagtggact tctctgcgac gggctacaac    660

gtcaagagca cgctgaacac gctggcgacg tactacgcgg cgggctttcc tcggccgaac    720

aagtacccgt ctctgacatt cgtcaccgcc gacatgtgga agaagctctc tacctcgcag    780

cagaatcaga tcaacggcgt gaacttcgat agcagcaagg acttggtgct gaatggaaag    840

gccaatgtgc acggaatctt cggctccacc ctgcgtgtta gtgtgtacga catcacagac    900

tcgaagctgt cgccgaagct ggtacagcac aagaacatct ga                       942


<210> SEQ ID NO 61
<211> LENGTH: 313
<212> TYPE: PRT
<213> ORGANISM: Artificial Sequence
<220> FEATURE:
<223> OTHER INFORMATION: TIC2463_10 Variant of precursor peptide amino
      acid sequence of SEQ ID NO:4

<400> SEQUENCE: 61

Met Lys Ile Leu Trp Lys Pro Gln Lys Thr Phe Ile Ser Asn Leu Ala
1               5                   10                  15

Ile Val Leu Gly Ile Ser Ser Thr Leu Phe Phe Gly Ser Asn Val Met
            20                  25                  30

Ala Asp Gln Thr Ala Asn Ile Thr Asp Val Arg Ala Gln Met Asp Lys
        35                  40                  45

Ile Ser Asp Phe Tyr Phe Lys Asn Glu Leu Glu Trp Lys Asp Leu Pro
    50                  55                  60

Glu Tyr Pro Gly Ala Tyr His Tyr Ile Arg Leu Asp Ser Lys Lys Thr
65                  70                  75                  80
```

-continued

```
Asn Met Asp Leu Asp Leu Lys Ala Asn Asn Ile Lys Asn Leu Thr Tyr
                85                  90                  95

Ser Asp Leu Asn Pro Glu Tyr Val Gly Glu Asn Glu Phe Asp Asn Thr
            100                 105                 110

Asn Ser Asn Ile Asp Gln Thr Phe Thr Thr Ala Ala Tyr Ser His Gln
        115                 120                 125

Val Thr Asn Ser Ala Ser Thr Asn Val Thr Lys Gly Phe Lys Val Gly
    130                 135                 140

Gly Lys Thr Thr Leu Leu Lys Leu Pro Ile Leu Leu Thr Ser Gly Val
145                 150                 155                 160

Glu Ile Asn Ala Glu Phe Asn Ser Ala Thr Ser Thr Thr Asn Thr Val
                165                 170                 175

Thr Asp Thr Lys Thr Leu Thr Ala Ser Pro Gln Asn Ile Lys Val Pro
            180                 185                 190

Ala Gly Arg Lys Phe Leu Val Lys Val Asp Met Ala Lys Lys Thr Phe
        195                 200                 205

Asn Gly Glu Val Asp Phe Ser Ala Thr Gly Tyr Asn Val Lys Ser Thr
    210                 215                 220

Leu Asn Thr Leu Ala Thr Tyr Tyr Ala Ala Gly Phe Pro Arg Pro Asn
225                 230                 235                 240

Lys Tyr Pro Ser Leu Thr Phe Val Thr Ala Asp Met Trp Lys Lys Leu
                245                 250                 255

Ser Thr Ser Gln Gln Asn Gln Ile Asn Gly Val Asn Phe Asp Ser Ser
            260                 265                 270

Lys Asp Leu Val Leu Asn Gly Lys Ala Asn Val His Gly Ile Phe Gly
        275                 280                 285

Ser Thr Leu Arg Val Ser Val Tyr Asp Ile Thr Asp Ser Lys Leu Ser
    290                 295                 300

Pro Lys Leu Val Gln His Lys Asn Ile
305                 310
```